US006607730B1

(12) United States Patent
Murdin et al.

(10) Patent No.: US 6,607,730 B1
(45) Date of Patent: Aug. 19, 2003

(54) CHLAMYDIA ANTIGENS AND CORRESPONDING DNA FRAGMENTS AND USES THEREOF

(75) Inventors: Andrew D. Murdin, Ontario (CA); Raymond P. Oomen, Ontario (CA); Pamela L. Dunn, Ontario (CA)

(73) Assignee: Aventis Pasteur Limited/Aventis Pasteur Limitee, Toronto (CA)

( * ) Notice: Subject to any disclaimer, the term of this patent is extended or adjusted under 35 U.S.C. 154(b) by 0 days.

(21) Appl. No.: 09/430,723

(22) Filed: Oct. 29, 1999

Related U.S. Application Data

(60) Provisional application No. 60/133,071, filed on May 7, 1999, and provisional application No. 60/106,590, filed on Nov. 2, 1998.

(51) Int. Cl.[7] .......................... A61K 39/00; A61K 39/38; A61K 39/02; A61K 39/118; A61K 47/00
(52) U.S. Cl. ............................... 424/263.1; 424/184.1; 424/185.1; 424/190.1; 424/200.1; 424/234.1; 424/278.1; 435/7.36; 530/389.5
(58) Field of Search ...................... 434/263.1; 435/7.36, 435/91.1, 91.41, 91.42, 91.4, 340; 514/44; 530/388.4, 389.5, 3; 935/24, 76, 77, 78, 88

(56) References Cited

FOREIGN PATENT DOCUMENTS

WO    WO 99/27105    6/1999

OTHER PUBLICATIONS

Kalman, et al., Nature Genetics, 21, 385–389 (1999).
Magee, et al., Infection and Immunity, 63:2, 516–521 (1995).
Landers, et al., Infection and Immunity, 59:10, 3774–3777 (1991).
Jackson, et al., Abstracts of the 36th ICAAC, 272 (1996).
Magee, et al., Regional Immunology, 5, 305–311 (1993).
Igletseme, et al., Regional Immunology, 5, 317–324 (1993).
Jones, et al., Vaccine, 13:8, 715–723 (1995).
Pal, et al., Infection and Immunity, 64:12, 5341–5348 (1996).
Hahn, et al., The Journal of the American Medical Association, 266:2, 225–230 (1991).
Allegra, et al., European Respiratory Journal, 7:2, 2165–2168 (1994).
Björnsson, et al., Scandinavian Journal of Infectious Diseases, 28:1, 63–69 (1996).
Hahn, The Journal of Family Practice, 41:4, 345–351 (1995).
Hahn, et al., Epidemiology Infection, 117:3, 513–517 (1996).
Hahn, et al., Annals of Allergy, Asthma and Immunology, 80:1, 45–49 (1998).
Fong, et al., Journal of Clinical Microbiology, 35:1, 48–52 (1997).
Ramirez, et al., Annals of Internal Medicine, 125:12, 979–982 (1996).
Chiu, et al., Circulation, 96:7, 2144–2148 (1997).
Campbell, et al., The Journal of Infectious Diseases, 172:2, 585–588 (1995).

(List continued on next page.)

Primary Examiner—Lynette R. F. Smith
Assistant Examiner—JaNa Hines
(74) Attorney, Agent, or Firm—Michel Morency; Mintz Levin Cohn Ferris Glovsky and Popec PC

(57) ABSTRACT

In summary of this disclosure, the present invention provides a method of nucleic acid, including DNA, immunization of a host, including humans, against disease caused by infection by a strain of Chlamydia, specifically *C. pneumoniae*, employing a vector, containing a nucleotide sequence encoding an POMP91B precursor protein of a strain of *Chlamydia pneumoniae* and a promoter to effect expression of the POMP91B precursor gene in the host. Modifications are possible within the scope of this invention.

5 Claims, 24 Drawing Sheets

```
gctgtcaaaa ttaagagatt aaaactgtgt cttattgtac ttgttttttt acagcctttc  60 ccttattttgt aggataatct ggtttcatct ctacgtgcaa atg aaa acg tct att  115
                                              Met Lys Thr Ser Ile
                                                1           5 cgt aag ttc tta att tct acc aca ctg gcg cca tgt ttt gct tca aca  163
Arg Lys Phe Leu Ile Ser Thr Thr Leu Ala Pro Cys Phe Ala Ser Thr
         10              15                  20 gcg ttt act gta gaa gtt atc atg cct tcc gag aac ttt gat gga tcg  211
Ala Phe Thr Val Glu Val Ile Met Pro Ser Glu Asn Phe Asp Gly Ser
     25              30                  35 agt ggg aag att ttt cct tac aca aca ctt tct gat cct aga ggg aca  259
Ser Gly Lys Ile Phe Pro Tyr Thr Thr Leu Ser Asp Pro Arg Gly Thr
     40              45                  50 ctc tgt att ttt tca ggg gat ctc tac att gcg aat ctt gat aat gcc  307
Leu Cys Ile Phe Ser Gly Asp Leu Tyr Ile Ala Asn Leu Asp Asn Ala
 55              60                  65 ata tcc aga acc tct tcc agt tgc ttt agc aat agg gcg gga gca cta  355
Ile Ser Arg Thr Ser Ser Cys Phe Ser Asn Arg Ala Gly Ala Leu
 70              75              80                  85 caa atc tta gga aaa ggt ggg gtt ttc tcc ttc tta aat atc cgt tct  403
Gln Ile Leu Gly Lys Gly Gly Val Phe Ser Phe Leu Asn Ile Arg Ser
     90              95                  100 tca gct gac gga gcc gcg att agt agt gta atc acc caa aat cct gaa  451
Ser Ala Asp Gly Ala Ala Ile Ser Ser Val Ile Thr Gln Asn Pro Glu
    105             110                 115 cta tgt ccc ttg agt ttt tca gga ttt agt cag atg atc ttc gat aac  499
Leu Cys Pro Leu Ser Phe Ser Gly Phe Ser Gln Met Ile Phe Asp Asn
    120             125             130 tgt gaa tct ttg act tca gat acc tca gcg agt aat gtc ata cct cac  547
Cys Glu Ser Leu Thr Ser Asp Thr Ser Ala Ser Asn Val Ile Pro His
    135             140             145
```

OTHER PUBLICATIONS

Kuo, et al., Arteriosclerosis and Thrombosis, 13:10, 1501–1504 (1993).
Kuo, et al., The Journal of Infectious Diseases, 167:4, 841–849 (1993).
Melnick, et al., The American Journal of Medicine, 95, 499–504 1993).
Saikku, et al., Annals of Internal Medicine, 116:4, 273–278 (1992).
Grayston, et al., The Journal of Infectious Diseases, 168:5, 1231–1235 (1993).
Campos, et al., Investigative Opththalmology & Visual Science, 36:8, 1477–1491 (1995).
Grayston, et al., The Journal of Infectious Diseases, 161:4, 618–625 (1990).
Marrie, Clinical Infectious Diseases, 18:4, 501–515 (1994).
Wang et al., Chlamydial Infections, 329–333 (1986).
Saikku, et al., The Lancet, 2:8618, 983–985 (1988).
Thom, et al., The Journal of the American Medical Association, 268:1, 68–72 (1992).
Linnanmäki, et al., Circulation, 87:4, 1130–1134 (1993).
Bachmaier, et al., Science, 283, 1335–1339 (1999).
Iijima, et al., Journal of Clinical Microbiology, 32:3, 583–588 (1994).
Campbell, et al., Journal of Clinical Microbiology, 28:6, 1261–1264 (1990).
Melgosa, et al., FEMS Microbiology Letters, 112:2, 199–204 (1993).
Watson, et al., Microbiology, 141, 2489–2497 (1995).
Watson, et al., Nucleic Acids Research, 18:7, 5299 (1990).
Melgosa, et al., Infection and Immunity, 62:3, 880–886 (1994).
Takase, et al., Journal of Bacteriology, 169:12, 5692–5699 (1987).
Cagnon, et al., Protein Engineering, 4:7, 843–847 (1991).
Casey, et al., Nucleic Acids Research, 4:5, 1539–1553 (1977).
Kunkel, Proc. Natl. Acad. Sci. USA, 82, 488–492 (1985).
Langeveld, et al., Vaccine, 12:15, 1994.
Snijders, et al., The Journal of General Virology, 72:3, 557–565 (1991).
Dion, et al., Virology, 179:1, 474–477 (1990).
Hughes, et al., Infection and Immunity, 60:9, 3497–3503 (1992).
Wiedmann–Al–Ahmad, et al., Clinical and Diagnostic Laboratory Immunology, 4:6, 700–704 (1997).
McCafferty, et al., Infection and Immunity, 63:6, 2387–2389 (1995).
Campbell, et al., Infection and Immunity, 58:1, 93–97 (1990).
Cotter, et al., Infection and Immunity, 63:12, 4704–4714 (1995).
Chlamydia Genome Project, http://chlamydia–www.berkeley.edu:4231, updated Sep. 23, 1999.
Shor, et al, S AFR Med Journal, 82, 158–161 (1992).

```
gctgtcaaaa ttaagagatt aaaactgtgt cttattgtac ttgttttttt acagcctttc    60
cctTatttgt aggataatct ggtttcatct ctacgtgcaa atg aaa acg tct att    115
                                            Met Lys Thr Ser Ile
                                             1                5 cgt aag ttc tta att tct acc aca ctg gcg cca tgt ttt gct tca aca    163
Arg Lys Phe Leu Ile Ser Thr Thr Leu Ala Pro Cys Phe Ala Ser Thr
             10              15              20 gcg ttt act gta gaa gtt atc atg cct tcc gag aac ttt gat gga tcg    211
Ala Phe Thr Val Glu Val Ile Met Pro Ser Glu Asn Phe Asp Gly Ser
         25              30              35 agt ggg aag att ttt cct tac aca aca ctt tct gat cct aga ggg aca    259
Ser Gly Lys Ile Phe Pro Tyr Thr Thr Leu Ser Asp Pro Arg Gly Thr
         40              45              50 ctc tgt att ttt tca ggg gat ctc tac att gcg aat ctt gat aat gcc    307
Leu Cys Ile Phe Ser Gly Asp Leu Tyr Ile Ala Asn Leu Asp Asn Ala
     55              60              65 ata tcc aga acc tct tcc agt tgc ttt agc aat agg gcg gga gca cta    355
Ile Ser Arg Thr Ser Ser Ser Cys Phe Ser Asn Arg Ala Gly Ala Leu
 70              75              80              85 caa atc tta gga aaa ggt ggg gtt ttc tcc ttc tta aat atc cgt tct    403
Gln Ile Leu Gly Lys Gly Gly Val Phe Ser Phe Leu Asn Ile Arg Ser
             90              95             100 tca gct gac gga gcc gcg att agt agt gta atc acc caa aat cct gaa    451
Ser Ala Asp Gly Ala Ala Ile Ser Ser Val Ile Thr Gln Asn Pro Glu
            105             110             115 cta tgt ccc ttg agt ttt tca gga ttt agt cag atg atc ttc gat aac    499
Leu Cys Pro Leu Ser Phe Ser Gly Phe Ser Gln Met Ile Phe Asp Asn
        120             125             130 tgt gaa tct ttg act tca gat acc tca gcg agt aat gtc ata cct cac    547
Cys Glu Ser Leu Thr Ser Asp Thr Ser Ala Ser Asn Val Ile Pro His
        135             140             145
```

FIG. 1A

```
gca tcg gcg att tac gct aca acg ccc atg ctc ttt aca aac aat gac    595
Ala Ser Ala Ile Tyr Ala Thr Thr Pro Met Leu Phe Thr Asn Asn Asp
150             155             160             165 tcc ata cta ttc caa tac aac cgt tct gca gga ttt gga gct gcc att    643
Ser Ile Leu Phe Gln Tyr Asn Arg Ser Ala Gly Phe Gly Ala Ala Ile
            170             175             180 cga ggc aca agc atc aca ata gaa aat acg aaa aag agc ctt ctc ttt    691
Arg Gly Thr Ser Ile Thr Ile Glu Asn Thr Lys Lys Ser Leu Leu Phe
                185             190             195 aat ggt aat gga tcc atc tct aat gga ggg gcc ctc acg gga tct gca    739
Asn Gly Asn Gly Ser Ile Ser Asn Gly Gly Ala Leu Thr Gly Ser Ala
        200             205             210 gcg atc aac ctc atc aac aat agc gct cct gtg att ttc tca acg aat    787
Ala Ile Asn Leu Ile Asn Asn Ser Ala Pro Val Ile Phe Ser Thr Asn
    215             220             225 gct aca ggg atc tat ggt ggg gct att tac ctt acc gga gga tct atg    835
Ala Thr Gly Ile Tyr Gly Gly Ala Ile Tyr Leu Thr Gly Gly Ser Met
230             235             240             245 ctc acc tct ggg aac ctc tca gga gtc ttg ttc gtt aat aat agc tcg    883
Leu Thr Ser Gly Asn Leu Ser Gly Val Leu Phe Val Asn Asn Ser Ser
            250             255             260 cgc tca gga ggc gct atc tat gct aac gga aat gtc aca ttt tct aat    931
Arg Ser Gly Gly Ala Ile Tyr Ala Asn Gly Asn Val Thr Phe Ser Asn
                265             270             275 aac agc gac ctg act ttc caa aac aat aca gca tct cca caa aac tcc    979
Asn Ser Asp Leu Thr Phe Gln Asn Asn Thr Ala Ser Pro Gln Asn Ser
        280             285             290 tta cct gca cct aca cct cca cct aca cca cca gca gtc act cct ttg    1027
Leu Pro Ala Pro Thr Pro Pro Pro Thr Pro Pro Ala Val Thr Pro Leu
    295             300             305
```

FIG. 1B

```
tta gga tat gga ggc gcc atc ttc tgt act cct cca gct acc ccc cca    1075
Leu Gly Tyr Gly Gly Ala Ile Phe Cys Thr Pro Pro Ala Thr Pro Pro
310             315                 320                 325 cca aca ggt gtt agc ctg act ata tct gga gaa aac agc gtt aca ttc    1123
Pro Thr Gly Val Ser Leu Thr Ile Ser Gly Glu Asn Ser Val Thr Phe
                330                 335                 340 cta gaa aac att gcc tcc gaa caa gga gga gcc ctc tat ggc aaa aag    1171
Leu Glu Asn Ile Ala Ser Glu Gln Gly Gly Ala Leu Tyr Gly Lys Lys
            345                 350                 355 atc tct ata gat tct aat aaa tct aca ata ttt ctt gga aat aca gct    1219
Ile Ser Ile Asp Ser Asn Lys Ser Thr Ile Phe Leu Gly Asn Thr Ala
            360                 365                 370 gga aaa gga ggc gct att gct att ccc gaa tct ggg gag ctc tct cta    1267
Gly Lys Gly Gly Ala Ile Ala Ile Pro Glu Ser Gly Glu Leu Ser Leu
        375                 380                 385 tcc gca aat caa ggt gat atc ctc ttt aac aag aac ctc agc atc act    1315
Ser Ala Asn Gln Gly Asp Ile Leu Phe Asn Lys Asn Leu Ser Ile Thr
390                 395                 400                 405 agt ggg aca cct act cgc aat agt att cac ttc gga aaa gat gcc aag    1363
Ser Gly Thr Pro Thr Arg Asn Ser Ile His Phe Gly Lys Asp Ala Lys
                410                 415                 420 ttt gcc act cta ggg aat acg caa ggc tat acc cta tac ttc tat gat    1411
Phe Ala Thr Leu Gly Asn Thr Gln Gly Tyr Thr Leu Tyr Phe Tyr Asp
            425                 430                 435 ccg att aca tct gat gat tta tct gct gca tcc gca gcc gct act gtg    1459
Pro Ile Thr Ser Asp Asp Leu Ser Ala Ala Ser Ala Ala Ala Thr Val
            440                 445                 450 gtc gtc aat ccc aaa gcc agt gca gat ggt gcg tat tca ggg act att    1507
Val Val Asn Pro Lys Ala Ser Ala Asp Gly Ala Tyr Ser Gly Thr Ile
455                 460                 465
```

FIG. 1C

| | | | | | | | | | | | | | | | |
|---|---|---|---|---|---|---|---|---|---|---|---|---|---|---|---|
| gtc | ttt | tca | gga | gaa | acc | ctc | act | gct | acc | gaa | gca | gca | acc | cct | gca | 1555 |
| Val | Phe | Ser | Gly | Glu | Thr | Leu | Thr | Ala | Thr | Glu | Ala | Ala | Thr | Pro | Ala |
| 470 | | | | 475 | | | | | 480 | | | | | 485 | | aat gct aca tct aca tta aac caa aag cta gaa ctt gaa ggc ggt act    1603
Asn Ala Thr Ser Thr Leu Asn Gln Lys Leu Glu Leu Glu Gly Gly Thr
            490                 495                 500 ctc gct tta aga aac ggt gct acc tta aat gtt cat aac ttc acg caa    1651
Leu Ala Leu Arg Asn Gly Ala Thr Leu Asn Val His Asn Phe Thr Gln
        505                 510                 515 gat gaa aag tcc gtc gtc atc atg gat gca ggg acc aca tta gca act    1699
Asp Glu Lys Ser Val Val Ile Met Asp Ala Gly Thr Thr Leu Ala Thr
        520                 525                 530 aca aat gga gct aat aat act gac ggt gct atc acc tta aac aag ctt    1747
Thr Asn Gly Ala Asn Asn Thr Asp Gly Ala Ile Thr Leu Asn Lys Leu
        535                 540                 545 gta atc aat ctg gat tct ttg gat ggc act aaa gcg gct gtc gtt aat    1795
Val Ile Asn Leu Asp Ser Leu Asp Gly Thr Lys Ala Ala Val Val Asn
550                 555                 560                 565 gtg cag agt acc aat gga gct ctc act ata tcc gga act tta gga ctt    1843
Val Gln Ser Thr Asn Gly Ala Leu Thr Ile Ser Gly Thr Leu Gly Leu
            570                 575                 580 gtg aaa aac tct caa gat tgc tgt gac aac cac ggg atg ttt aat aaa    1891
Val Lys Asn Ser Gln Asp Cys Cys Asp Asn His Gly Met Phe Asn Lys
            585                 590                 595 gat tta cag caa gtt ccg att tta gaa ctc aaa gcg act tca aat act    1939
Asp Leu Gln Gln Val Pro Ile Leu Glu Leu Lys Ala Thr Ser Asn Thr
        600                 605                 610 gta acc act acg gac ttc agt ctc ggc aca aac ggc tat cag caa tct    1987
Val Thr Thr Thr Asp Phe Ser Leu Gly Thr Asn Gly Tyr Gln Gln Ser
        615                 620                 625 ccc tat ggg tat caa gga act tgg gag ttt acc ata gac acg aca acc    2035
Pro Tyr Gly Tyr Gln Gly Thr Trp Glu Phe Thr Ile Asp Thr Thr Thr
630                 635                 640                 645

FIG. 1D

```
cat acg gtc aca gga aat tgg aaa aaa acc ggt tat ctt cct cat ccg    2083
His Thr Val Thr Gly Asn Trp Lys Lys Thr Gly Tyr Leu Pro His Pro
            650                 655                 660 gag cgt ctt gct ccc ctc att cct aat agc cta tgg gca aac gtc ata    2131
Glu Arg Leu Ala Pro Leu Ile Pro Asn Ser Leu Trp Ala Asn Val Ile
            665                 670                 675 gat tta cga gct gta agt caa gcg tca gca gct gat ggc gaa gat gtc    2179
Asp Leu Arg Ala Val Ser Gln Ala Ser Ala Ala Asp Gly Glu Asp Val
            680                 685                 690 cct ggg aag caa ctg agc atc aca gga att aca aat ttc ttc cat gcg    2227
Pro Gly Lys Gln Leu Ser Ile Thr Gly Ile Thr Asn Phe Phe His Ala
            695                 700                 705 aat cat acc ggt gat gca cgc agc tac cgc cat atg ggt gga ggc tac    2275
Asn His Thr Gly Asp Ala Arg Ser Tyr Arg His Met Gly Gly Gly Tyr
710                 715                 720                 725 ctc atc aat acc tac aca cgc atc act cca gat gct gcg tta agt cta    2323
Leu Ile Asn Thr Tyr Thr Arg Ile Thr Pro Asp Ala Ala Leu Ser Leu
            730                 735                 740 ggt ttt gga cag ctg ttt aca aaa tct aag gat tac ctc gta ggt cac    2371
Gly Phe Gly Gln Leu Phe Thr Lys Ser Lys Asp Tyr Leu Val Gly His
            745                 750                 755 ggt cat tct aac gtt tat ttc gct aca gta tac tct aac atc acc aag    2419
Gly His Ser Asn Val Tyr Phe Ala Thr Val Tyr Ser Asn Ile Thr Lys
            760                 765                 770 tct ctg ttt gga tca tcg aga ttc ttc tca gga ggc act tct cga gtt    2467
Ser Leu Phe Gly Ser Ser Arg Phe Phe Ser Gly Gly Thr Ser Arg Val
            775                 780                 785 acc tat agc cgt agc aat gag aaa gta aag act tca tat aca aaa ttg    2515
Thr Tyr Ser Arg Ser Asn Glu Lys Val Lys Thr Ser Tyr Thr Lys Leu
790                 795                 800                 805 cct aaa ggg cgc tgc tct tgg agt aac aat tgc tgg tta gga gaa ctc    2563
Pro Lys Gly Arg Cys Ser Trp Ser Asn Asn Cys Trp Leu Gly Glu Leu
            810                 815                 820
```

FIG. 1E

```
gaa ggg aac ctt ccc atc act ctc tct tct cgc atc tta aac ctc aag      2611
Glu Gly Asn Leu Pro Ile Thr Leu Ser Ser Arg Ile Leu Asn Leu Lys
            825                 830                 835 cag atc att ccc ttt gta aaa gct gaa gtt gct tac gcg act cat ggg      2659
Gln Ile Ile Pro Phe Val Lys Ala Glu Val Ala Tyr Ala Thr His Gly
            840                 845                 850 ggc atc caa gaa aat acc ccc gag ggg agg att ttt gga cac ggt cat      2707
Gly Ile Gln Glu Asn Thr Pro Glu Gly Arg Ile Phe Gly His Gly His
855                 860                 865 cta ctc aac gtt gca gtt ccc gta ggc gtc cgc ttt ggt aaa aat tct      2755
Leu Leu Asn Val Ala Val Pro Val Gly Val Arg Phe Gly Lys Asn Ser
870                 875                 880                 885 cat aat cga cca gat ttt tac act ata atc gta gcc tat gct cct gat      2803
His Asn Arg Pro Asp Phe Tyr Thr Ile Ile Val Ala Tyr Ala Pro Asp
                890                 895                 900 gtc tat cgt cac aat cct gat tgc gat acg aca tta cct att aat gga      2851
Val Tyr Arg His Asn Pro Asp Cys Asp Thr Thr Leu Pro Ile Asn Gly
            905                 910                 915 gct acg tgg acc tct ata ggg aat aat cta acc aga agt act ttg cta      2899
Ala Thr Trp Thr Ser Ile Gly Asn Asn Leu Thr Arg Ser Thr Leu Leu
            920                 925                 930 gta caa gca tcc agc cat act tca gta aat gat gtt cta gag atc ttc      2947
Val Gln Ala Ser Ser His Thr Ser Val Asn Asp Val Leu Glu Ile Phe
            935                 940                 945 ggg cac tgt gga tgt gat att cgc aga acc tcc cgt aaa tat act cta      2995
Gly His Cys Gly Cys Asp Ile Arg Arg Thr Ser Arg Lys Tyr Thr Leu
950                 955                 960                 965 gat ata gga agc aaa tta cga ttt taaaccttat ttaacgacag ggttgaggca     3049
Asp Ile Gly Ser Lys Leu Arg Phe
                970 tgcctctttc tttcaaatct tcatcttttt gtctacttgc ctgtttatgt agtgcaagtt   3109 gcgcgtttgc tgagactaga ctcggaggga actttgttcc t                       3150
```

FIG. 1F

```
              MseI                               RsaI
  Tsp509I      |      MseI    TaaI       TatI    |          CviJI
     | |       |       |       |          | |                 |
     GCTGTCAAAATTAAGAGATTAAAACTGTGTCTTATTGTACTTGTTTTTTTACAGCCTTTC
   1 ---------+---------+---------+---------+---------+---------+ 60
     CGACAGTTTTAATTCTCTAATTTTGACACAGAATAACATGAACAAAAAAATGTCGGAAAG

CviRI
                              BsaAI   |
                              MaeII|  |          MaeII
                                || |                |
     CCTTATTTGTAGGATAATCTGGTTTCATCTCTACGTGCAAATGAAAACGTCTATTCGTAA
  61 ---------+---------+---------+---------+---------+---------+ 120
     GGAATAAACATCCTATTAGACCAAAGTAGAGATGCACGTTTACTTTTGCAGATAAGCATT

NlaIII
                    HaeII  |
                    HhaI|  |
                    BsrI|| |
                    NlaIV|| |
                    TspRI|| |
                    BsaHI||| |
  Tsp509I           NarI||| |                   TaaI
    MseI|           BanI|||| |       MwoI       SfcI|
     ||              |||||  |         |           ||
     GTTCTTAATTTCTACCACACTGGCGCCATGTTTTGCTTCAACAGCGTTTACTGTAGAAGT
 121 ---------+---------+---------+---------+---------+---------+ 180
     CAAGAATTAAAGATGGTGTGACCGCGGTACAAAACGAAGTTGTCGCAAATGACATCTTCA

TaqI
      Hpy188IX                DpnI|
       CjePI        |        Sau3AI||                        AlwI
       NlaIII       |         BccI| ||   AlwI CjePI   MboII  BsbI  |
         |         |           |  |||     |    |       |      |   | |
     TATCATGCCTTCCGAGAACTTTGATGGATCGAGTGGGAAGATTTTTCCTTACACAACACT
 181 ---------+---------+---------+---------+---------+---------+ 240
     ATAGTACGGAAGGCTCTTGAAACTACCTAGCTCACCCTTCTAAAAAGGAATGTGTTGTGA
```

FIG. 2A

```
               BfaI
      DpnI       |
      MnlI|      |                            DpnI
   Sau3AI||      |                          BstYI  |            Hpy178III
 Hpy188IX|||     |                         Sau3AI  |  AlwI  HinfI       |
         ||||    |  Hin4I         BsmFI      BplI  | |BsrDI  TfiI       |
         ||||    |    |             |         |   | |  |     |         |
         TTCTGATCCTAGAGGGACACTCTGTATTTTTTCAGGGGATCTCTACATTGCGAATCTTGA
   241   ---------+---------+---------+---------+---------+---------+  300
         AAGACTAGGATCTCCCTGTGAGACATAAAAAAGTCCCCTAGAGATGTAACGCTTAGAACT MnlI                       BsiHKAI
         Hpy178III         EarI      |      FauI               Bsp1286I
             MboII|   XmnI BsrI|     |  Sth132I|      AciI           |
                 ||     |    ||     |     ||          |             |
         TAATGCCATATCCAGAACCTCTTCCAGTTGCTTTAGCAATAGGGCGGGAGCACTACAAAT
   301   ---------+---------+---------+---------+---------+---------+  360
         ATTACGGTATAGGTCTTGGAGAAGGTCAACGAAATCGTTATCCCGCCCTCGTGATGTTTA ThaI
                                                                  AciI |
                                                                 Fnu4HI|
                                                         AluI     TauI |
                                                 MboII   CviJI   CviJI| |
                                          MseI     |    MspA1I   NlaIV|| |
         DdeI                    Eco57I    |  |     PvuII   MwoI  |||| |
           |                       |       |  |       |       |   |||| |
         CTTAGGAAAAGGTGGGGTTTTCTCCTTCTTAAATATCCGTTCTTCAGCTGACGGAGCCGC
   361   ---------+---------+---------+---------+---------+---------+  420
         GAATCCTTTTCCACCCCAAAAGAGGAAGAATTTATAGGCAAGAAGTCGACTGCCTCGGCG Hpy178III
          HphI   BsmFI   |TaqII    SmlI    Hpy178III
            |     |      |   |      |         |
         GATTAGTAGTGTAATCACCCAAAATCCTGAACTATGTCCCTTGAGTTTTTCAGGATTTAG
   421   ---------+---------+---------+---------+---------+---------+  480
         CTAATCATCACATTAGTGGGTTTTAGGACTTGATACAGGGAACTCAAAAAGTCCTAAATC
```

FIG. 2B

```
              DpnI             HinfI
       Sau3AI  |               TfiI
  Hpy188IX |  |        TaaI      |              BbvCI
   Bce83I| |  |        Eco57I  | |              Bpu10I            BseMII
    MboII| |  |TaqI    |    |  | |     Hpy188IX   DdeI     MnlI       |
       || |  ||   |    |    |  | |         |        |        |        |
       TCAGATGATCTTCGATAACTGTGAATCTTTGACTTCAGATACCTCAGCGAGTAATGTCAT
  481  ---------+---------+---------+---------+---------+---------+  540
       AGTCTACTAGAAGCTATTGACACTTAGAAACTGAAGTCTATGGAGTCGCTCATTACAGTA MwoI                               HinfI
             SfaNI       |                                BsaXI|
        MnlI   |         |           NlaIII        PleI        ||
          |   ||         |             |             |         ||
       ACCTCACGCATCGGCGATTTACGCTACAACGCCCATGCTCTTTACAAACAATGACTCCAT
  541  ---------+---------+---------+---------+---------+---------+  600
       TGGAGTGCGTAGCCGCTAAATGCGATGTTGCGGGTACGAGAAATGTTTGTTACTGAGGTA PstI
                     CviRI  |             MnlI
                      BbvI| |            Fnu4HI |
                    AceIII|| |             AluI| |
                      SfcI|| |             CviJI| |
     Tth111II          TaaI ||| |            TseI| | TaqI
        |               |    |||  |          |||    |
       ACTATTCCAATACAACCGTTCTGCAGGATTTGGAGCTGCCATTCGAGGCACAAGCATCAC
  601  ---------+---------+---------+---------+---------+---------+  660
       TGATAAGGTTATGTTGGCAAGACGTCCTAAACCTCGACGGTAAGCTCCGTGTTCGTAGTG MnlI
                                                  AlwI|
                                              BccI    ||
                                             DpnI  |  ||
                                            NlaIV  |  ||
                                           BamHI   |  ||
                                           BstYI   |  ||    EcoO109I
         Tth111II                          Sau3AI  |  ||    Sau96I
      SfaNI   |          CviJI   MseI  AlwI   |    |  ||    Sth132I
         |    |            |      |     |     |    |  ||      |
       AATAGAAAATACGAAAAGAGCCTTCTCTTTAATGGTAATGGATCCATCTCTAATGGAGG
  661  ---------+---------+---------+---------+---------+---------+  720
       TTATCTTTTATGCTTTTCTCGGAAGAGAAATTACCATTACCTAGGTAGAGATTACCTCC
```

FIG. 2C

```
                              DpnI
                          Sau3AI |
                            BplI| |
       ApaI                 AlwI|| |
       BanII                PstI|| |
       Bsp1286I            Fnu4HI||| |
       BmgI |              CviRI|||| |
       BseSI |              TseI|||| |
       CviJI |              SfcI ||||| |
       HaeIII|              MnlI| ||||| |
       NlaIV |              DpnI|| |||||| |                     HaeII
       EcoO109I|            BstYI||| |||||| |                    HhaI|
       Hin4I|               Sau3AI|||| |||||| |                  Eco47III||
       NlaIV|               BscGI| |||| |||||| | BbvI            MnlI    |||
       Sau96I|           |    ||  ||||  ||||||  |   |              |       |||
         || |           || ||| ||||||| |        |                 |       |||
           GGCCCTCACGGGATCTGCAGCGATCAACCTCATCAACAATAGCGCTCCTGTGATTTTCTC
       721 ---------+---------+---------+---------+---------+---------+ 780
           CCGGGAGTGCCCTAGACGTCGCTAGTTGGAGTAGTTGTTATCGCGAGGACACTAAAAGAG

AlwI
                                                                Hin4I |
                                                                 DpnI | |
                                                                 HphI | |
                              DpnI                               BstYI| | |
                              BstYI|                            Sau3AI| | |
                              Sau3AI|                             MspI| | |
                    BsmI      |   |                              BsaWI| | |
                    SfcI|     |   |                              CjePI|| | |
                    CjePI ||  |   |   AlwI  CviJI                MnlI ||| | |
                      |||     |||  |   |     |                    ||||  | |
           AACGAATGCTACAGGGATCTATGGTGGGCTATTTACCTTACCGGAGGATCTATGCTCAC
       781 ---------+---------+---------+---------+---------+---------+ 840
           TTGCTTACGATGTCCCTAGATACCACCCCGATAAATGGAATGGCCTCCTAGATACGAGTG
```

FIG. 2D

```
                              BseRI
                              BccI  |
                              BpmI| |
                              HaeII| |
                              HhaI|| |
                             Hin4I||| |
                             NlaIV||| |
                             BsaHI|||| |
                              NarI|||| |
                              BanI||||| |
                             MboII||||| |
                   CjeI          ||||||| |
                   CjeI     |    ||||||| |
                   CjePI    |    ||||||| |                 CjeI
                   Bsp24I|  |    ||||||| |                 MnlI|
                    MnlI|   |    ||||||| |                 CjeI||
                    BslI ||  |   ||||||| |   RsaI    AluI   |||
                  EcoNI  |  ||   ||||||| |   | TatI |  CviJI  |||          BslI
                  |  |   |  ||   ||||||| |   |   |  |  |      |||           |
              TCCTTTGTTAGGATATGGAGGCGCCATCTTCTGTACTCCTCCAGCTACCCCCCCACCAAC
      1021    ---------+---------+---------+---------+---------+---------+  1080
              AGGAAACAATCCTATACCTCCGCGGTAGAAGACATGAGGAGGTCGATGGGGGGGTGGTTG

CviJI                        CjeI
      Bsp24I         |                          CjePI|                Hpy188IX
      CjeI           |     Hpy178III       Bsp24I||   BfaI    BsaXI     |
      CjePI          |          CjeI|     MaeIII |||BpmI |  BsrDI  |     |
      |   |          |          |  ||      |  ||| |   |  |    |     |    |
              AGGTGTTAGCCTGACTATATCTGGAGAAAACAGCGTTACATTCCTAGAAAACATTGCCTC
      1081    ---------+---------+---------+---------+---------+---------+  1140
              TCCACAATCGGACTGATATAGACCTCTTTTGTCGCAATGTAAGGATCTTTTGTAACGGAG

BplI
                                      DpnI
                              BanII   BglII  |
                              Bsp1286I BstYI |
                              CviJI  | Sau3AI|
                              Hin4I| |       |
                 MnlI MnlI   NlaIV| |  BseRI  |        HinfI
                   |   |      ||| |   |     ||SfcI  TfiI              SspI
                   |   |      ||| |   |     ||  |    |                  |
              CGAACAAGGAGGAGCCCTCTATGGCAAAAGATCTCTATAGATTCTAATAAATCTACAAT
      1141    ---------+---------+---------+---------+---------+---------+  1200
              GCTTGTTCCTCCTCGGGAGATACCGTTTTTCTAGAGATATCTAAGATTATTTAGATGTTA
```

FIG. 2F

```
                                                      BslI      BanII
                     MnlI                          Sth132I    BsiHKAI
           AluI       |                               BslI|   Bsp1286I
           CviJI      |                              HinfI||      SacI
           MspA1I     |           HaeII               TfiI||     AluI |
           PvuII      |           HhaI|           Hpy178III||    CviJI|
           |   |      |            ||              |   ||           | |
           ATTTCTTGGAAATACAGCTGGAAAAGGAGGCGCTATTGCTATTCCCGAATCTGGGGAGCT
1201       ---------+---------+---------+---------+---------+---------+  1260
           TAAAGAACCTTTATGTCGACCTTTTCCTCCGCGATAACGATAAGGGCTTAGACCCCTCGA BseMII
                                                                SfaNI|
                                                    BbvCI       BfaI ||
                                        MseI       Bpu10I       MnlI|||
            AciI            EcoRV       HphI| MnlI  DdeI        SpeI|||
             |                |          ||   |      |           || ||
           CTCTCTATCCGCAAATCAAGGTGATATCCTCTTTAACAAGAACCTCAGCATCACTAGTGG
1261       ---------+---------+---------+---------+---------+---------+  1320
           GAGAGATAGGCGTTTAGTTCCACTATAGGAGAAATTGTTCTTGGAGTCGTAGTGATCACC Hpy188IX                              BslI
           Hin4I    BsmFI     SfaNI   |                MwoI         BfaI|
             |       |         | |                     |             ||
           GACACCTACTCGCAATAGTATTCACTTCGGAAAAGATGCCAAGTTTGCCACTCTAGGGAA
1321       ---------+---------+---------+---------+---------+---------+  1380
           CTGTGGATGAGCGTTATCATAAGTGAAGCCTTTTCTACGGTTCAAACGGTGAGATCCCTT
```

FIG. 2G

```
                    BfaI
                    AluI |                RsaI
        MseI        CviJI |       AciI    |       MseI        TaaI
        |           ||           |       |       |           |
        TACATCTACATTAAACCAAAAGCTAGAACTTGAAGGCGGTACTCTCGCTTTAAGAAACGG
1561    ---------+---------+---------+---------+---------+---------+ 1620
        ATGTAGATGTAATTTGGTTTTCGATCTTGAACTTCCGCCATGAGAGCGAAATTCTTTGCC

HaeIV                       CviRI
                                    Hin4I       SfaNI   NlaIII  |
        MseI                        |           |       |       |
        |                           |           |       |       |
        TGCTACCTTAAATGTTCATAACTTCACGCAAGATGAAAAGTCCGTCGTCATCATGGATGC
1621    ---------+---------+---------+---------+---------+---------+ 1680
        ACGATGGAATTTACAAGTATTGAAGTGCGTTCTACTTTTCAGGCAGCAGTAGTACCTACG

FokI
        CjeI |
    NlaIV   ||                              TaaI
    AvaII|  ||                  AluI        HphI|
    Sau96I| ||       BsmFI      CviJI       CjeI ||          MseI
    ||      ||       |          |           |   ||           |
        AGGGACCACATTAGCAACTACAAATGGAGCTAATAATACTGACGGTGCTATCACCTTAAA
1681    ---------+---------+---------+---------+---------+---------+ 1740
        TCCCTGGTGTAATCGTTGATGTTTACCTCGATTATTATGACTGCCACGATAGTGGAATTT

CviJI
                                                Fnu4HI |
        AluI            HinfI                   TauI   |
        CviJI           TfiI                    AciI|  |   CjePI CjePI
    HindIII |           Hpy178III |   BccI      FokI|  |   MseI| CviRI
    ||                  ||            |         |||      ||        |
        CAAGCTTGTAATCAATCTGGATTCTTTGGATGGCACTAAAGCGGCTGTCGTTAATGTCA
1741    ---------+---------+---------+---------+---------+---------+ 1800
        GTTCGAACATTAGTTAGACCTAAGAAACCTACCGTGATTTCGCCGACAGCAATTACACGT
```

FIG. 2I

```
                 BsgI
           BanII|         CjePI
           BsiHKAI|   Hpy178III    |
           Bsp1286I|      MspI|    |
               SacI|    BsaWI||    |
               AluI||   BspEI||    |                    Hpy178III
       RsaI    CviJI||   CjePI|||  |    Bce83I              SmlI    |
        |      |  || |    |||| |   |       |                  |    |
        GAGTACCAATGGAGCTCTCACTATATCCGGAACTTTAGGACTTGTGAAAAACTCTCAAGA
1801    ---------+---------+---------+---------+---------+---------+ 1860
        CTCATGGTTACCTCGAGAGTGATATAGGCCTTGAAATCCTGAACACTTTTTGAGAGTTCT

Sth132I
      MaeIII  |         BscGI
      Tsp45I  |  BsaJI    |
       CjeI|  |BstDSI     |   MseI    FokI    CjeI  Hpy188IX
        || |  |  |        |    |       |       |       |
        TTGCTGTGACAACCACGGGATGTTTAATAAAGATTTACAGCAAGTTCCGATTTTAGAACT
1861    ---------+---------+---------+---------+---------+---------+ 1920
        AACGACACTGTTGGTGCCCTACAAATTATTTCTAAATGTCGTTCAAGGCTAAAATCTTGA

Eco57I
               MaeIII                                      CviJI
                 TaaI          PshAI    BsmAI    MwoI        |
                  |              |        |        |   |  |
        CAAAGCGACTTCAAATACTGTAACCACTACGGACTTCAGTCTCGGCACAAACGGCTATCA
1921    ---------+---------+---------+---------+---------+---------+ 1980
        GTTTCGCTGAAGTTTATGACATTGGTGATGCCTGAAGTCAGAGCCGTGTTTGCCGATAGT

BcefI
            |
        GCAATCTCCCTATGGGTATCAAGGAACTTGGGAGTTTACCATAGACACGACAACCCATAC
1981    ---------+---------+---------+---------+---------+---------+ 2040
        CGTTAGAGGGATACCCATAGTTCCTTGAACCCTCAAATGGTATCTGTGCTGTTGGGTATG
```

FIG. 2J

```
                       FokI             MnlI
                       MspI          Hpy178III
                       BsaWI|           MspI|
    MaeIII             BsrFI|           BsaWI||
     TaaI              MboII|           BspEI||
    Tsp45I  Tsp509I    PinAI|      HgaI      |||
         |      |         ||         |       |||
          GGTCACAGGAAATTGGAAAAAAACCGGTTATCTTCCTCATCCGGAGCGTCTTGCTCCCCT
     2041 ---------+---------+---------+---------+---------+---------+ 2100
          CCAGTGTCCTTTAACCTTTTTTTGGCCAATAGAAGGAGTAGGCCTCGCAGAACGAGGGGA

HgaI            Fnu4HI
                   CviJI         AceIII          AluI|            MwoI|
           MnlI      |           MaeII |          CviJI|          TseI|
             |       |              |  |              ||              ||
           CATTCCTAATAGCCTATGGGCAAACGTCATAGATTTACGAGCTGTAAGTCAAGCGTCAGC
     2101 ---------+---------+---------+---------+---------+---------+ 2160
          GTAAGGATTATCGGATACCCGTTTGCAGTATCTAAATGCTCGACATTCAGTTCGCAGTCG

AluI           BseMII
           AlwNI          MboII                            ApoI
           BsmFI          ScrFI |                          Tsp509I
           CviJI          BsaJI|                             MboII  |
           MspA1I   BbvI  BsaJI||                       SfaNI       |
           PvuII BccI  |  EcoRII||    DdeI    Tsp509I      |        |
             |    |    |     |||       |          |        |       |
          AGCTGATGGCGAAGATGTCCCTGGGAAGCAACTGAGCATCACAGGAATTACAAATTTCTT
     2161 ---------+---------+---------+---------+---------+---------+ 2220
          TCGACTACCGCTTCTACAGGGACCCTTCGTTGACTCGTAGTGTCCTTAATGTTTAAAGAA
```

FIG. 2K

```
                              AciI
            MslI              MwoI|
            MspI              TaqII||
           BsaWI|             AluI |||
           BsrFI|             CviJI|||        BstXI
           PinAI|             HphI |||        MslI |
      SfaNI    ||           Fnu4HI||  |||    MnlI|  |
     HinfI |   ||            TseI |||  |||   BslI|| |
      TfiI |   ||            Cac8I|||| |||   BbvI||| |    Hin4I
    NlaIII |  |   ||         CviRI |  |||| |||  NdeI||||  |    CviJI|
        | |   ||              |   ||||  |||    ||||  |      ||
        CCATGCGAATCATACCGGTGATGCACGCAGCTACCGCCATATGGGTGGAGGCTACCTCAT
2221    ---------+---------+---------+---------+---------+---------+ 2280
        GGTACGCTTAGTATGGCCACTACGTGCGTCGATGGCGGTATACCCACCTCCGATGGAGTA Hpy178III                              AluI
                 BbvI     |Fnu4HI                            CviJI
          BpmI   SfaNI    |AlwNI|                           MspA1I
         MnlI|   BplI   |  SfaNI TseI|  MseI    BfaI         PvuII
          ||    |       |     |    ||    |       |            |
        CAATACCTACACACGCATCACTCCAGATGCTGCGTTAAGTCTAGGTTTTGGACAGCTGTT
2281    ---------+---------+---------+---------+---------+---------+ 2340
        GTTATGGATGTGTGCGTAGTGAGGTCTACGACGCAATTCAGATCCAAAACCTGTCGACAA TaaI
                          MnlI    |
                        MaeIII    |                              AccI
                        Tsp45I    |         AclI                 TaaI |
            DdeI       Pfl1108I   |  |     MaeII        SfcI      | |
             |           |   ||   |  |        |           |       | |
        TACAAAATCTAAGGATTACCTCGTAGGTCACGGTCATTCTAACGTTTATTTCGCTACAGT
2341    ---------+---------+---------+---------+---------+---------+ 2400
        ATGTTTTAGATTCCTAATGGAGCATCCAGTGCCAGTAAGATTGCAAATAAAGCGATGTCA
```

FIG. 2L

```
                              HinfI
                               TfiI
                              AlwI |
                          Hpy178III |
                             TaqI | |
                             MboII| |                              AvaI
                           DpnI  | | |    Hpy178III               BseMII
         HphI           Sau3AI |  | | |    DdeI |                  SmlI
    BstZ17I |  Tth111II   BsmAI | || | |   MnlI |                   XhoI
       | |     |            |   | || | |    | |  |                   |
       ATACTCTAACATCACCAAGTCTCTGTTTGGATCATCGAGATTCTTCTCAGGAGGCACTTC
  2401 ---------+---------+---------+---------+---------+---------+ 2460
       TATGAGATTGTAGTGGTTCAGAGACAAACCTAGTAGCTCTAAGAAGAGTCCTCCGTGAAG MaeIII
         BcefI  |
     Hpy178III  |       CviJI                                      BbvI
         TaqI  |  SfcI   |        BsrDI                     Tsp509I |
          | |    |   |   |          |                         | |
         TCGAGTTACCTATAGCCGTAGCAATGAGAAAGTAAAGACTTCATATACAAAATTGCCTAA
    2461 ---------+---------+---------+---------+---------+---------+ 2520
         AGCTCAATGGATATCGGCATCGTTACTCTTTCATTTCTGAAGTATATGTTTTAACGGATT Fnu4HI        MunI
            HaeII       Tsp509I
       BglI HhaI|   MaeIII  |              CjeI              MboII
       MwoI TseI|CjeI |      |        TaqI     |NlaIV        BccI |
         |   ||   |   |      |         |       |  |           | |
         AGGGCGCTGCTCTTGGAGTAACAATTGCTGGTTAGGAGAACTCGAAGGGAACCTTCCCAT
    2521 ---------+---------+---------+---------+---------+---------+ 2580
         TCCCGCGACGAGAACCTCATTGTTAACGACCAATCCTCTTGAGCTTCCCTTGGAAGGGTA SmlI      DpnI
             EarI        SfaNI |    MnlI            AluI
           Bce83I |  MseI  |   | Sau3AI |  Tth111II CviJI  MwoI
             | |     |     | |   | |    |     |      |     |
          CACTCTCTCTTCTCGCATCTTAAACCTCAAGCAGATCATTCCCTTTGTAAAAGCTGAAGT
     2581 ---------+---------+---------+---------+---------+---------+ 2640
          GTGAGAGAGAAGAGCGTAGAATTTGGAGTTCGTCTAGTAAGGGAAACATTTTCGACTTCA
```

FIG. 2M

```
                                                     BslI
                                                  Sth132I
                                                     BslI  |
                                                  BsaJI    |  |
                     NlaIII                         MnlI   |  |
                   Eco57I   |                       AvaI|  |  |
             HinfI       |  |                       CjePI|| |  |
             FokI |      |  |                        MnlI || |  |
             ThaI |      |  |                                 |  |
             PleI |      |  |        SfaNI          |    ||| |  |           Tth111I
               |  |      |  |          |            |    ||| |  |             |
             TGCTTACGCGACTCATGGGGGCATCCAAGAAAATACCCCCGAGGGGAGGATTTTTGGACA
      2641   ---------+---------+---------+---------+---------+---------+   2700
             ACGAATGCGCTGAGTACCCCCGTAGGTTCTTTTATGGGGGCTCCCCTCCTAAAAACCTGT AclI            BsaHI
                          MaeII      HgaI   Sth132I              ApoI
              TaaI    CjePI    |CviRI |BscGI     |AciI       Tsp509I
                |       |      |   |  |   |      |   |         |
             CGGTCATCTACTCAACGTTGCAGTTCCCGTAGGCGTCCGCTTTGGTAAAAATTCTCATAA
      2701   ---------+---------+---------+---------+---------+---------+   2760
             GCCAGTAGATGAGTTGCAACGTCAAGGGCATCCGCAGGCGAAACCATTTTTAAGAGTATT MaeIII
                                CviJI                      Tsp45I
             TaqI            Pfl1108I |  Hpy178III  BsaBI    |     Hpy178III
               |                |   |  |     |         |     |         |
             TCGACCAGATTTTTACACTATAATCGTAGCCTATGCTCCTGATGTCTATCGTCACAATCC
      2761   ---------+---------+---------+---------+---------+---------+   2820
             AGCTGGTCTAAAAATGTGATATTAGCATCGGATACGAGGACTACAGATAGCAGTGTTAGG AvaII
                                             Sau96I
                                           BsaAI  |
                             BslI        MaeII|   |
                      MseI    |   AluI      ||    |    BslI
                      VspI |  |  CviJI      ||    |    SfcI  |MnlI
                        | |   |    |  ||    ||    |     |    |  |
             TGATTGCGATACGACATTACCTATTAATGGAGCTACGTGGACCTCTATAGGGAATAATCT
      2821   ---------+---------+---------+---------+---------+---------+   2880
             ACTAACGCTATGCTGTAATGGATAATTACCTCGATGCACCTGGAGATATCCCTTATTAGA
```

FIG. 2N

```
                                                                    BglII
                                                                    BstYI
                                                                    Sau3AI
                                                                    Sth132I  |
              FokI        Eco57I                                    Hpy178III| |
          RsaI    |   RsaI    |       Tth111II                      BfaI | | |
          ScaI    |   TatI    |       SfaNI      |                  MboII| | |
          TatI    |  |BfaI | |        CviJI      |                  XbaI | | |
           |      |  | |  | |          |         |                   |||||
          AACCAGAAGTACTTTGCTAGTACAAGCATCCAGCCATACTTCAGTAAATGATGTTCTAGA
     2881 ---------+---------+---------+---------+---------+---------+ 2940
          TTGGTCTTCATGAAACGATCATGTTCGTAGGTCGGTATGAAGTCATTTACTACAAGATCT

TspRI
                TaaI   |                                        Hpy178III
           Bsp1286I |  |                                 MnlI       |
                BmgI|  |                                 Sth132I  BfaI|
          DpnI  BseSI| | |        FokI        BscGI            |  XbaI||
           |    | | | | |          |           |               |   |||
          GATCTTCGGGCACTGTGGATGTGATATTCGCAGAACCTCCCGTAAATATACTCTAGATAT
     2941 ---------+---------+---------+---------+---------+---------+ 3000
          CTAGAAGCCCGTGACACCTACACTATAAGCGTCTTGGAGGGCATTTATATGAGATCTATA

NlaIII
                                                         NspI
                      DraI                               SphI
          Tsp509I     MseI|     MseI      MnlI         Cac8I  |      MboII
             |         ||           |        |           |    |        |
          AGGAAGCAAATTACGATTTTAAACCTTATTTAACGACAGGGTTGAGGCATGCCTCTTTCT
     3001 ---------+---------+---------+---------+---------+---------+ 3060
          TCCTTCGTTTAATGCTAAAATTTGGAATAAATTGCTGTCCCAACTCCGTACGGAGAAAGA
```

FIG. 2O

```
                                                          BsmAI
                                                   HhaI    |
                                                   ThaI    |
                                             BseMII |      |
      MnlI              AccI           CviRI   MwoI| |     |DdeI
       |                 |               |      |  |||     | |
      TTCAAATCTTCATCTTTTTGTCTACTTGCCTGTTTATGTAGTGCAAGTTGCGCGTTTGCT
3061  ---------+---------+---------+---------+---------+---------+  3120
      AAGTTTAGAAGTAGAAAAACAGATGAACGGACAAATACATCACGTTCAACGCGCAAACGA

Hpy188IX
       HinfI    |
       MnlI|    |
      BfaI ||   |
     PleI | ||  |
      |   | ||  |
      GAGACTAGACTCGGAGGGAACTTTGTTCCT
3121  ---------+---------+---------+  3150
      CTCTGATCTGAGCCTCCCTTGAAACAAGGA
```

FIG. 2P

SEQUENCE LISTING

```
<160> NUMBER OF SEQ ID NOS: 4

<210> SEQ ID NO 1
<211> LENGTH: 3150
<212> TYPE: DNA
<213> ORGANISM: Chlamydia pneumoniae
<220> FEATURE:
<221> NAME/KEY: CDS
<222> LOCATION: (101)..(3019)

<400> SEQUENCE: 1
gctgtcaaaa ttaagagatt aaaactgtgt cttattgtac ttgttttttt acagcctttc      60
ccttatttgt aggataatct ggtttcatct ctacgtgcaa atg aaa acg tct att     115
                                             Met Lys Thr Ser Ile
                                               1               5 cgt aag ttc tta att tct acc aca ctg gcg cca tgt ttt gct tca aca    163
Arg Lys Phe Leu Ile Ser Thr Thr Leu Ala Pro Cys Phe Ala Ser Thr
             10                  15                  20 gcg ttt act gta gaa gtt atc atg cct tcc gag aac ttt gat gga tcg    211
Ala Phe Thr Val Glu Val Ile Met Pro Ser Glu Asn Phe Asp Gly Ser
         25                  30                  35 agt ggg aag att ttt cct tac aca aca ctt tct gat cct aga ggg aca    259
Ser Gly Lys Ile Phe Pro Tyr Thr Thr Leu Ser Asp Pro Arg Gly Thr
     40                  45                  50 ctc tgt att ttt tca ggg gat ctc tac att gcg aat ctt gat aat gcc    307
Leu Cys Ile Phe Ser Gly Asp Leu Tyr Ile Ala Asn Leu Asp Asn Ala
 55                  60                  65 ata tcc aga acc tct tcc agt tgc ttt agc aat agg gcg gga gca cta    355
```

| | | |
|---|---|---|
| Ile Ser Arg Thr Ser Ser Ser Cys Phe Ser Asn Arg Ala Gly Ala Leu<br>70                 75                80                  85 | | |
| caa atc tta gga aaa ggt ggg gtt ttc tcc ttc tta aat atc cgt tct<br>Gln Ile Leu Gly Lys Gly Gly Val Phe Ser Phe Leu Asn Ile Arg Ser<br>                90                        95                     100 | 403 |
| tca gct gac gga gcc gcg att agt agt gta atc acc caa aat cct gaa<br>Ser Ala Asp Gly Ala Ala Ile Ser Ser Val Ile Thr Gln Asn Pro Glu<br>            105                    110                  115 | 451 |
| cta tgt ccc ttg agt ttt tca gga ttt agt cag atg atc ttc gat aac<br>Leu Cys Pro Leu Ser Phe Ser Gly Phe Ser Gln Met Ile Phe Asp Asn<br>       120                    125                  130 | 499 |
| tgt gaa tct ttg act tca gat acc tca gcg agt aat gtc ata cct cac<br>Cys Glu Ser Leu Thr Ser Asp Thr Ser Ala Ser Asn Val Ile Pro His<br>135                     140                  145 | 547 |
| gca tcg gcg att tac gct aca acg ccc atg ctc ttt aca aac aat gac<br>Ala Ser Ala Ile Tyr Ala Thr Thr Pro Met Leu Phe Thr Asn Asn Asp<br>150                     155                  160               165 | 595 |
| tcc ata cta ttc caa tac aac cgt tct gca gga ttt gga gct gcc att<br>Ser Ile Leu Phe Gln Tyr Asn Arg Ser Ala Gly Phe Gly Ala Ala Ile<br>                170                  175                  180 | 643 |
| cga ggc aca agc atc aca ata gaa aat acg aaa aag agc ctt ctc ttt<br>Arg Gly Thr Ser Ile Thr Ile Glu Asn Thr Lys Lys Ser Leu Leu Phe<br>           185                    190                  195 | 691 |
| aat ggt aat gga tcc atc tct aat gga ggg gcc ctc acg gga tct gca<br>Asn Gly Asn Gly Ser Ile Ser Asn Gly Gly Ala Leu Thr Gly Ser Ala<br>                200                  205                  210 | 739 |
| gcg atc aac ctc atc aac aat agc gct cct gtg att ttc tca acg aat<br>Ala Ile Asn Leu Ile Asn Asn Ser Ala Pro Val Ile Phe Ser Thr Asn<br>       215                    220                  225 | 787 |
| gct aca ggg atc tat ggt ggg gct att tac ctt acc gga gga tct atg<br>Ala Thr Gly Ile Tyr Gly Gly Ala Ile Tyr Leu Thr Gly Gly Ser Met<br>230                     235                  240               245 | 835 |
| ctc acc tct ggg aac ctc tca gga gtc ttg ttc gtt aat aat agc tcg<br>Leu Thr Ser Gly Asn Leu Ser Gly Val Leu Phe Val Asn Asn Ser Ser<br>                250                  255                  260 | 883 |
| cgc tca gga ggc gct atc tat gct aac gga aat gtc aca ttt tct aat<br>Arg Ser Gly Gly Ala Ile Tyr Ala Asn Gly Asn Val Thr Phe Ser Asn<br>           265                    270                  275 | 931 |
| aac agc gac ctg act ttc caa aac aat aca gca tct cca caa aac tcc<br>Asn Ser Asp Leu Thr Phe Gln Asn Asn Thr Ala Ser Pro Gln Asn Ser<br>                280                  285                  290 | 979 |
| tta cct gca cct aca cct cca cct aca cca cca gca gtc act cct ttg<br>Leu Pro Ala Pro Thr Pro Pro Pro Thr Pro Pro Ala Val Thr Pro Leu<br>295                     300                  305 | 1027 |
| tta gga tat gga ggc gcc atc ttc tgt act cct cca gct acc ccc cca<br>Leu Gly Tyr Gly Gly Ala Ile Phe Cys Thr Pro Pro Ala Thr Pro Pro<br>310                     315                  320               325 | 1075 |
| cca aca ggt gtt agc ctg act ata tct gga gaa aac agc gtt aca ttc<br>Pro Thr Gly Val Ser Leu Thr Ile Ser Gly Glu Asn Ser Val Thr Phe<br>                330                  335                  340 | 1123 |
| cta gaa aac att gcc tcc gaa caa gga gga gcc ctc tat ggc aaa aag<br>Leu Glu Asn Ile Ala Ser Glu Gln Gly Gly Ala Leu Tyr Gly Lys Lys<br>           345                    350                  355 | 1171 |
| atc tct ata gat tct aat aaa tct aca ata ttt ctt gga aat aca gct<br>Ile Ser Ile Asp Ser Asn Lys Ser Thr Ile Phe Leu Gly Asn Thr Ala<br>                360                  365                  370 | 1219 |
| gga aaa gga ggc gct att gct att ccc gaa tct ggg gag ctc tct cta<br>Gly Lys Gly Gly Ala Ile Ala Ile Pro Glu Ser Gly Glu Leu Ser Leu<br>375                     380                  385 | 1267 |

```
                                                     -continued tcc gca aat caa ggt gat atc ctc ttt aac aag aac ctc agc atc act    1315
Ser Ala Asn Gln Gly Asp Ile Leu Phe Asn Lys Asn Leu Ser Ile Thr
390                 395                 400                 405 agt ggg aca cct act cgc aat agt att cac ttc gga aaa gat gcc aag    1363
Ser Gly Thr Pro Thr Arg Asn Ser Ile His Phe Gly Lys Asp Ala Lys
            410                 415                 420 ttt gcc act cta ggg aat acg caa ggc tat acc cta tac ttc tat gat    1411
Phe Ala Thr Leu Gly Asn Thr Gln Gly Tyr Thr Leu Tyr Phe Tyr Asp
        425                 430                 435 ccg att aca tct gat gat tta tct gct gca tcc gca gcc gct act gtg    1459
Pro Ile Thr Ser Asp Asp Leu Ser Ala Ala Ser Ala Ala Ala Thr Val
    440                 445                 450 gtc gtc aat ccc aaa gcc agt gca gat ggt gcg tat tca ggg act att    1507
Val Val Asn Pro Lys Ala Ser Ala Asp Gly Ala Tyr Ser Gly Thr Ile
455                 460                 465 gtc ttt tca gga gaa acc ctc act gct acc gaa gca gca acc cct gca    1555
Val Phe Ser Gly Glu Thr Leu Thr Ala Thr Glu Ala Ala Thr Pro Ala
470                 475                 480                 485 aat gct aca tct aca tta aac caa aag cta gaa ctt gaa ggc ggt act    1603
Asn Ala Thr Ser Thr Leu Asn Gln Lys Leu Glu Leu Glu Gly Gly Thr
            490                 495                 500 ctc gct tta aga aac ggt gct acc tta aat gtt cat aac ttc acg caa    1651
Leu Ala Leu Arg Asn Gly Ala Thr Leu Asn Val His Asn Phe Thr Gln
        505                 510                 515 gat gaa aag tcc gtc gtc atc atg gat gca ggg acc aca tta gca act    1699
Asp Glu Lys Ser Val Val Ile Met Asp Ala Gly Thr Thr Leu Ala Thr
    520                 525                 530 aca aat gga gct aat aat act gac ggt gct atc acc tta aac aag ctt    1747
Thr Asn Gly Ala Asn Asn Thr Asp Gly Ala Ile Thr Leu Asn Lys Leu
535                 540                 545 gta atc aat ctg gat tct ttg gat ggc act aaa gcg gct gtc gtt aat    1795
Val Ile Asn Leu Asp Ser Leu Asp Gly Thr Lys Ala Ala Val Val Asn
550                 555                 560                 565 gtg cag agt acc aat gga gct ctc act ata tcc gga act tta gga ctt    1843
Val Gln Ser Thr Asn Gly Ala Leu Thr Ile Ser Gly Thr Leu Gly Leu
            570                 575                 580 gtg aaa aac tct caa gat tgc tgt gac aac cac ggg atg ttt aat aaa    1891
Val Lys Asn Ser Gln Asp Cys Cys Asp Asn His Gly Met Phe Asn Lys
        585                 590                 595 gat tta cag caa gtt ccg att tta gaa ctc aaa gcg act tca aat act    1939
Asp Leu Gln Gln Val Pro Ile Leu Glu Leu Lys Ala Thr Ser Asn Thr
    600                 605                 610 gta acc act acg gac ttc agt ctc ggc aca aac ggc tat cag caa tct    1987
Val Thr Thr Thr Asp Phe Ser Leu Gly Thr Asn Gly Tyr Gln Gln Ser
615                 620                 625 ccc tat ggg tat caa gga act tgg gag ttt acc ata gac acg aca acc    2035
Pro Tyr Gly Tyr Gln Gly Thr Trp Glu Phe Thr Ile Asp Thr Thr Thr
630                 635                 640                 645 cat acg gtc aca gga aat tgg aaa aaa acc ggt tat ctt cct cat ccg    2083
His Thr Val Thr Gly Asn Trp Lys Lys Thr Gly Tyr Leu Pro His Pro
            650                 655                 660 gag cgt ctt gct ccc ctc att cct aat agc cta tgg gca aac gtc ata    2131
Glu Arg Leu Ala Pro Leu Ile Pro Asn Ser Leu Trp Ala Asn Val Ile
        665                 670                 675 gat tta cga gct gta agt caa gcg tca gca gct gat ggc gaa gat gtc    2179
Asp Leu Arg Ala Val Ser Gln Ala Ser Ala Ala Asp Gly Glu Asp Val
    680                 685                 690 cct ggg aag caa ctg agc atc aca gga att aca aat ttc ttc cat gcg    2227
Pro Gly Lys Gln Leu Ser Ile Thr Gly Ile Thr Asn Phe Phe His Ala
695                 700                 705
```

```
aat cat acc ggt gat gca cgc agc tac cgc cat atg ggt gga ggc tac      2275
Asn His Thr Gly Asp Ala Arg Ser Tyr Arg His Met Gly Gly Gly Tyr
710             715                 720                 725 ctc atc aat acc tac aca cgc atc act cca gat gct gcg tta agt cta      2323
Leu Ile Asn Thr Tyr Thr Arg Ile Thr Pro Asp Ala Ala Leu Ser Leu
            730                 735                 740 ggt ttt gga cag ctg ttt aca aaa tct aag gat tac ctc gta ggt cac      2371
Gly Phe Gly Gln Leu Phe Thr Lys Ser Lys Asp Tyr Leu Val Gly His
        745                 750                 755 ggt cat tct aac gtt tat ttc gct aca gta tac tct aac atc acc aag      2419
Gly His Ser Asn Val Tyr Phe Ala Thr Val Tyr Ser Asn Ile Thr Lys
    760                 765                 770 tct ctg ttt gga tca tcg aga ttc ttc tca gga ggc act tct cga gtt      2467
Ser Leu Phe Gly Ser Ser Arg Phe Phe Ser Gly Gly Thr Ser Arg Val
775                 780                 785 acc tat agc cgt agc aat gag aaa gta aag act tca tat aca aaa ttg      2515
Thr Tyr Ser Arg Ser Asn Glu Lys Val Lys Thr Ser Tyr Thr Lys Leu
790                 795                 800                 805 cct aaa ggg cgc tgc tct tgg agt aac aat tgc tgg tta gga gaa ctc      2563
Pro Lys Gly Arg Cys Ser Trp Ser Asn Asn Cys Trp Leu Gly Glu Leu
                810                 815                 820 gaa ggg aac ctt ccc atc act ctc tct tct cgc atc tta aac ctc aag      2611
Glu Gly Asn Leu Pro Ile Thr Leu Ser Ser Arg Ile Leu Asn Leu Lys
            825                 830                 835 cag atc att ccc ttt gta aaa gct gaa gtt gct tac gcg act cat ggg      2659
Gln Ile Ile Pro Phe Val Lys Ala Glu Val Ala Tyr Ala Thr His Gly
        840                 845                 850 ggc atc caa gaa aat acc ccc gag ggg agg att ttt gga cac ggt cat      2707
Gly Ile Gln Glu Asn Thr Pro Glu Gly Arg Ile Phe Gly His Gly His
    855                 860                 865 cta ctc aac gtt gca gtt ccc gta ggc gtc cgc ttt ggt aaa aat tct      2755
Leu Leu Asn Val Ala Val Pro Val Gly Val Arg Phe Gly Lys Asn Ser
870                 875                 880                 885 cat aat cga cca gat ttt tac act ata atc gta gcc tat gct cct gat      2803
His Asn Arg Pro Asp Phe Tyr Thr Ile Ile Val Ala Tyr Ala Pro Asp
                890                 895                 900 gtc tat cgt cac aat cct gat tgc gat acg aca tta cct att aat gga      2851
Val Tyr Arg His Asn Pro Asp Cys Asp Thr Thr Leu Pro Ile Asn Gly
            905                 910                 915 gct acg tgg acc tct ata ggg aat aat cta acc aga agt act ttg cta      2899
Ala Thr Trp Thr Ser Ile Gly Asn Asn Leu Thr Arg Ser Thr Leu Leu
        920                 925                 930 gta caa gca tcc agc cat act tca gta aat gat gtt cta gag atc ttc      2947
Val Gln Ala Ser Ser His Thr Ser Val Asn Asp Val Leu Glu Ile Phe
    935                 940                 945 ggg cac tgt gga tgt gat att cgc aga acc tcc cgt aaa tat act cta      2995
Gly His Cys Gly Cys Asp Ile Arg Arg Thr Ser Arg Lys Tyr Thr Leu
950                 955                 960                 965 gat ata gga agc aaa tta cga ttt taaaccttat ttaacgacag ggttgaggca     3049
Asp Ile Gly Ser Lys Leu Arg Phe
                970 tgcctctttc tttcaaatct tcatcttttt gtctacttgc ctgtttatgt agtgcaagtt   3109 gcgcgtttgc tgagactaga ctcggaggga actttgttcc t                        3150

<210> SEQ ID NO 2
<211> LENGTH: 973
<212> TYPE: PRT
<213> ORGANISM: Chlamydia pneumoniae
```

```
<400> SEQUENCE: 2

Met Lys Thr Ser Ile Arg Lys Phe Leu Ile Ser Thr Thr Leu Ala Pro
 1               5                  10                  15

Cys Phe Ala Ser Thr Ala Phe Thr Val Glu Val Ile Met Pro Ser Glu
                20                  25                  30

Asn Phe Asp Gly Ser Ser Gly Lys Ile Phe Pro Tyr Thr Thr Leu Ser
            35                  40                  45

Asp Pro Arg Gly Thr Leu Cys Ile Phe Ser Gly Asp Leu Tyr Ile Ala
        50                  55                  60

Asn Leu Asp Asn Ala Ile Ser Arg Thr Ser Ser Ser Cys Phe Ser Asn
65                  70                  75                  80

Arg Ala Gly Ala Leu Gln Ile Leu Gly Lys Gly Val Phe Ser Phe
                85                  90                  95

Leu Asn Ile Arg Ser Ser Ala Asp Gly Ala Ala Ile Ser Ser Val Ile
                100                 105                 110

Thr Gln Asn Pro Glu Leu Cys Pro Leu Ser Phe Ser Gly Phe Ser Gln
            115                 120                 125

Met Ile Phe Asp Asn Cys Glu Ser Leu Thr Ser Asp Thr Ser Ala Ser
        130                 135                 140

Asn Val Ile Pro His Ala Ser Ala Ile Tyr Ala Thr Thr Pro Met Leu
145                 150                 155                 160

Phe Thr Asn Asn Asp Ser Ile Leu Phe Gln Tyr Asn Arg Ser Ala Gly
                165                 170                 175

Phe Gly Ala Ala Ile Arg Gly Thr Ser Ile Thr Ile Glu Asn Thr Lys
                180                 185                 190

Lys Ser Leu Leu Phe Asn Gly Asn Gly Ser Ile Ser Asn Gly Gly Ala
            195                 200                 205

Leu Thr Gly Ser Ala Ala Ile Asn Leu Ile Asn Asn Ser Ala Pro Val
        210                 215                 220

Ile Phe Ser Thr Asn Ala Thr Gly Ile Tyr Gly Gly Ala Ile Tyr Leu
225                 230                 235                 240

Thr Gly Gly Ser Met Leu Thr Ser Gly Asn Leu Ser Gly Val Leu Phe
                245                 250                 255

Val Asn Asn Ser Ser Arg Ser Gly Gly Ala Ile Tyr Ala Asn Gly Asn
                260                 265                 270

Val Thr Phe Ser Asn Asn Ser Asp Leu Thr Phe Gln Asn Asn Thr Ala
            275                 280                 285

Ser Pro Gln Asn Ser Leu Pro Ala Pro Thr Pro Pro Thr Pro Pro
        290                 295                 300

Ala Val Thr Pro Leu Leu Gly Tyr Gly Gly Ala Ile Phe Cys Thr Pro
305                 310                 315                 320

Pro Ala Thr Pro Pro Thr Gly Val Ser Leu Thr Ile Ser Gly Glu
                325                 330                 335

Asn Ser Val Thr Phe Leu Glu Asn Ile Ala Ser Glu Gln Gly Gly Ala
                340                 345                 350

Leu Tyr Gly Lys Lys Ile Ser Ile Asp Ser Asn Lys Ser Thr Ile Phe
            355                 360                 365

Leu Gly Asn Thr Ala Gly Lys Gly Gly Ala Ile Ala Ile Pro Glu Ser
        370                 375                 380

Gly Glu Leu Ser Leu Ser Ala Asn Gln Gly Asp Ile Leu Phe Asn Lys
385                 390                 395                 400

Asn Leu Ser Ile Thr Ser Gly Thr Pro Thr Arg Asn Ser Ile His Phe
                405                 410                 415
```

Gly Lys Asp Ala Lys Phe Ala Thr Leu Gly Asn Thr Gln Gly Tyr Thr
            420                 425                 430

Leu Tyr Phe Tyr Asp Pro Ile Thr Ser Asp Asp Leu Ser Ala Ala Ser
        435                 440                 445

Ala Ala Ala Thr Val Val Asn Pro Lys Ala Ser Ala Asp Gly Ala
    450                 455                 460

Tyr Ser Gly Thr Ile Val Phe Ser Gly Glu Thr Leu Thr Ala Thr Glu
465                 470                 475                 480

Ala Ala Thr Pro Ala Asn Ala Thr Ser Thr Leu Asn Gln Lys Leu Glu
            485                 490                 495

Leu Glu Gly Gly Thr Leu Ala Leu Arg Asn Gly Ala Thr Leu Asn Val
            500                 505                 510

His Asn Phe Thr Gln Asp Glu Lys Ser Val Val Ile Met Asp Ala Gly
            515                 520                 525

Thr Thr Leu Ala Thr Thr Asn Gly Ala Asn Asn Thr Asp Gly Ala Ile
            530                 535                 540

Thr Leu Asn Lys Leu Val Ile Asn Leu Asp Ser Leu Asp Gly Thr Lys
545                 550                 555                 560

Ala Ala Val Val Asn Val Gln Ser Thr Asn Gly Ala Leu Thr Ile Ser
            565                 570                 575

Gly Thr Leu Gly Leu Val Lys Asn Ser Gln Asp Cys Cys Asp Asn His
            580                 585                 590

Gly Met Phe Asn Lys Asp Leu Gln Gln Val Pro Ile Leu Glu Leu Lys
            595                 600                 605

Ala Thr Ser Asn Thr Val Thr Thr Thr Asp Phe Ser Leu Gly Thr Asn
            610                 615                 620

Gly Tyr Gln Gln Ser Pro Tyr Gly Tyr Gln Gly Thr Trp Glu Phe Thr
625                 630                 635                 640

Ile Asp Thr Thr Thr His Thr Val Thr Gly Asn Trp Lys Lys Thr Gly
                645                 650                 655

Tyr Leu Pro His Pro Glu Arg Leu Ala Pro Leu Ile Pro Asn Ser Leu
            660                 665                 670

Trp Ala Asn Val Ile Asp Leu Arg Ala Val Ser Gln Ala Ser Ala Ala
            675                 680                 685

Asp Gly Glu Asp Val Pro Gly Lys Gln Leu Ser Ile Thr Gly Ile Thr
            690                 695                 700

Asn Phe Phe His Ala Asn His Thr Gly Asp Ala Arg Ser Tyr Arg His
705                 710                 715                 720

Met Gly Gly Gly Tyr Leu Ile Asn Thr Tyr Thr Arg Ile Thr Pro Asp
            725                 730                 735

Ala Ala Leu Ser Leu Gly Phe Gly Gln Leu Phe Thr Lys Ser Lys Asp
            740                 745                 750

Tyr Leu Val Gly His Gly His Ser Asn Val Tyr Phe Ala Thr Val Tyr
            755                 760                 765

Ser Asn Ile Thr Lys Ser Leu Phe Gly Ser Ser Arg Phe Phe Ser Gly
            770                 775                 780

Gly Thr Ser Arg Val Thr Tyr Ser Arg Ser Asn Glu Lys Val Lys Thr
785                 790                 795                 800

Ser Tyr Thr Lys Leu Pro Lys Gly Arg Cys Ser Trp Ser Asn Asn Cys
            805                 810                 815

Trp Leu Gly Glu Leu Glu Gly Asn Leu Pro Ile Thr Leu Ser Ser Arg
            820                 825                 830

-continued

```
Ile Leu Asn Leu Lys Gln Ile Ile Pro Phe Val Lys Ala Glu Val Ala
        835                 840                 845

Tyr Ala Thr His Gly Gly Ile Gln Glu Asn Thr Pro Glu Gly Arg Ile
    850                 855                 860

Phe Gly His Gly His Leu Leu Asn Val Ala Val Pro Val Gly Val Arg
865                 870                 875                 880

Phe Gly Lys Asn Ser His Asn Arg Pro Asp Phe Tyr Thr Ile Ile Val
                885                 890                 895

Ala Tyr Ala Pro Asp Val Tyr Arg His Asn Pro Asp Cys Asp Thr Thr
            900                 905                 910

Leu Pro Ile Asn Gly Ala Thr Trp Thr Ser Ile Gly Asn Asn Leu Thr
        915                 920                 925

Arg Ser Thr Leu Leu Val Gln Ala Ser Ser His Thr Ser Val Asn Asp
    930                 935                 940

Val Leu Glu Ile Phe Gly His Cys Gly Cys Asp Ile Arg Arg Thr Ser
945                 950                 955                 960

Arg Lys Tyr Thr Leu Asp Ile Gly Ser Lys Leu Arg Phe
                965                 970
```

<210> SEQ ID NO 3
<211> LENGTH: 44
<212> TYPE: DNA
<213> ORGANISM: Chlamydia pneumoniae

<400> SEQUENCE: 3
ataagaatgc ggccgccacc atgaaaacgt ctattcgtaa gttc     44

<210> SEQ ID NO 4
<211> LENGTH: 34
<212> TYPE: DNA
<213> ORGANISM: Chlamydia pneumoniae

<400> SEQUENCE: 4
cggggtaccg aaatcgtaat ttgcttccta tatc     34

CHLAMYDIA ANTIGENS AND CORRESPONDING DNA FRAGMENTS AND USES THEREOF

RELATED U.S. APPLICATION

The present patent application claims priority to the following U.S. provisional patent applications: U.S. Ser. No. 60/106,590, filed Nov. 2, 1998 and U.S. Ser. No. 60/133,071, filed May 7, 1999, each incorporated herein by reference.

FIELD OF THE INVENTION

The present invention relates to Chlamydia antigens and corresponding DNA molecules, which can be used in methods to prevent and treat disease caused by Chlamydia infection in mammals, such as humans.

BACKGROUND OF THE INVENTION

Chlamydiae are prokaryotes. They exhibit morphologic and structural similarities to Gram negative bacteria including a trilaminar outer membrane, which contains lipopolysaccharide and several membrane proteins. Chlamydiae are differentiated from other bacteria by their morphology and by a unique developmental cycle. They are obligate intracellular parasites with a unique biphasic life cycle consisting of a metabolically inactive but infectious extracellular stage and a replicating but non-infectious intracellular stage. The replicative stage of the life-cycle takes place within a membrane-bound inclusion which sequesters the bacteria away from the cytoplasm of the infected host cell.

Because chlamydiae are small and multiply only within susceptible cells they were long thought to be viruses. However, they have many characteristics in common with other bacteria: (1) they contain both DNA and RNA, (2) they divide by binary fission, (3) their cell envelopes resemble those of other Gram-negative bacteria, (4) they contain ribosomes similar to those of other bacteria, and (5) they are susceptible to various antibiotics. Chlamydiae can be seen in the light microscope, and the genome is about one-third the size of the *Escherichia coli* genome.

Many different strains of chlamydiae have been isolated from birds, man, and other mammals, and these strains can be distinguished on the basis of host range, virulence, pathogenesis, and antigenic composition. There is strong homology of DNA within each species, but surprisingly little between species, suggesting long-standing evolutionary separation.

*C. trachomatis* has a high degree of host specificity, being almost completely limited to man; it causes ocular and genitourinary infections of widely varying severity. In contrast, *C. psittaci* strains are rare in man but are found in a wide range of birds and also in wild, domestic, and laboratory mammals, where they multiply in cells of many organs.

*C. pneumoniae* is a common human pathogen, originally described as the TWAR strain of *C. psittaci*, but subsequently recognized to be a new species. *C. pneumoniae* is antigenically, genetically, and morphologically distinct from other Chlamydia species (*C. trachomatis, C. pecorum* and *C. psittaci*). It shows 10% or less DNA sequence homology with either of *C. trachomatis* or *C. psittaci* and so far appears to consist of only a single strain, TWAR.

*C. pneumoniae* is a common cause of community acquired pneumonia, less frequent only than *Streptococcus pneumoniae* and *Mycoplasma pneumoniae*. Grayston et al., *J. Infect. Dis.* 168: 1231 (1995); Campos et al., *Invest. Ophthalmol. Vis. Sci.* 36: 1477 (1995), each incorporated herein by reference. It can also cause upper respiratory tract symptoms and disease, including bronchitis and sinusitis. See, e.g., Grayston et al., *J. Infect. Dis.* 168: 1231 (1995); Campos et al., *Invest. Ophthalmol. Vis. Sci.* 36: 1477 (1995); Grayston et al., *J. Infect. Dis.* 161: 618 (1990); Marrie, *Clin. Infect. Dis.* 18: 501 (1993). The great majority of the adult population (over 60%) has antibodies to *C. pneumoniae* (Wang et al., *Chlamydial Infections*, Cambridge University Press, Cambridge, p. 329 (1986)), indicating past infection which was unrecognized or asymptomatic.

*C. pneumoniae* infection usually presents as an acute respiratory disease (i.e., cough, sore throat, hoarseness, and fever; abnormal chest sounds on auscultation). For most patients, the cough persists for 2 to 6 weeks, and recovery is slow. In approximately 10% of these cases, upper respiratory tract infection is followed by bronchitis or pneumonia. Furthermore, during a *C. pneumoniae* epidemic, subsequent co-infection with pneumococcus has been noted in about half of these pneumonia patients, particularly in the infirm and the elderly. As noted above, there is more and more evidence that *C. pneumoniae* infection is also linked to diseases other than respiratory infections.

The reservoir for the organism is presumably people. In contrast to *C. psittaci* infections, there is no known bird or animal reservoir. Transmission has not been clearly defined. It may result from direct contact with secretions, from formites, or from airborne spread. There is a long incubation period, which may last for many months. Based on analysis of epidemics, *C. pneumoniae* appears to spread slowly through a population (case-to-case interval averaging 30 days) because infected persons are inefficient transmitters of the organism. Susceptibility to *C. pneumoniae* is universal. Reinfections occur during adulthood, following the primary infection as a child. *C. pneumoniae* appears to be an endemic disease throughout the world, noteworthy for superimposed intervals of increased incidence (epidemics) that persist for 2 to 3 years. *C. trachomatis* infection does not confer cross-immunity to *C. pneumoniae*. Infections are easily treated with oral antibiotics, tetracycline or erythromycin (2 g/day, for at least 10 to 14 days). A recently developed drug, azithromycin, is highly effective as a single-dose therapy against chlamydial infections.

In most instances, *C. pneumoniae* infection is mild and without complications, and up to 90% of infections are subacute or unrecognized. Among children in industrialized countries, infections have been thought to be rare up to the age of five years, although a recent study has reported that many children in this age group show PCR evidence of infection despite being seronegative, and estimates a prevalence of 17–19% in 2–4 years old. See, Normann et al., *Acta Paediatrica*, 87: 23–27 (1998). In developing countries, the seroprevalence of *C. pneumoniae* antibodies among young children is elevated, and there are suspicions that *C. pneumoniae* may be an important cause of acute lower respiratory tract disease and mortality for infants and children in tropical regions of the world.

From seroprevalence studies and studies of local epidemics, the initial *C. pneumoniae* infection usually happens between the ages of 5 and 20 years. In the USA, for example, there are estimated to be 30,000 cases of childhood pneumonia each year caused by *C. pneumoniae*. Infections may cluster among groups of children or young adults (e.g., school pupils or military conscripts).

*C. pneumoniae* causes 10 to 25% of community-acquired lower respiratory tract infections (as reported from Sweden, Italy, Finland, and the USA). During an epidemic, *C. pneumonia* infection may account for 50 to 60% of the cases of pneumonia. During these periods, also, more episodes of mixed infections with *S. pneumoniae* have been reported.

Reinfection during adulthood is common; the clinical presentation tends to be milder. Based on population seroprevalence studies, there tends to be increased exposure with age, which is particularly evident among men. Some investigators have speculated that a persistent, asymptomatic *C. pneumoniae* infection state is common.

In adults of middle age or older, *C. pneumoniae* infection may progress to chronic bronchitis and sinusitis. A study in the USA revealed that the incidence of pneumonia caused by *C. pneumoniae* in persons younger than 60 years is 1 case per 1,000 persons per year; but in the elderly, the disease incidence rose three-fold. *C. pneumoniae* infection rarely leads to hospitalization, except in patients with an underlying illness.

Of considerable importance is the association of atherosclerosis and *C. pneumoniae* infection. There are several epidemiological studies showing a correlation of previous infections with *C. pneumoniae* and heart attacks, coronary artery and carotid artery disease. See, Saikku et al., *Lancet* 2: 983 (1988); Thom et al., *JAMA* 268: 68 (1992); Linnanmaki et al., *Circulation* 87: 1030 (1993); Saikku et al., *Annals Int. Med.* 116: 273 (1992); Melnick et al., *Am. J. Med.* 95: 499 (1993). Moreover, the organisms has been detected in atheromas and fatty streaks of the coronary, carotid, peripheral arteries and aorta. See, Shor et al., *South African Med. J.* 82: 158 (1992); Kuo et al., *J. Infect. Dis.* 167: 841 (1993); Kuo et al., *Arteriosclerosis and Thrombosis* 13: 1500 (1993); Campbell et al., *J. Infect. Dis.* 172: 585 (1995); Chiu et al., *Circulation* 96: 2144–2148 (1997). Viable *C. pneumoniae* has been recovered from the coronary and carotid artery. Ramirez et al., *Annals Int. Med.* 125: 979 (1996); Jackson et al., Abst. K121, p272, 36th ICAAC, New Orleans (1996). Furthermore, it has been shown that *C. pneumoniae* can induce changes of atherosclerosis in a rabbit model. See, Fong et al., (1997) *Journal of Clinical Microbiolology* 35: 48. Taken together, these results indicate that it is highly probable that *C. pneumoniae* can cause atherosclerosis in humans, though the epidemiological importance of chlamydial atherosclerosis remains to be demonstrated.

A number of recent studies have also indicated an association between *C. pneumoniae* infection and asthma. Infection has been linked to wheezing, asthmatic bronchitis, adult-onset asthma and acute exacerbation of asthma in adults, and small-scale studies have shown that prolonged antibiotic treatment was effective at greatly reducing the severity of the disease in some individuals. Hahn et al., *Ann Allergy Asthma Immunol.* 80: 45–49 (1998); Hahn et al., *Epidemiol Infect.* 117: 513–517 (1996); Bjornsson et al., *Scand J Infect. Dis.* 28: 63–69 (1996); Hahn, *J. Fam. Pract.* 41: 345–351 (1995); Allegra et al., *Eur. Respir. J.* 7: 2165–2168 (1994); Hahn et al., *JAMA* 266: 225–230 (1991).

In light of these results, a protective vaccine against disease caused by *C. pneumoniae* infection would be of considerable importance. There is not yet an effective vaccine for human *C. pneumoniae* infection. Nevertheless, studies with *C. trachomatis* and *C. psittaci* indicate that this is an attainable goal. For example, mice which have recovered from a lung infection with *C. trachomatis* are protected from infertility induced by a subsequent vaginal challenge. Pal et al., *Infection and Immunity* 64: 5341 (1996). Similarly, sheep immunized with inactivated *C. psittaci* were protected from subsequent chlamydial-induced abortions and stillbirths. Jones et al., *Vaccine* 13: 715 (1995). Protection from chlamydial infections has been associated with Th1 immune responses, particularly the induction of INFγ-producing CD4+ T cells. Igietsemes et al., *Immunology* 5: 317 (1993). The adoptive transfer of CD4+ cell lines or clones to nude or SCID mice conferred protection from challenge or cleared chronic disease (Igietseme et al., *Regional Immunology* 5: 317 (1993); Magee et al., *Regional Immunology* 5: 305 (1993)), and in vivo depletion of CD4+ T cells exacerbated disease post-challenge (Landers et al., *Infection & Immunity* 59: 3774 (1991); Magee et al., *Infection & Immunity* 63: 516 (1995)). However, the presence of sufficiently high titres of neutralizing antibody at mucosal surfaces can also exert a protective effect. Cotter et al., *Infection and Immunity* 63: 4704 (1995).

The extent of antigenic variation within the species *C. pneumoniae* is not well characterized. Serovars of *C. trachomatis* are defined on the basis of antigenic variation in major outer membrane proteins (MOMP), but published *C. pneumoniae* MOMP gene sequences show no variation between several diverse isolates of the organism. See, Campbell et al., *Infection and Immunity* 58: 93 (1990); McCafferty et al., *Infection and Immunity* 63: 2387–9 (1995); Knudsen et al., Third Meeting of the European Society for Chlamydia Research, Vienna (1996). Regions of the protein known to be conserved in other chlamydial MOMPs are conserved in *C. pneumoniae*. See, Campbell et al., *Infection and Immunity* 58: 93 (1990); McCafferty et al., *Infection and Immunity* 63: 2387–9 (1995). One study has described a strain of *C. pneumoniae* with a MOMP of greater that usual molecular weight, but the gene for this has not been sequenced. Grayston et al., *J. Infect. Dis.* 168: 1231 (1995). Partial sequences of outer membrane protein 2 from nine diverse isolates were also found to be invariant. Ramirez et al., *Annals Int. Med.* 125: 979 (1996). The genes for HSP60 and HSP70 show little variation from other chlamydial species, as would be expected. The gene encoding a 76 kDa antigen has been cloned from a single strain of *C. pneumoniae*. It has no significant similarity with other known chlamydial genes. Marrie, *Clin. Infect. Dis.* 18: 501 (1993).

Many antigens recognized by immune sera to *C. pneumoniae* are conserved across all chlamydiae, but 98 kDa, 76 kDa and 54 kDa proteins may be *C. pneumoniae*-specific. Campos et al., *Invest. Ophthalmol. Vis. Sci.* 36: 1477 (1995); Marrie, *Clin. Infect. Dis.* 18: 501 (1993); Wiedmann-Al-Ahmad et al., *Clin. Diagn. Lab. Immunol.* 4: 700–704 (1997). Immunoblotting of isolates with sera from patients does show variation of blotting patterns between isolates, indicating that serotypes *C. pneumoniae* may exist. Grayston et al., *J. Infect. Dis.* 168: 1231 (1995); Ramirez et al., *Annals Int. Med.* 125: 979 (1996). However, the results are potentially confounded by the infection status of the patients, since immunoblot profiles of a patient's sera change with time post-infection. An assessment of the number and relative frequency of any serotypes, and the defining antigens, is not yet possible.

Thus, a need remains for effective compositions for preventing, treating, and diagnosing Chlamydia infections.

SUMMARY OF THE INVENTION

In one aspect, the present invention provides purified and isolated DNA molecules that encode Chlamydia which can be used in methods to prevent, treat, and diagnose Chlamydia infection. Encoded polypeptides, designated POMP91B precursor, include polypeptides having the amino acid sequence shown in SEQ ID NO: 2 and the DNA molecules include SEQ ID NO: 1 full-length sequence (top sequence) and coding sequence (bottom sequence) for the mature polypeptide. Those skilled in the art will appreciate that the invention also includes DNA molecules that encode mutants, variants, and derivatives of such polypeptides, which result from the addition, deletion, or substitution of non-essential amino acids as described herein. The invention also includes RNA molecules corresponding to the DNA molecules of the invention.

In addition to the DNA and RNA molecules, the invention includes the corresponding polypeptides and monospecific antibodies that specifically bind to such polypeptides.

The present invention has wide application and includes expression cassettes, vectors, and cells transformed or transfected with the polynucleotides of the invention. Accordingly, the present invention provides (i) a method for producing a polypeptide of the invention in a recombinant host system and related expression cassettes, vectors, and transformed or transfected cells; (ii) a live vaccine vectors such as viral or bacterial live vaccine vectors, including, pox virus, alphavirus, *Salmonella typhimurium*, or *Vibrio cholerae* vector, containing a polynucleotide of the invention, such vaccine vectors being useful for, e.g., preventing and treating Chlamydia infection, in combination with a diluent or carrier, and related pharmaceutical compositions and associated therapeutic and/or prophylactic methods; (iii) a therapeutic and/or prophylactic method involving administration of an RNA or DNA molecule of the invention, either in a naked form or formulated with a delivery vehicle, a polypeptide or combination of polypeptides, or a monospecific antibody of the invention, and related pharmaceutical compositions; (iv) a method for diagnosing the presence of Chlamydia in a biological sample, which can involve the use of a DNA or RNA molecule, a monospecific antibody, or a polypeptide of the invention; and (v) a method for purifying a polypeptide of the invention by antibody-based affinity chromatography. The present invention provides purified and isolated DNA molecules, which encode Chlamydia that can be used in methods to prevent, treat, and diagnose Chlamydia infection.

BRIEF DESCRIPTION OF THE DRAWINGS

The present invention will be further understood from the following description with reference to the drawings, in which:

FIG. 1 shows the nucleotide sequence of the full length POMP91B precursor gene (top sequence) (SEQ ID NO: 1) and the deduced amino acid sequence of the POMP91B processed protein from *Chlamydia pneumoniae* (bottom sequence) (SEQ ID NO:2).

Figure 2E:
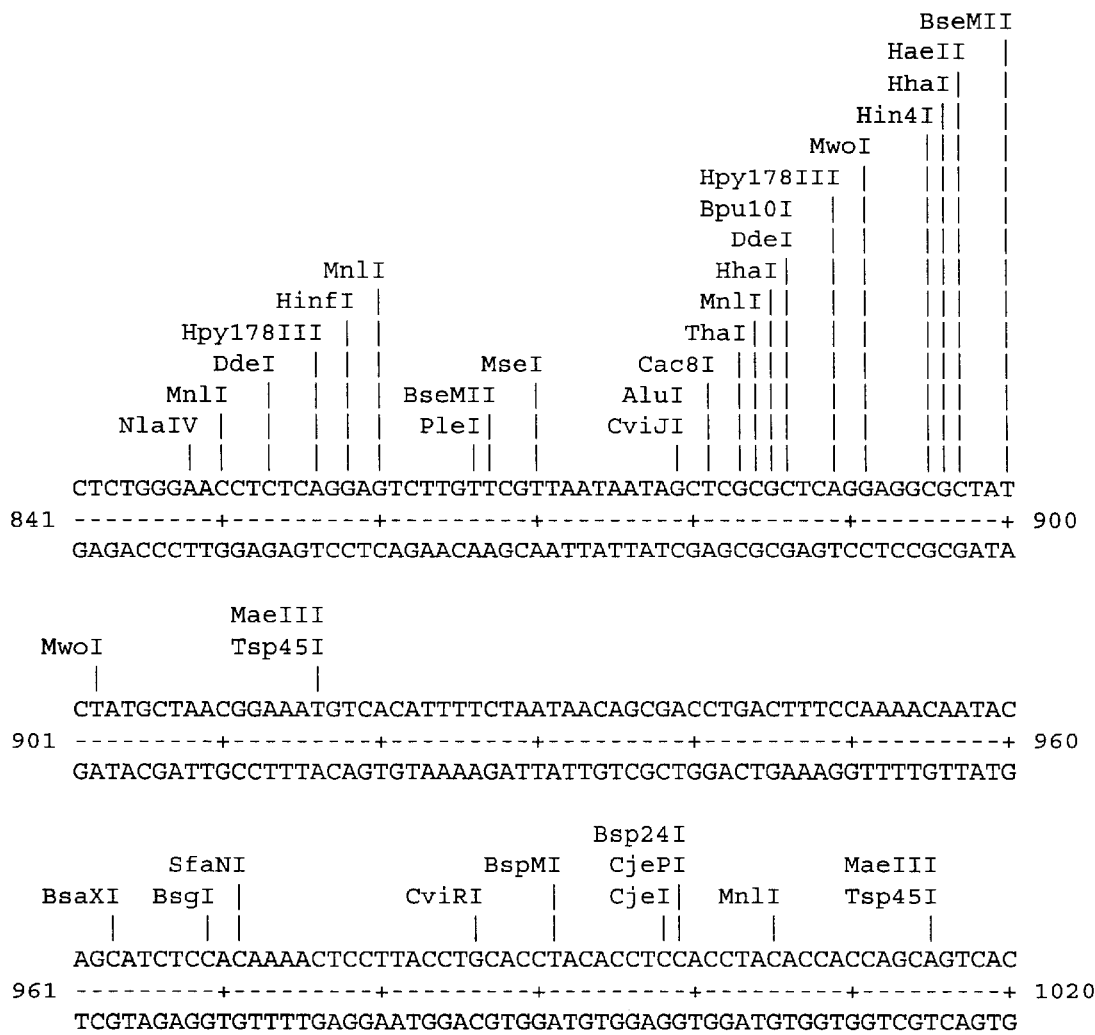
FIG. 2 shows the restriction enzyme analysis of nucleotide sequence encoding the *C. pneumoniae* POMP91B precursor gene.
Figure 2H:
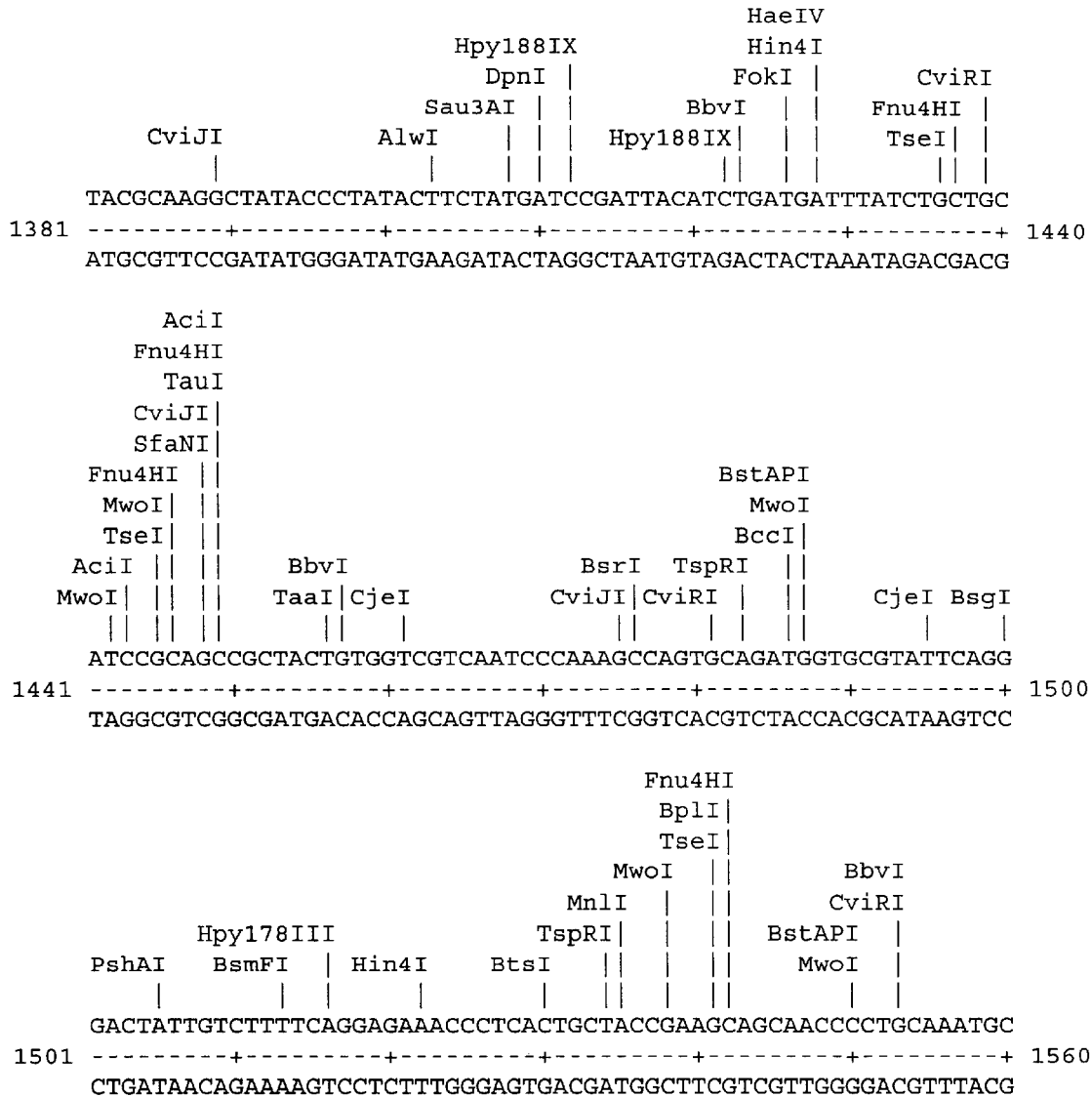
Figure 3:
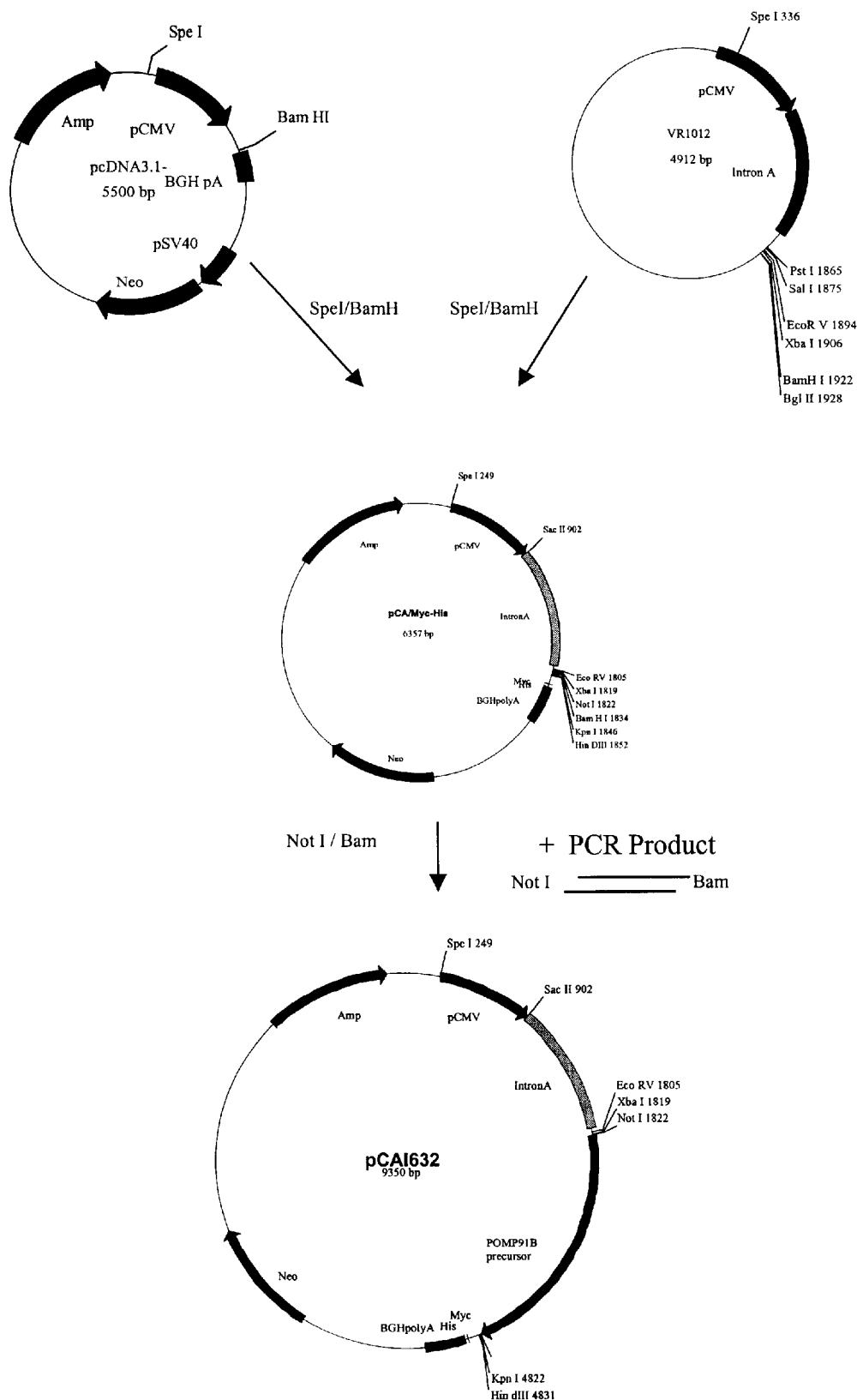
FIG. 3 shows the construction and elements of plasmid pCAI632.

Homology is typically measured using sequence analysis software (e.g., Sequence Analysis Software Package of the Genetics Computer Group, University of Wisconsin Biotechnology Center, 1710 University Avenue, Madison, Wis. 53705). Similar amino acid sequences are aligned to obtain the maximum degree of homology (i.e., identity). To this end, it may be necessary to artificially introduce gaps into the sequence. Once the optimal alignment has been set up, the degree of homology (i.e., identity) is established by recording all of the positions in which the amino acids of both sequences are identical, relative to the total number of positions.

Similarity factors include similar size, shape and electrical charge. One particularly preferred method of determining amino acid similarities is the PAM250 matrix described in Dayhoff et al., 5 *Atlas of Protein Sequence and Structure* 345–352 (1978 & Suppl.), incorporated by reference herein. A similarity score is first calculated as the sum of the aligned pairwise amino acid similarity scores. Insertions and deletions are ignored for the purposes of percent homology and identity. Accordingly, gap penalties are not used in this calculation. The raw score is then normalized by dividing it by the geometric mean of the scores of the candidate compound and the reference sequence. The geometric mean is the square root of the product of these scores. The normalized raw score is the percent homology.

Preferably, a homologous sequence is one that is at least 45%, more preferably 60%, and most preferably 85% identical to the coding sequence of SEQ ID NO: 1.

Polypeptides having a sequence homologous to one of the sequences shown in SEQ ID NOS: 1 and 2, include naturally-occurring allelic variants, as well as mutants and variants or any other non-naturally-occurring variants that are analogous in terms of antigenicity, to a polypeptide having a sequence as shown in SEQ ID NOS: 1 or 2.

An allelic variant is an alternate form of a polypeptide that is characterized as having a substitution, deletion, or addition of one or more amino acids that does not substantially alter the biological function of the polypeptide. By "biological function" is meant the function of the polypeptide in the cells in which it naturally occurs, even if the function is not necessary for the growth or survival of the cells. For example, the biological function of a porin is to allow the entry into cells of compounds present in the extracellular medium. The biological function is distinct from the antigenic function. A polypeptide can have more than one biological function.

Allelic variants are very common in nature. For example, a bacterial species, e.g., *C. pneumoniae*, is usually represented by a variety of strains that differ from each other by minor allelic variations. Indeed, a polypeptide that fulfills the same biological function in different strains can have an amino acid sequence that is not identical in each of the strains. Such an allelic variation may be equally reflected at the polynucleotide level.

Support for the use of allelic variants of polypeptide antigens comes from, e.g., studies of the Chlamydial MOMP antigen. The amino acid sequence of the MOMP varies from strain to strain, yet cross-strain antibody binding plus neutralization of infectivity occurs, indicating that the MOMP, when used as an immunogen, is tolerant of amino acid variations.

Polynucleotides, e.g., DNA molecules, encoding allelic variants can easily be retrieved by polymerase chain reaction (PCR) amplification of genomic bacterial DNA extracted by conventional methods. This involves the use of synthetic oligonucleotide primers matching upstream and downstream of the 5' and 3' ends of the encoding domain. Suitable primers can be designed according to the nucleotide sequence information provided in SEQ ID NOS: 1 and 2. Typically, a primer can consist of 10–40, preferably 15–25 nucleotides. It may be also advantageous to select primers containing C and G nucleotides in a proportion sufficient to ensure efficient hybridization; e.g., an amount of C and G nucleotides of at least 40%, preferably 50% of the total nucleotide amount.

Useful homologs that do not naturally occur can be designed using known methods for identifying regions of an antigen that are likely to be tolerant of amino acid sequence changes and/or deletions. For example, sequences of the antigen from different species can be compared to identify conserved sequences.

Polypeptide derivatives that are encoded by polynucleotides of the invention include, e.g., fragments, polypeptides having large internal deletions derived from full-length polypeptides, and fusion proteins.

Polypeptide fragments of the invention can be derived from a polypeptide having a sequence homologous to any of the sequences shown in SEQ ID NOS: 1 and 2, to the extent that the fragments retain the desired substantial antigenicity of the parent polypeptide (specific antigenicity). Polypeptide derivatives can also be constructed by large internal deletions that remove a substantial part of the parent polypeptide, while retaining the desired specific antigenicity. Generally, polypeptide derivatives should be about at least 12 amino acids in length to maintain the antigenicity. Advantageously, they can be at least 20 amino acids, preferably at least 50 amino acids, more preferably at least 75 amino acids, and most preferably at least 100 amino acids in length.

Useful polypeptide derivatives, e.g., polypeptide fragments, can be designed using computer-assisted analysis of amino acid sequences in order to identify sites in protein antigens having potential as surface-exposed, antigenic regions. Hughes et al., *Infect. Immun.* 60: 3497 (1992).

Polypeptide fragments and polypeptides having large internal deletions can be used for revealing epitopes that are otherwise masked in the parent polypeptide and that may be of importance for inducing, for example, a protective T cell-dependent immune response. Deletions can also remove immunodominant regions of high variability among strains.

It is an accepted practice in the field of immunology to use fragments and variants of protein immunogens as vaccines and immunogens, as all that is required to induce an immune response to a protein may be a small (e.g., 8 to 10 amino acid) region of the protein. This has been done for a number of vaccines against pathogens other than Chlamydia. For example, short synthetic peptides corresponding to surface-exposed antigens of pathogens such as murine mammary tumor virus, peptide containing 11 amino acids (Dion et al., *Virology* 179: 474–477 (1990)); Semliki Forest virus, peptide containing 16 amino acids (Snijders et al., *J. Gen. Virol.* 72: 557–565 (1991)); and canine parvovirus, two overlapping peptides, each containing 15 amino acids (Langeveld et al., *Vaccine* 12: 1473–1480 (1994)) have been shown to be effective vaccine antigens against their respective pathogens.

Polynucleotides encoding polypeptide fragments and polypeptides having large internal deletions can be constructed using standard methods (see, e.g., Ausubel et al., *Current Protocols in Molecular Biology*, John Wiley & Sons Inc. (1994)); for example, by PCR, including inverse PCR, by restriction enzyme treatment of the cloned DNA molecules, or by the method of Kunkel et al. (*Proc. Natl. Acad. Sci. USA* 82: 448 (1985)); biological material available at Stratagene.

A polypeptide derivative can also be produced as a fusion polypeptide that contains a polypeptide or a polypeptide derivative of the invention fused, e.g., at the N- or C-terminal end, to any other polypeptide. For construction of DNA encoding the amino acid sequence corresponding to hybrid fusion proteins, a first DNA encoding amino acid sequence corresponding to portions of SEQ ID NO: 1 or 2 is joined to a second DNA using methods described in, for example, U.S. Pat. No. 5,844,095, incorporated herein by reference. A product can then be easily obtained by translation of the genetic fusion. Vectors for expressing fusion polypeptides are commercially available, such as the pMal-c2 or pMal-p2 systems of New England Biolabs, in which the fusion peptide is a maltose binding protein, the glutathione-S-transferase system of Pharmacia, or the His-Tag system available from Novagen. These and other expression systems provide convenient means for further purification of polypeptides and derivatives of the invention.

Another particular example of fusion polypeptides included in the invention includes a polypeptide or polypeptide derivative of the invention fused to a polypeptide having adjuvant activity, such as, e.g., the subunit B of either cholera toxin or *E. coli* heat-labile toxin. Several possibilities are can be used for achieving fusion. First, the polypeptide of the invention can be fused to the N-, or preferably, to the C-terminal end of the polypeptide having adjuvant activity. Second, a polypeptide fragment of the invention can be fused within the amino acid sequence of the polypeptide having adjuvant activity.

As stated above, the polynucleotides of the invention encode Chlamydia polypeptides in precursor or mature form. They can also encode hybrid precursors containing heterologous signal peptides, which can mature into polypeptides of the invention. By "heterologous signal peptide" is meant a signal peptide that is not found in the naturally-occurring precursor of a polypeptide of the invention.

A polynucleotide of the invention, having a homologous coding sequence, hybridizes, preferably under stringent conditions, to a polynucleotide having a sequence as shown in SEQ ID NO: 1. Hybridization procedures are described in, e.g., Ausubel et al., *Current Protocols in Molecular Biology*, John Wiley & Sons Inc. (1994); Silhavy et al., *Experiments With Gene Fusions*, Cold Spring Harbor Laboratory Press (1984); Davis et al., *A Manual For Genetic Engineering: Advanced Bacterial Genetics*, Cold Spring Harbor Laboratory Press (1980), each incorporated herein by reference. Important parameters that can be considered for optimizing hybridization conditions are reflected in a formula that allows calculation of a critical value, the melting temperature above which two complementary DNA strands separate from each other. Casey and Davidson, *Nucl. Acid Res.* 4: 1539 (1977). This formula is as follows:

$$Tm = 81.5 + 0.5 \times (\% \text{ G+C}) + 1.6 \log (\text{positive ion concentration}) - 0.6 \times (\% \text{ formamide}).$$

Under appropriate stringency conditions, hybridization temperature (Th) is approximately 20–40° C., 20–25° C. or, preferably, 30–40° C. below the calculated Tm. Those skilled in the understand that optimal temperature and salt conditions can be readily determined empirically in preliminary experiments using conventional procedures.

For example, stringent conditions can be achieved, both for pre-hybridizing and hybridizing incubations, (i) within 4–16 hours at 42° C., in 6×SSC containing 50% formamide or (ii) within 4–16 hours at 65° C. in an aqueous 6×SSC solution (1 M NaCl, 0.1 M sodium citrate (pH 7.0)).

For polynucleotides containing 30 to 600 nucleotides, the above formula is used and then is corrected by subtracting (600/polynucleotide size in base pairs). Stringency conditions are defined by a Th that is 5 to 10° C. below Tm.

Hybridization conditions with oligonucleotides shorter than 20–30 bases do not exactly follow the rules set forth above. In such cases, the formula for calculating the Tm is as follows:

$$Tm = 4 \times (G+C) + 2(A+T).$$

For example, an 18 nucleotide fragment of 50% G+C would have an approximate Tm of 54° C.

A polynucleotide molecule of the invention, containing RNA, DNA, or modifications or combinations thereof, can have various applications. For example, a DNA molecule can be used (i) in a process for producing the encoded polypeptide in a recombinant host system, (ii) in the construction of vaccine vectors such as poxviruses, which are further used in methods and compositions for preventing and/or treating Chlamydia infection, (iii) as a vaccine agent (as well as an RNA molecule), in a naked form or formulated with a delivery vehicle and, (iv) in the construction of attenuated Chlamydia strains that can overexpress a polynucleotide of the invention or express it in a modified, mutated form, such as a non-toxic form, if appropriate. For vaccine compositions and uses of the proteins and peptides and encoding nucleotides of the present invention for protection against diseases caused by Chlamydia, it is not preferred to use naked DNA encoding the protein or peptides and administering these nucleotides intranasally or intramuscularly. For these proteins, it is preferred to administer the encoding nucleic acids by other routes such as intradermally and/or to formulate the encoding nucleic acids to improve (or adjuvant) the immune response. It is also preferred to include the encoding nucleic acid as part of a recombinant live vector, such as a viral or bacterial vector for use as the immunizing agent. It is also preferred to immunize with vaccine formulations comprising the proteins or peptides of the invention themselves. These vaccine formulations may include the use of adjuvants.

According to a second aspect of the invention, there is therefore provided (i) an expression cassette containing a DNA molecule of the invention placed under the control of the elements required for expression, in particular under the control of an appropriate promoter; (ii) an expression vector containing an expression cassette of the invention; (iii) a prokaryotic or eukaryotic cell transformed or transfected with an expression cassette and/or vector of the invention, as well as (iv) a process for producing a polypeptide or polypeptide derivative encoded by a polynucleotide of the invention, which involves culturing a prokaryotic or eukaryotic cell transformed or transfected with an expression cassette and/or vector of the invention, under conditions that allow expression of the DNA molecule of the invention and, recovering the encoded polypeptide or polypeptide derivative from the cell culture.

A recombinant expression system can be selected from prokaryotic and eukaryotic hosts. Eukaryotic hosts include yeast cells (e.g., *Saccharomyces cerevisiae* or *Pichia pastoris*), mammalian cells (e.g., COS1, NIH3T3, or JEG3 cells), arthropods cells (e.g., *Spodoptera frugiperda* (*SF*9) cells), and plant cells. Preferably, a prokaryotic host such as *E. coli* is used. Bacterial and eukaryotic cells are available from a number of different sources to those skilled in the art, e.g., the American Type Culture Collection (ATCC; 10801 University Boulevard, Manassas, Va. 20110-2209).

The choice of the expression system depends on the features desired for the expressed polypeptide. For example, it may be useful to produce a polypeptide of the invention in a particular lipidated form or any other form.

The choice of the expression cassette will depend on the host system selected as well as the features desired for the expressed polypeptide. Typically, an expression cassette includes a promoter that is functional in the selected host system and can be constitutive or inducible; a ribosome binding site; a start codon (ATG) if necessary, a region encoding a signal peptide, e.g., a lipidation signal peptide; a DNA molecule of the invention; a stop codon; and optionally a 3' terminal region (translation and/or transcription terminator). The signal peptide encoding region is adjacent to the polynucleotide of the invention and placed in proper reading frame. The signal peptide-encoding region can be homologous or heterologous to the DNA molecule encoding the mature polypeptide and can be specific to the secretion apparatus of the host used for expression. The open reading frame constituted by the DNA molecule of the invention, solely or together with the signal peptide, is placed under the control of the promoter so that transcription and translation occur in the host system. Promoters, signal peptide encoding regions are widely known and available to those skilled in the art and includes, for example, the promoter of *Salmonella typhimurium* (and derivatives) that is inducible by arabinose (promoter araB) and is functional in Gram-negative bacteria such as *E. coli* (as described in U.S. Pat. No. 5,028,530 and in Cagnon et al., *Protein Engineering* 4: 843 (1991)); the promoter of the gene of bacteriophage T7 encoding RNA polymerase, that is functional in a number of *E. coli* strains expressing T7 polymerase (described in U.S. Pat. No. 4,952,496); OspA lipidation signal peptide; and RlpB lipidation signal peptide (Takase et al., *J. Bact.* 169: 5692 (1987)).

The expression cassette is typically part of an expression vector, which is selected for its ability to replicate in the chosen expression system. Expression vectors (e.g., plasmids or viral vectors) can be chosen from those described in Pouwels et al. (*Cloning Vectors: Laboratory Manual*, 85, Supp. 1987). They can be purchased from various commercial sources.

Methods for transforming/transfecting host cells with expression vectors will depend on the host system selected as described in Ausubel et al., *Current Protocols in Molecular Biology*, John Wiley & Sons Inc. (1994).

Upon expression, a recombinant polypeptide of the invention (or a polypeptide derivative) is produced and remains in the intracellular compartment, is secreted/excreted in the extracellular medium or in the periplasmic space, or is embedded in the cellular membrane. The polypeptide can then be recovered in a substantially purified form from the cell extract or from the supernatant after centrifugation of the recombinant cell culture. Typically, the recombinant polypeptide can be purified by antibody-based affinity purification or by any other method that can be readily adapted by a person skilled in the art, such as by genetic fusion to a small affinity binding domain. Antibody-based affinity purification methods are also available for purifying a polypeptide of the invention extracted from a Chlamydia strain. Antibodies useful for purifying by immunoaffinity the polypeptides of the invention can be obtained as described below.

A polynucleotide of the invention can also be useful in the vaccine field, e.g., for achieving DNA vaccination. There are two major possibilities, either using a viral or bacterial host as gene delivery vehicle (live vaccine vector) or administering the gene in a free form, e.g., inserted into a plasmid. Therapeutic or prophylactic efficacy of a polynucleotide of the invention can be evaluated as described below.

Accordingly, in a third aspect of the invention, there is provided (i) a vaccine vector such as a poxvirus, containing a DNA molecule of the invention, placed under the control of elements required for expression; (ii) a composition of matter containing a vaccine vector of the invention, together with a diluent or carrier; particularly, (iii) a pharmaceutical composition containing a therapeutically or prophylactically effective amount of a vaccine vector of the invention; (iv) a method for inducing an immune response against Chlamydia in a mammal (e.g., a human; alternatively, the method can be used in veterinary applications for treating or preventing Chlamydia infection of animals, e.g., cats or birds), which involves administering to the mammal an immunogenically effective amount of a vaccine vector of the invention to elicit an immune response, e.g., a protective or therapeutic immune response to Chlamydia; and particularly, (v) a method for preventing and/or treating a Chlamydia (e.g., *C. trachomatis, C. psittaci, C. pneumonia, C. pecorum*) infection, which involves administering a prophylactic or therapeutic amount of a vaccine vector of the invention to an individual in need. Additionally, the third aspect of the invention encompasses the use of a vaccine vector of the invention in the preparation of a medicament for preventing and/or treating Chlamydia infection.

A vaccine vector of the invention can express one or several polypeptides or derivatives of the invention, as well as at least one additional Chlamydia antigen, fragment, homolog, mutant, or derivative thereof. In addition, it can express a cytokine, such as interleukin-2 (IL-2) or interleukin-12 (IL-12), that enhances the immune response (adjuvant effect). Thus, a vaccine vector can include an additional DNA sequence encoding, e.g., a chlamydial antigen, or a cytokine, placed under the control of elements required for expression in a mammalian cell.

Alternatively, a composition of the invention can include several vaccine vectors, each of them being capable of expressing a polypeptide or derivative of the invention. A composition can also contain a vaccine vector capable of expressing an additional Chlamydia antigen, or a subunit, fragment, homolog, mutant, or derivative thereof; or a cytokine such as IL-2 or IL-12.

In vaccination methods for treating or preventing infection in a mammal, a vaccine vector of the invention can be administered by any conventional route in use in the vaccine field, particularly, to a mucosal (e.g., ocular, intranasal, oral, gastric, pulmonary, intestinal, rectal, vaginal, or urinary tract) surface or via the parenteral (e.g., subcutaneous, intradermal, intramuscular, intravenous, or intraperitoneal) route. Preferred routes depend upon the choice of the vaccine vector. The administration can be achieved in a single dose or repeated at intervals. The appropriate dosage depends on various parameters understood by skilled artisans such as the vaccine vector itself, the route of administration or the condition of the mammal to be vaccinated (weight, age and the like).

Live vaccine vectors available in the art include viral vectors such as adenoviruses, alphavirus, and poxviruses as well as bacterial vectors, e.g., Shigella, Salmonella, *Vibrio cholerae*, Lactobacillus, Bacille bilié de Calmette-Guérin (BCG), and Streptococcus.

An example of an adenovirus vector, as well as a method for constructing an adenovirus vector capable of expressing a DNA molecule of the invention, are described in U.S. Pat. No. 4,920,209. Poxvirus vectors that can be used include, e.g., vaccinia and canary pox virus, described in U.S. Pat. No. 4,722,848 and U.S. Pat. No. 5,364,773, respectively (also see, e.g., Tartaglia et al., *Virology* 188: 217 (1992)) for a description of a vaccinia virus vector; and Taylor et al, *Vaccine* 13: 539 (1995) for a reference of a canary pox). Poxvirus vectors capable of expressing a polynucleotide of the invention can be obtained by homologous recombination as described in Kieny et al., *Nature* 312: 163 (1984) so that the polynucleotide of the invention is inserted in the viral genome under appropriate conditions for expression in mammalian cells. Generally, the dose of vaccine viral vector, for therapeutic or prophylactic use, can be of from about $1 \times 10^4$ to about $1 \times 10^{11}$, advantageously from about $1 \times 10^7$ to about $1 \times 10^{10}$, preferably of from about $1 \times 10^7$ to about $1 \times 10^9$ plaque-forming units per kilogram. Preferably, viral vectors are administered parenterally; for example, in three doses, four weeks apart. Those skilled in the art recognize that it is preferable to avoid adding a chemical adjuvant to a composition containing a viral vector of the invention and thereby minimizing the immune response to the viral vector itself.

Non-toxicogenic *Vibrio cholerae* mutant strains that are useful as a live oral vaccine are described in Mekalanos et al., *Nature* 306: 551 (1983) and U.S. Pat. No. 4,882,278 (strain in which a substantial amount of the coding sequence of each of the two ctxA alleles has been deleted so that no functional cholerae toxin is produced); WO 92/11354 (strain in which the irgA locus is inactivated by mutation; this mutation can be combined in a single strain with ctxA mutations); and WO 94/1533 (deletion mutant lacking functional ctxA and attRS1 DNA sequences). These strains can be genetically engineered to express heterologous antigens, as described in WO 94/19482. An effective vaccine dose of a *Vibrio cholerae* strain capable of expressing a polypeptide or polypeptide derivative encoded by a DNA molecule of the invention can contain, e.g., about $1 \times 10^5$ to about $1 \times 10^9$, preferably about $1 \times 10^6$ to about $1 \times 10^8$ viable bacteria in an appropriate volume for the selected route of administration. Preferred routes of administration include all mucosal routes; most preferably, these vectors are administered intranasally or orally.

Attenuated *Salmonella typhimurium* strains, genetically engineered for recombinant expression of heterologous antigens or not, and their use as oral vaccines are described in Nakayama et al., *Bio/Technology* 6: 693 (1988) and WO 92/11361. Preferred routes of administration include all mucosal routes; most preferably, these vectors are administered intranasally or orally.

Others bacterial strains useful as vaccine vectors are described in High et al., *EMBO* 11: 1991 (1992); Sizemore et al., *Science* 270: 299 (1995) (*Shigella flexneri*); Medaglini et al., *Proc. Natl. Acad. Sci. USA* 92: 6868 (1995) (*Streptococcus gordonii*); and Flynn, *Cell. Mol. Biol.* 40: 31 (1994), WO 88/6626, WO 90/0594, WO 91/13157, WO 92/1796, and WO 92/21376 (Bacille Calmette Guerin).

In bacterial vectors, polynucleotide of the invention can be inserted into the bacterial genome or can remain in a free state, carried on a plasmid.

An adjuvant can also be added to a composition containing a vaccine bacterial vector. A number of adjuvants are known to those skilled in the art. Preferred adjuvants can be selected from the list provided below.

According to a fourth aspect of the invention, there is also provided (i) a composition of matter containing a polynucleotide of the invention, together with a diluent or carrier; (ii) a pharmaceutical composition containing a therapeutically or prophylactically effective amount of a polynucleotide of the invention; (iii) a method for inducing an immune response against Chlamydia, in a mammal, by administering to the mammal, an immunogenically effective amount of a polynucleotide of the invention to elicit an immune response, e.g., a protective immune response to Chlamydia; and particularly, (iv) a method for preventing and/or treating a Chlamydia (e.g., *C. trachomatis, C. psittaci, C. pneumoniae*, or *C. pecorum*) infection, by administering a prophylactic or therapeutic amount of a polynucleotide of the invention to an individual in need. Additionally, the fourth aspect of the invention encompasses the use of a polynucleotide of the invention in the preparation of a medicament for preventing and/or treating Chlamydia infection. The fourth aspect of the invention preferably includes the use of a DNA molecule placed under conditions for expression in a mammalian cell, e.g., in a plasmid that is unable to replicate in mammalian cells and to substantially integrate in a mammalian genome.

Polynucleotides (DNA or RNA) of the invention can also be administered as such to a mammal for vaccine, e.g., therapeutic or prophylactic, purpose. When a DNA molecule of the invention is used, it can be in the form of a plasmid that is unable to replicate in a mammalian cell and unable to integrate in the mammalian genome. Typically, a DNA molecule is placed under the control of a promoter suitable for expression in a mammalian cell. The promoter can function ubiquitously or tissue-specifically. Examples of non-tissue specific promoters include the early Cytomegalovirus (CMV) promoter (described in U.S. Pat. No. 4,168,062) and the Rous Sarcoma Virus promoter (described in Norton & Coffin, *Molec. Cell Biol.* 5: 281(1985)). The desmin promoter (Li et al., *Gene* 78: 243 (1989), Li & Paulin, *J. Biol. Chem.* 266: 6562 (1991), and Li & Paulin, *J. Biol. Chem.* 268: 10403 (1993)) is tissue-specific and drives expression in muscle cells. More generally, useful vectors are described, i.a., WO 94/21797 and Hartikka et al., *Human Gene Therapy* 7: 1205 (1996).

For DNA/RNA vaccination, the polynucleotide of the invention can encode a precursor or a mature form. When it encodes a precursor form, the precursor form can be homologous or heterologous. In the latter case, a eukaryotic leader sequence can be used, such as the leader sequence of the tissue-type plasminogen factor (tPA).

A composition of the invention can contain one or several polynucleotides of the invention. It can also contain at least one additional polynucleotide encoding another Chlamydia antigen or a fragment, derivative, mutant, or analog thereof. A polynucleotide encoding a cytokine, such as interleukin-2 (IL-2) or interleukin- 12 (IL-12), can also be added to the composition so that the immune response is enhanced. These additional polynucleotides are placed under appropriate control for expression. Advantageously, DNA molecules of the invention and/or additional DNA molecules to be included in the same composition, can be carried in the same plasmid.

Standard techniques of molecular biology for preparing and purifying polynucleotides can be used in the preparation of polynucleotide therapeutics of the invention. For use as a vaccine, a polynucleotide of the invention can be formulated according to various methods.

First, a polynucleotide can be used in a naked form, free of any delivery vehicles, such as anionic liposomes, cationic lipids, microparticles, e.g., gold microparticles, precipitating agents, e.g., calcium phosphate, or any other transfection-facilitating agent. In this case, the polynucleotide can be simply diluted in a physiologically acceptable solution, such as sterile saline or sterile buffered saline, with or without a carrier. When present, the carrier preferably is isotonic, hypotonic, or weakly hypertonic, and has a relatively low ionic strength, such as provided by a sucrose solution, e.g., a solution containing 20% sucrose.

Alternatively, a polynucleotide can be associated with agents that assist in cellular uptake.

It can be, i.a., (i) complemented with a chemical agent that modifies the cellular permeability, such as bupivacaine (see, e.g., WO 94/16737), (ii) encapsulated into liposomes, or (iii) associated with cationic lipids or silica, gold, or tungsten microparticles.

Anionic and neutral liposomes are well-known in the art (see, e.g., Liposomes: A Practical Approach, RPC New Ed, IRL Press (1990)), for a detailed description of methods for making liposomes) and are useful for delivering a large range of products, including polynucleotides.

Cationic lipids are also known in the art and are commonly used for gene delivery. Such lipids include Lipofectin™ also known as DOTMA (N-[1-(2,3-dioleyloxy) propyl]-N,N,N-trimethylammonium chloride), DOTAP (1,2-bis(oleyloxy)-3-(trimethylammonio)propane), DDAB (dimethyldioctadecylammonium bromide), DOGS (dioctadecylamidologlycyl spermine) and cholesterol derivatives such as DC-Chol (3 beta-(N-(N',N'-dimethyl aminomethane)-carbamoyl) cholesterol). A description of these cationic lipids can be found in EP 187,702, WO 90/11092, U.S. Pat. No. 5,283,185, WO 91/15501, WO 95/26356, and U.S. Pat. No. 5,527,928. Cationic lipids for gene delivery are preferably used in association with a neutral lipid such as DOPE (dioleyl phosphatidylethanolamine), as described in, e.g., WO 90/11092.

Other transfection-facilitating compounds can be added to a formulation containing cationic liposomes. A number of them are described in, e.g., WO 93/18759, WO 93/19768, WO 94/25608, and WO 95/2397. They include, i.a., spernine derivatives useful for facilitating the transport of DNA through the nuclear membrane (see, for example, WO 93/18759) and membrane-permeabilizing compounds such as GALA, Gramicidine S, and cationic bile salts (see, for example, WO 93/19768).

Gold or tungsten microparticles can also be used for gene delivery, as described in WO 91/359, WO 93/17706, and Tang et al. (Nature 356: 152 (1992)). In this case, the microparticle-coated polynucleotides can be injected via intradermal or intra-epidermal routes using a needleless injection device ("gene gun"), such as those described in U.S. Pat. No. 4,945,050, U.S. Pat. No. 5,015,580, and WO 94/24263.

The amount of DNA to be used in a vaccine recipient depends, e.g., on the strength of the promoter used in the DNA construct, the immunogenicity of the expressed gene product, the condition of the mammal intended for administration (e.g., the weight, age, and general health of the mammal), the mode of administration, and the type of formulation. In general, a therapeutically or prophylactically effective dose from about 1 µg to about 1 mg, preferably, from about 10 µg to about 800 µg and, more preferably, from about 25 µg to about 250 µg, can be administered to human adults. The administration can be achieved in a single dose or repeated at intervals.

The route of administration can be any conventional route used in the vaccine field. As general guidance, a polynucleotide of the invention can be administered via a mucosal surface, e.g., an ocular, intranasal, pulmonary, oral, intestinal, rectal, vaginal, and urinary tract surface; or via a parenteral route, e.g., by an intravenous, subcutaneous, intraperitoneal, intradermal, intraepidermal, or intramuscular route. The choice of the administration route will depend on, e.g., the formulation that is selected. A polynucleotide formulated in association with bupivacaine is advantageously administered into muscles. When a neutral or anionic liposome or a cationic lipid, such as DOTMA or DC-Chol, is used, the formulation can be advantageously injected via intravenous, intranasal (aerosolization), intramuscular, intradermal, and subcutaneous routes. A polynucleotide in a naked form can advantageously be administered via the intramuscular, intradermal, or subcutaneous routes.

Although not absolutely required, such a composition can also contain an adjuvant. If so, a systemic adjuvant that does not require concomitant administration in order to exhibit an adjuvant effect is preferable such as, e.g., QS21, which is described in U.S. Pat. No. 5,057,546.

The sequence information provided in the present application enables the design of specific nucleotide probes and primers that can be useful in diagnosis. Accordingly, in a fifth aspect of the invention, there is provided a nucleotide probe or primer having a sequence found in or derived by degeneracy of the genetic code from a sequence shown in SEQ ID NO: 1.

The term "probe" as used in the present application refers to DNA (preferably single stranded) or RNA molecules (or modifications or combinations thereof) that hybridize under the stringent conditions, as defined above, to nucleic acid molecules having sequences homologous to those shown in SEQ ID NOS: 1 and 2, or to a complementary or anti-sense sequence. Generally, probes are significantly shorter than full-length sequences shown in SEQ ID NOS: 1 and 2; for example, they can contain from about 5 to about 100, preferably from about 10 to about 80 nucleotides. In particular, probes have sequences that are at least 75%, preferably at least 85%, more preferably 95% homologous to a portion of a sequence as shown in SEQ ID NOS: 1 and 2 or that are complementary to such sequences. Probes can contain modified bases such as inosine, methyl-5-deoxycytidine, deoxyuridine, dimethylamino-5-deoxyuridine, or diamino-2,6-purine. Sugar or phosphate residues can also be modified or substituted. For example, a deoxyribose residue can be replaced by a polyamide (Nielsen et al., Science 254: 1497 (1991)) and phosphate residues can be replaced by ester groups such as diphosphate, alky, arylphosphonate and phosphorothioate esters. In addition, the 2'-hydroxyl group on ribonucleotides can be modified by including, e.g., alkyl groups.

Probes of the invention can be used in diagnostic tests, as capture or detection probes. Such capture probes can be conventionally immobilized on a solid support, directly or indirectly, by covalent means or by passive adsorption. A detection probe can be labelled by a detection marker selected from radioactive isotopes; enzymes such as peroxidase, alkaline phosphatase, and enzymes able to hydrolyze a chromogenic, fluorogenic, or luminescent substrate; compounds that are chromogenic, fluorogenic, or luminescent; nucleotide base analogs; and biotin.

Probes of the invention can be used in any conventional hybridization technique, such as dot blot (Maniatis et al., *Molecular Cloning: A Laboratory Manual* (1982) Cold Spring Harbor Laboratory Press, Cold Spring Harbor, N.Y.), Southern blot (Southern, *J. Mol. Biol.* 98: 503 (1975)), northern blot (identical to Southern blot to the exception that RNA is used as a target), or the sandwich technique (Dunn et al., *Cell* 12: 23 (1977)). The latter technique involves the use of a specific capture probe and/or a specific detection probe with nucleotide sequences that at least partially differ from each other.

A primer is usually a probe of about 10 to about 40 nucleotides that is used to initiate enzymatic polymerization of DNA in an amplification process (e.g., PCR), in an elongation process, or in a reverse transcription method. In a diagnostic method involving PCR, primers can be labelled.

Thus, the invention also encompasses (i) a reagent containing a probe of the invention for detecting and/or identifying the presence of Chlamydia in a biological material; (ii) a method for detecting and/or identifying the presence of Chlamydia in a biological material, in which (a) a sample is recovered or derived from the biological material, (b) DNA or RNA is extracted from the material and denatured, and (c) exposed to a probe of the invention, for example, a capture, detection probe or both, under stringent hybridization conditions, such that hybridization is detected; and (iii) a method for detecting and/or identifying the presence of Chlamydia in a biological material, in which (a) a sample is recovered or derived from the biological material, (b) DNA is extracted therefrom, (c) the extracted DNA is primed with at least one, and preferably two, primers of the invention and amplified by polymerase chain reaction, and (d) the amplified DNA fragment is produced.

As previously mentioned, polypeptides that can be produced upon expression of the newly identified open reading frames are useful vaccine agents.

Therefore, a sixth aspect of the invention features a substantially purified polypeptide or polypeptide derivative having an amino acid sequence encoded by a polynucleotide of the invention.

A "substantially purified polypeptide" is defined as a polypeptide that is separated from the environment in which it naturally occurs and/or that is free of the majority of the polypeptides that are present in the environment in which it was synthesized. For example, a substantially purified polypeptide is free from cytoplasmic polypeptides. Those skilled in the art will understand that the polypeptides of the invention can be purified from a natural source, i.e., a Chlamydia strain, or can be produced by recombinant means.

Homologous polypeptides or polypeptide derivatives encoded by polynucleotides of the invention can be screened for specific antigenicity by testing cross-reactivity with an antiserum raised against the polypeptide of reference having an amino acid sequence as shown in SEQ ID NOS: 1 and 2. Briefly, a monospecific hyperimmune antiserum can be raised against a purified reference polypeptide as such or as a fusion polypeptide, for example, an expression product of MBP, GST, or His-tag systems or a synthetic peptide predicted to be antigenic. The homologous polypeptide or derivative screened for specific antigenicity can be produced as such or as a fusion polypeptide. In this latter case and if the antiserum is also raised against a fusion polypeptide, two different fusion systems are employed. Specific antigenicity can be determined according to a number of methods, including Western blot (Towbin et al., *Proc. Natl. Acad. Sci. USA* 76: 4350 (1979)), dot blot, and ELISA, as described below.

In a Western blot assay, the product to be screened, either as a purified preparation or a total *E. coli* extract, is submitted to SDS-Page electrophoresis as described by Laemmli, *Nature* 227: 680 (1970). After transfer to a nitrocellulose membrane, the material is further incubated with the monospecific hyperimmune antiserum diluted in the range of dilutions from about 1:5 to about 1:5000, preferably from about 1:100 to about 1:500. Specific antigenicity is shown once a band corresponding to the product exhibits reactivity at any of the dilutions in the above range.

In an ELISA assay, the product to be screened is preferably used as the coating antigen. A purified preparation is preferred, although a whole cell extract can also be used. Briefly, about 100 $\mu$l of a preparation at about 10 $\mu$g protein/ml are distributed into wells of a 96-well polycarbonate ELISA plate. The plate is incubated for 2 hours at 37° C. then overnight at 4° C. The plate is washed with phosphate buffer saline (PBS) containing 0.05% Tween 20 (PBS/Tween buffer). The wells are saturated with 250 $\mu$l PBS containing 1% bovine serum albumin (BSA) to prevent non-specific antibody binding. After 1 hour incubation at 37° C., the plate is washed with PBS/Tween buffer. The antiserum is serially diluted in PBS/Tween buffer containing 0.5% BSA. 100 $\mu$l of dilutions are added per well. The plate is incubated for 90 minutes at 37° C., washed and evaluated according to standard procedures. For example, a goat anti-rabbit peroxidase conjugate is added to the wells when specific antibodies were raised in rabbits. Incubation is carried out for 90 minutes at 37° C. and the plate is washed. The reaction is developed with the appropriate substrate and the reaction is measured by colorimetry (absorbance measured spectrophotometrically). Under the above experimental conditions, a positive reaction is shown by O.D. values greater than a non immune control serum.

In a dot blot assay, a purified product is preferred, although a whole cell extract can also be used. Briefly, a solution of the product at about 100 $\mu$g/ml is serially two-fold diluted in 50 mM Tris-HCl (pH 7.5). 100 $\mu$l of each dilution are applied to a nitrocellulose membrane 0.45 $\mu$m set in a 96-well dot blot apparatus (Biorad). The buffer is removed by applying vacuum to the system. Wells are washed by addition of 50 mM Tris-HCl (pH 7.5) and the membrane is air-dried. The membrane is saturated in blocking buffer (50 mM Tris-HCl (pH 7.5) 0.15 M NaCl, 10 g/L skim milk) and incubated with an antiserum dilution from about 1:50 to about 1:5000, preferably about 1:500. The reaction is revealed according to standard procedures. For example, a goat anti-rabbit peroxidase conjugate is added to the wells when rabbit antibodies are used. Incubation is carried out 90 minutes at 37° C. and the blot is washed. The reaction is developed with the appropriate substrate and stopped. The reaction is measured visually by the appearance of a colored spot, e.g., by colorimetry. Under the above experimental conditions, a positive reaction is shown once a colored spot is associated with a dilution of at least about 1:5, preferably of at least about 1:500.

Therapeutic or prophylactic efficacy of a polypeptide or derivative of the invention can be evaluated as described below.

According to a seventh aspect of the invention, there is provided (i) a composition of matter containing a polypeptide of the invention together with a diluent or carrier; in particular, (ii) a pharmaceutical composition containing a therapeutically or prophylactically effective amount of a polypeptide of the invention; (iii) a method for inducing an immune response against Chlamydia in a mammal, by administering to the mammal an immunogenically effective amount of a polypeptide of the invention to elicit an immune response, e.g., a protective immune response to Chlamydia; and particularly, (iv) a method for preventing and/or treating a Chlamydia (e.g., *C. trachomatis, C. psittaci, C. pneumoniae*, or *C. pecorum*) infection, by administering a prophylactic or therapeutic amount of a polypeptide of the invention to an individual in need. Additionally, the seventh aspect of the invention encompasses the use of a polypeptide of the invention in the preparation of a medicament for preventing and/or treating Chlamydia infection.

The immunogenic compositions of the invention can be administered by any conventional route in use in the vaccine field, in particular to a mucosal (e.g., ocular, intranasal, pulmonary, oral, gastric, intestinal, rectal, vaginal, or urinary tract) surface or via the parenteral (e.g., subcutaneous, intradermal, intramuscular, intravenous, or intraperitoneal) route. The choice of the administration route depends upon a number of parameters, such as the adjuvant associated with the polypeptide. For example, if a mucosal adjuvant is used, the intranasal or oral route will be preferred and if a lipid formulation or an aluminum compound is used, the parenteral route will be preferred. In the latter case, the subcutaneous or intramuscular route is most preferred. The choice can also depend upon the nature of the vaccine agent. For example, polypeptide of the invention fused to CTB or LTB will be best administered to a mucosal surface.

A composition of the invention can contain one or several polypeptides or derivatives of the invention. It can also contain at least one additional Chlamydia antigen, or a subunit, fragment, homolog, mutant, or derivative thereof.

For use in a composition of the invention, a polypeptide or derivative thereof can be formulated into or with liposomes, preferably neutral or anionic liposomes, microspheres, ISCOMS, or virus-like-particles (VLPs) to facilitate delivery and/or enhance the immune response. These compounds are readily available to one skilled in the art; for example, see *Liposomes: A Practical Approach* (supra).

Adjuvants other than liposomes and the like can also be used and are known in the art. An appropriate selection can conventionally be made by those skilled in the art, for example, from the list provided below.

Administration can be achieved in a single dose or repeated as necessary at intervals as can be determined by one skilled in the art. For example, a priming dose can be followed by three booster doses at weekly or monthly intervals. An appropriate dose depends on various parameters including the recipient (e.g., adult or infant), the particular vaccine antigen, the route and frequency of administration, the presence/absence or type of adjuvant, and the desired effect (e.g., protection and/or treatment), as can be determined by one skilled in the art. In general, a vaccine antigen of the invention can be administered by a mucosal route in an amount from about 10 $\mu$g to about 500 mg, preferably from about I mg to about 200 mg. For the parenteral route of administration, the dose usually should not exceed about I mg, preferably about 100 $\mu$g.

When used as vaccine agents, polynucleotides and polypeptides of the invention can be used sequentially as part of a multistep immunization process. For example, a mammal can be initially primed with a vaccine vector of the invention such as a pox virus, e.g., via the parenteral route, and then boosted twice with the polypeptide encoded by the vaccine vector, e.g., via the mucosal route. In another example, liposomes associated with a polypeptide or derivative of the invention can also be used for priming, with boosting being carried out mucosally using a soluble polypeptide or derivative of the invention in combination with a mucosal adjuvant (e.g., LT).

A polypeptide derivative of the invention is also useful as a diagnostic reagent for detecting the presence of anti-Chlamydia antibodies, e.g., in a blood sample. Such polypeptides are about 5 to about 80, preferably about 10 to about 50 amino acids in length and can be labeled or unlabeled, depending upon the diagnostic method. Diagnostic methods involving such a reagent are described below.

Upon expression of a DNA molecule of the invention, a polypeptide or polypeptide derivative is produced and can be purified using known laboratory techniques. For example, the polypeptide or polypeptide derivative can be produced as a fusion protein containing a fused tail that facilitates purification. The fusion product can be used to immunize a small mammal, e.g., a mouse or a rabbit, in order to raise antibodies against the polypeptide or polypeptide derivative (monospecific antibodies). The eighth aspect of the invention thus provides a monospecific antibody that binds to a polypeptide or polypeptide derivative of the invention.

By "monospecific antibody" is meant an antibody that is capable of reacting with a unique naturally-occurring Chlamydia polypeptide. An antibody of the invention can be polyclonal or monoclonal. Monospecific antibodies can be recombinant, e.g., chimeric (e.g., constituted by a variable region of murine origin associated with a human constant region), humanized (a human immunoglobulin constant backbone together with hypervariable region of animal, e.g., murine, origin), and/or single chain. Both polyclonal and monospecific antibodies can also be in the form of immunoglobulin fragments, e.g., F(ab)'2 or Fab fragments. The antibodies of the invention can be of any isotype, e.g., IgG or IgA, and polyclonal antibodies can be of a single isotype or can contain a mixture of isotypes.

The antibodies of the invention, which are raised to a polypeptide or polypeptide derivative of the invention, can be produced and identified using standard immunological assays, e.g., Western blot analysis, dot blot assay, or ELISA (see, e.g., Coligan et al., *Current Protocols in Immunology* (1994) John Wiley & Sons, Inc., New York, N.Y.). The antibodies can be used in diagnostic methods to detect the presence of a Chlamydia antigen in a sample, such as a biological sample. The antibodies can also be used in affinity chromatography methods for purifying a polypeptide or polypeptide derivative of the invention. As is discussed further below, such antibodies can be used in prophylactic and therapeutic passive immunization methods.

Accordingly, a ninth aspect of the invention provides (i) a reagent for detecting the presence of Chlamydia in a biological sample that contains an antibody, polypeptide, or polypeptide derivative of the invention; and (ii) a diagnostic method for detecting the presence of Chlamydia in a biological sample, by contacting the biological sample with an antibody, a polypeptide, or a polypeptide derivative of the invention, such that an immune complex is formed, and by detecting such complex to indicate the presence of Chlamydia in the sample or the organism from which the sample is derived.

Those skilled in the art will understand that the immune complex is formed between a component of the sample and the antibody, polypeptide, or polypeptide derivative, whichever is used, and that any unbound material can be removed prior to detecting the complex. As can be easily understood, a polypeptide reagent is useful for detecting the presence of anti-Chlamydia antibodies in a sample, e.g., a blood sample, while an antibody of the invention can be used for screening a sample, such as a gastric extract or biopsy, for the presence of Chliamydia polypeptides.

For use in diagnostic applications, the reagent (i.e., the antibody, polypeptide, or polypeptide derivative of the invention) can be in a free state or immobilized on a solid support, such as a tube, a bead, or any other conventional support used in the field. Immobilization can be achieved using direct or indirect means. Direct means include passive adsorption (non-covalent binding) or covalent binding between the support and the reagent. By "indirect means" is meant that an anti-reagent compound that interacts with a reagent is first attached to the solid support. For example, if a polypeptide reagent is used, an antibody that binds to it can serve as an anti-reagent, provided that it binds to an epitope that is not involved in the recognition of antibodies in biological samples. Indirect means can also employ a ligand-receptor system, for example, a molecule such as a vitamin can be grafted onto the polypeptide reagent and the corresponding receptor can be immobilized on the solid phase. This is illustrated by the biotin-streptavidin system. Alternatively, indirect means can be used, e.g., by adding to the reagent a peptide tail, chemically or by genetic engineering, and immobilizing the grafted or fused product by passive adsorption or covalent linkage of the peptide tail.

According to a tenth aspect of the invention, there is provided a process for purifying, from a biological sample, a polypeptide or polypeptide derivative of the invention, which involves carrying out antibody-based affinity chromatography with the biological sample, wherein the antibody is a monospecific antibody of the invention.

For use in a purification process of the invention, the antibody can be polyclonal or monospecific, and preferably is of the IgG type. Purified IgGs can be prepared from an antiserum using standard methods (see, e.g., Coligan et al., supra). Conventional chromatography supports, as well as standard methods for grafting antibodies, are disclosed in, e.g., *Antibodies: A Laboratory Manual*, D. Lane, E. Harlow, Eds. (1988).

Briefly, a biological sample, such as an *C. pneumoniae* extract, preferably in a buffer solution, is applied to a chromatography material, preferably equilibrated with the buffer used to dilute the biological sample so that the polypeptide or polypeptide derivative of the invention (i.e., the antigen) is allowed to adsorb onto the material. The chromatography material, such as a gel or a resin coupled to an antibody of the invention, can be in batch form or in a column. The unbound components are washed off and the antigen is then eluted with an appropriate elution buffer, such as a glycine buffer or a buffer containing a chaotropic agent, e.g., guanidine HCl, or high salt concentration (e.g., 3 M $MgCl_2$). Eluted fractions are recovered and the presence of the antigen is detected, e.g., by measuring the absorbance at 280 nm.

An antibody of the invention can be screened for therapeutic efficacy as described as follows. According to an eleventh aspect of the invention, there is provided: (i) a composition of matter containing a monospecific antibody of the invention, together with a diluent or carrier; (ii) a pharmaceutical composition containing a therapeutically or prophylactically effective amount of a monospecific antibody of the invention, and (iii) a method for treating or preventing a Chlamydia (e.g., *C. trachomatis, C. psittaci, C. pneumoniae* or *C. pecorum*) infection, by administering a therapeutic or prophylactic amount of a monospecific antibody of the invention to an individual in need. Additionally, the eleventh aspect of the invention encompasses the use of a monospecific antibody of the invention in the preparation of a medicament for treating or preventing Chlamydia infection.

To this end, the monospecific antibody can be polyclonal or monoclonal, preferably of the IgA isotype (predominantly). In passive immunization, the antibody can be administered to a mucosal surface of a mammal, e.g., the gastric mucosa, e.g., orally or intragastrically, advantageously, in the presence of a bicarbonate buffer. Alternatively, systemic administration, not requiring a bicarbonate buffer, can be carried out. A monospecific antibody of the invention can be administered as a single active component or as a mixture with at least one monospecific antibody specific for a different Chlamydia polypeptide. The amount of antibody and the particular regimen used can be readily determined by one skilled in the art. For example, daily administration of about 100 to 1,000 mg of antibodies over one week, or three doses per day of about 100 to 1,000 mg of antibodies over two or three days, can be an effective regimens for most purposes.

Therapeutic or prophylactic efficacy can be evaluated using standard methods in the art, e.g., by measuring induction of a mucosal immune response or induction of protective and/or therapeutic immunity, using, e.g., the *C. pneumoniae* mouse model. Those skilled in the art will recognize that the *C. pneumoniae* strain of the model can be replaced with another Chlamydia strain. For example, the efficacy of DNA molecules and polypeptides from *C. pneumoniae* is preferably evaluated in a mouse model using an *C. pneumoniae* strain. Protection can be determined by comparing the degree of Chlamydia infection to that of a control group. Protection is shown when infection is reduced by comparison to the control group. Such an evaluation can be made for polynucleotides, vaccine vectors, polypeptides and derivatives thereof, as well as antibodies of the invention.

Adjuvants useful in any of the vaccine compositions described above are as follows.

Adjuvants for parenteral administration include aluminum compounds, such as aluminum hydroxide, aluminum phosphate, and aluminum hydroxy phosphate. The antigen can be precipitated with, or adsorbed onto, the aluminum compound according to standard protocols. Other adjuvants, such as RIBI (ImmunoChem, Hamilton, Mont.), can be used in parenteral administration.

Adjuvants for mucosal administration include bacterial toxins, e.g., the cholera toxin (CT), the *E. coli* heat-labile toxin (LT), the *Clostridium difficile* toxin A and the pertussis toxin (PT), or combinations, subunits, toxoids, or mutants thereof. For example, a purified preparation of native cholera toxin subunit B (CTB) can be of use. Fragments, homologs, derivatives, and fusions to any of these toxins are also suitable, provided that they retain adjuvant activity. Preferably, a mutant having reduced toxicity is used. Suitable mutants are described, e.g., in WO 95/17211 (Arg-7-Lys CT mutant), WO 96/6627 (Arg-192-Gly LT mutant), and WO 95/34323 (Arg-9-Lys and Glu-129-Gly PT mutant). Additional LT mutants that can be used in the methods and compositions of the invention include, e.g., Ser-63-Lys, Ala-69-Gly, Glu-110-Asp, and Glu-112-Asp mutants. Other adjuvants, such as a bacterial monophosphoryl lipid A (MPLA) of, e.g., *E. coli, Salmonella minnesota, Salmonella typhimurium,* or *Shigella flexneri*; saponins, or polylactide glycolide (PLGA) microspheres, can also be used in mucosal administration.

Adjuvants useful for both mucosal and parenteral administrations include polyphosphazene (WO 95/2415), DC-chol (3b-(N-(N',N'-dimethyl aminomethane)-carbamoyl) cholesterol (U.S. Pat. No. 5,283,185 and WO 96/14831) and QS-21 (WO 88/9336).

Any pharmaceutical composition of the invention, containing a polynucleotide, a polypeptide, a polypeptide derivative, or an antibody of the invention, can be manufactured in a conventional manner. In particular, it can be formulated with a pharmaceutically acceptable diluent or carrier, e.g., water or a saline solution such as phosphate buffer saline. In general, a diluent or carrier can be selected on the basis of the mode and route of administration, and standard pharmaceutical practice. Suitable pharmaceutical carriers or diluents, as well as pharmaceutical necessities for their use in pharmaceutical formulations, are described in *Remington's Pharmaceutical Sciences*, a standard reference text in this field and in the USP/NF.

The invention also includes methods in which Chlamydia infection, are treated by oral administration of a Chlamydia polypeptide of the invention and a mucosal adjuvant, in combination with an antibiotic, an antacid, sucralfate, or a combination thereof. Examples of such compounds that can be administered with the vaccine antigen and the adjuvant are antibiotics, including, e.g., macrolides, tetracyclines, and derivatives thereof (specific examples of antibiotics that can be used include azithromycin or doxicyclin or immuno-modulators such as cytokines or steroids. In addition, compounds containing more than one of the above-listed components coupled together, can be used. The invention also includes compositions for carrying out these methods, i.e., compositions containing a Chlamydia antigen (or antigens) of the invention, an adjuvant, and one or more of the above-listed compounds, in a pharmaceutically acceptable carrier or diluent.

Amounts of the above-listed compounds used in the methods and compositions of the invention can readily be determined by one skilled in the art. In addition, one skilled in the art can readily design treatment/immunization schedules. For example, the non-vaccine components can be administered on days 1–14, and the vaccine antigen+ adjuvant can be administered on days 7, 14, 21, and 28.

The above disclosure generally describes the present invention. A more complete understanding can be obtained by reference to the following specific examples. These examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation. Polypeptides having a sequence homologous to one of the sequences shown in SEQ ID NOS: 1 and 2, include naturally-occurring allelic variants, as well as mutants or any other non-naturally occurring variants that are analogous in terms of antigenicity, to a polypeptide.

As is known in the art, an allelic variant is an alternate form of a polypeptide that is characterized as having a substitution, deletion, or addition of one or more amino acids that does not alter the biological function of the polypeptide. By "biological function" is meant the function of the polypeptide in the cells in which it naturally occurs, even if the function is not necessary for the growth or survival of the cells. For example, the biological function of a porin is to allow the entry into cells of compounds present in the extracellular medium. The biological function is distinct from the antigenic function. A polypeptide can have more than one biological function.

Allelic variants are very common in nature. For example, a bacterial species, e.g., *C. pneumoniae*, is usually represented by a variety of strains that differ from each other by minor allelic variations. Indeed, a polypeptide that fulfills the same biological function in different strains can have an amino acid sequence that is not identical in each of the strains. Such an allelic variation may be equally reflected at the polynucleotide level.

Support for the use of allelic variants of polypeptide antigens comes from, e.g., studies of the Chlamydial MOMP antigen. The amino acid sequence of the MOMP varies from strain to strain, yet cross-strain antibody binding plus neutralization of infectivity occurs, indicating that the MOMP, when used as an immunogen, is tolerant of amino acid variations.

Polynucleotides, e.g., DNA molecules, encoding allelic variants can easily be retrieved by polymerase chain reaction (PCR) amplification of genomic bacterial DNA extracted by conventional methods. This involves the use of synthetic oligonucleotide primers matching upstream and downstream of the 5' and 3' ends of the encoding domain. Suitable primers can be designed according to the nucleotide sequence information provided in SEQ ID NOS: 1 and 2. Typically, a primer can consist of 10 to 40, preferably 15 to 25 nucleotides. It may be also advantageous to select primers containing C and G nucleotides in a proportion sufficient to ensure efficient hybridization; e.g., an amount of C and G nucleotides of at least 40%, preferably 50% of the total nucleotide amount.

Useful homologs that do not naturally occur can be designed using known methods for identifying regions of an antigen that are likely to be tolerant of amino acid sequence changes and/or deletions. For example, sequences of the antigen from different species can be compared to identify conserved sequences.

Polypeptide derivatives that are encoded by polynucleotides of the invention include, e.g., fragments, polypeptides having large internal deletions derived from full-length polypeptides, and fusion proteins.

Polypeptide fragments of the invention can be derived from a polypeptide having a sequence homologous to any of the sequences shown in SEQ ID NO: 1, to the extent that the fragments retain the substantial antigenicity of the parent polypeptide (specific antigenicity). Polypeptide derivatives can also be constructed by large internal deletions that remove a substantial part of the parent polypeptide, while retaining specific antigenicity. Generally, polypeptide derivatives should be about at least 12 amino acids in length to maintain antigenicity. Advantageously, they can be at least 20 amino acids, preferably at least 50 amino acids, more preferably at least 75 amino acids, and most preferably at least 100 amino acids in length.

Useful polypeptide derivatives, e.g., polypeptide fragments, can be designed using computer-assisted analysis of amino acid sequences in order to identify sites in protein antigens having potential as surface-exposed, antigenic regions. See e.g., Hughes et al. *Infect. Immun.* 60: 3497 1992.

Polypeptide fragments and polypeptides having large internal deletions can be used for revealing epitopes that are otherwise masked in the parent polypeptide and that may be of importance for inducing a protective T cell-dependent immune response. Deletions can also remove immunodominant regions of high variability among strains.

It is an accepted practice in the field of immunology to use fragments and variants of protein immunogens as vaccines, as all that is required to induce an immune response to a protein is a small (e.g., 8 to 10 amino acid) immunogenic region of the protein. This has been done for a number of vaccines against pathogens other than Chlamydia. For example, short synthetic peptides corresponding to surface-exposed antigens of pathogens such as murine mammary tumor virus, peptide containing 11 amino acids; (see e.g., Dion et al., *Virology* 179: 474–477 (1990)) Semliki Forest virus, peptide containing 16 amino acids (see e.g., Snijders et al., *J. Gen. Virol.* 72: 557–565 (1991)), and canine parvovirus, 2 overlapping peptides, each containing 15 amino acids (see e.g., Langeveld et al. *Vaccine* 12: 1473–1480 (1994)), have been shown to be effective vaccine antigens against their respective pathogens.

Polynucleotides encoding polypeptide fragments and polypeptides having large internal deletions can be constructed using standard methods, for example, by PCR, including inverse PCR, by restriction enzyme treatment of the cloned DNA molecules, or by the method of Kunkel et al. (*Proc. Natl. Acad. Sci. USA* 82: 448 (1985)) using biological material available at Stratagene.

A polypeptide derivative can also be produced as a fusion polypeptide that contains a polypeptide or a polypeptide derivative of the invention fused, e.g., at the N- or C-terminal end, to any other polypeptide (hereinafter referred to as a peptide tail). Such a product can be easily obtained by translation of a genetic fusion, i.e., a hybrid gene. Vectors for expressing fusion polypeptides are commercially available, such as the pMal-c2 or pMal-p2 systems of New England Biolabs, in which the peptide tail is a maltose binding protein, the glutathione-S-transferase system of Pharmacia, or the His-Tag system available from Novagen. These and other expression systems provide convenient means for further purification of polypeptides and derivatives of the invention.

Another particular example of fusion polypeptides included in invention includes a polypeptide or polypeptide derivative of the invention fused to a polypeptide having adjuvant activity, such as, e.g., subunit B of either cholera toxin or *E. coli* heat-labile toxin. Several possibilities are can be used for achieving fusion. First, the polypeptide of the invention can be fused to the N-, or preferably, to the C-terminal end of the polypeptide having adjuvant activity. Second, a polypeptide fragment of the invention can be fused within the amino acid sequence of the polypeptide having adjuvant activity.

As stated above, the polynucleotides of the invention encode Chlamydia polypeptides in precursor or mature form. They can also encode hybrid precursors containing heterologous signal peptides, which can mature into polypeptides of the invention. By "heterologous signal peptide" is meant a signal peptide that is not found in the naturally-occurring precursor of a polypeptide of the invention.

A polynucleotide of the invention, having a homologous coding sequence, hybridizes, preferably under stringent conditions, to a polynucleotide having a sequence as shown in SEQ ID NOS: 1 or 2. Hybridization procedures are, e.g., described in Ausubel et al., *Current Protocols in Molecular Biology*, John Wiley & Sons Inc. (1994), Silhavy et al. *Experiments With Gene Fusions*, Cold Spring Harbor Laboratory Press (1984); Davis et al., *A Manual for Genetic Engineering: Advanced Bacterial Genetics*, Cold Spring Harbor Laboratory Press (1980). Important parameters that can be considered for optimizing hybridization conditions are reflected in a formula that allows calculation of a critical value, the melting temperature above which two complementary DNA strands separate from each other. Casey and Davidson, *Nucl. Acid Res.* 4: 1539 (1977). This formula is as follows: Tm=81.5+0.41×(% G+C)+16.6 log (cation ion concentration)−0.63×(% formamide)−600/base number. Under appropriate stringency conditions, hybridization temperature (Th) is approximately 20–40° C., 20–25° C., or, preferably 30–40° C. below the calculated Tm. Those skilled in the understand that optimal temperature and salt conditions can be readily determined empirically in preliminary experiments using conventional procedures.

For example, stringent conditions can be achieved, both for pre-hybridizing and hybridizing incubations, (i) within 4–16 hours at 42° C., in 6×SSC containing 50% formamide or (ii) within 4–16 hours at 65° C. in an aqueous 6×SSC solution (1 M NaCl, 0.1 M sodium citrate (pH 7.0)). Typically, hybridization experiments are performed at a temperature from 60 to 68° C., e.g., 65° C. At such a temperature, stringent hybridization conditions can be achieved in 6×SSC, preferably in 2×SSC or 1×SSC, more preferably in 0.5×SSc, 0.3×SSC or 0.1×SSC (in the absence of formamide). 1×SSC contains 0.15 M NaCl and 0.015 M sodium citrate.

For polynucleotides containing 30 to 600 nucleotides, the above formula is used and then is corrected by subtracting (600/polynucleotide size in base pairs). Stringency conditions are defined by a Th that is 5 to 10° C. below Tm.

Hybridization conditions with oligonucleotides shorter than 20–30 bases do not exactly follow the rules set forth above. In such cases, the formula for calculating the Tm is as follows: Tm=4×(G+C)+2(A+T). For example, an 18 nucleotide fragment of 50% G+C would have an approximate Tm of 54° C.

A polynucleotide molecule of the invention, containing RNA, DNA, or modifications or combinations thereof, can have various applications. For example, a DNA molecule can be used (i) in a process for producing the encoded polypeptide in a recombinant host system, (ii) in the construction of vaccine vectors such as poxviruses, which are further used in methods and compositions for preventing and/or treating Chlamydia infection, (iii) as a vaccine agent (as well as an RNA molecule), in a naked form or formulated with a delivery vehicle and, (iv) in the construction of attenuated Chlamydia strains that can over-express a polynucleotide of the invention or express it in a non-toxic, mutated form.

According to a second aspect of the invention, there is therefore provided (i) an expression cassette containing a DNA molecule of the invention placed under the control of the elements required for expression, in particular under the control of an appropriate promoter; (ii) an expression vector containing an expression cassette of the invention; (iii) a prokaryotic or eukaryotic cell transformed or transfected with an expression cassette and/or vector of the invention, as well as (iv) a process for producing a polypeptide or polypeptide derivative encoded by a polynucleotide of the invention, which involves culturing a prokaryotic or eukaryotic cell transformed or transfected with an expression cassette and/or vector of the invention, under conditions that allow expression of the DNA molecule of the invention and, recovering the encoded polypeptide or polypeptide derivative from the cell culture.

A recombinant expression system can be selected from prokaryotic and eukaryotic hosts. Eukaryotic hosts include yeast cells (e.g., *Saccharomyces cerevisiae* or *Pichia pastoris*), mammalian cells (e.g., COS1, NIH3T3, or JEG3 cells), arthropods cells (e.g., *Spodoptera frugiperda* (*SF*9) cells), and plant cells. Preferably, a prokaryotic host such as *E. coli* is used. Bacterial and eukaryotic cells are available from a number of different sources to those skilled in the art, e.g., the American Type Culture Collection (ATCC; Rockville, Md.).

The choice of the expression system depends on the features desired for the expressed polypeptide. For example, it may be useful to produce a polypeptide of the invention in a particular lipidated form or any other form.

The choice of the expression cassette will depend on the host system selected as well as the features desired for the expressed polypeptide. Typically, an expression cassette includes a promoter that is functional in the selected host system and can be constitutive or inducible; a ribosome binding site; a start codon (ATG) if necessary, a region encoding a signal peptide, e.g., a lipidation signal peptide; a DNA molecule of the invention; a stop codon; and optionally a 3' terminal region (translation and/or transcription terminator). The signal peptide encoding region is adjacent to the polynucleotide of the invention and placed in proper reading frame. The signal peptide-encoding region can be homologous or heterologous to the DNA molecule encoding the mature polypeptide and can be specific to the secretion apparatus of the host used for expression. The open reading frame constituted by the DNA molecule of the invention, solely or together with the signal peptide, is placed under the control of the promoter so that transcription and translation occur in the host system. Promoters, signal peptide encoding regions are widely known and available to those skilled in the art and includes, for example, the promoter of *Salmonella typhimurium* (and derivatives) that is inducible by arabinose (promoter araB) and is functional in Gram-negative bacteria such as *E. coli* (as described in U.S. Pat. No. 5,028,530 and in Cagnon et al., *Protein Engineering* 4: 843 (1991); the promoter of the gene of bacteriophage T7 encoding RNA polymerase, that is functional in a number of *E. coli* strains expressing T7 polymerase (described in U.S. Pat. No. 4,952,496); OspA lipidation signal peptide; and RlpB lipidation signal peptide. See Takase et al., *J. Bact.* 169: 5692 (1987).

The expression cassette is typically part of an expression vector, which is selected for its ability to replicate in the chosen expression system. Expression vectors (e.g., plasmids or viral vectors) can be chosen from those described in Pouwels et al. (*Cloning Vectors: A Laboratory Manual* 1985, Suppl., 1987). They can be purchased from various commercial sources.

Methods for transforming/transfecting host cells with expression vectors will depend on the host system selected as described in Ausubel et al., *Current Protocols in Molecular Biology*, John Wiley & Sons Inc. (1994)).

Upon expression, a recombinant polypeptide of the invention (or a polypeptide derivative) is produced and remains in the intracellular compartment, is secreted/excreted in the extracellular medium or in the periplasmic space, or is embedded in the cellular membrane. The polypeptide can then be recovered in a substantially purified form from the cell extract or from the supernatant after centrifugation of the recombinant cell culture. Typically, the recombinant polypeptide can be purified by antibody-based affinity purification or by any other method that can be readily adapted by a person skilled in the art, such as by genetic fusion to a small affinity binding domain. Antibody-based affinity purification methods are also available for purifying a polypeptide of the invention extracted from a Chlamydia strain. Antibodies useful for purifying by immunoaffinity the polypeptides of the invention can be obtained as described below.

A polynucleotide of the invention can also be useful in the vaccine field, e.g., for achieving DNA vaccination. There are two major possibilities, either using a viral or bacterial host as gene delivery vehicle (live vaccine vector) or administering the gene in a free form, e.g., inserted into a plasmid. Therapeutic or prophylactic efficacy of a polynucleotide of the invention can be evaluated as described below.

Accordingly, in a third aspect of the invention, there is provided (i) a vaccine vector such as a poxvirus, containing a DNA molecule of the invention, placed under the control of elements required for expression; (ii) a composition of matter containing a vaccine vector of the invention, together with a diluent or carrier; particularly, (iii) a pharmaceutical composition containing a therapeutically or prophylactically effective amount of a vaccine vector of the invention; (iv) a method for inducing an immune response against Chlamydia in a mammal (e.g., a human; alternatively, the method can be used in veterinary applications for treating or preventing Chlamydia infection of animals, e.g., cats or birds), which involves administering to the mammal an immunogenically effective amount of a vaccine vector of the invention to elicit an immune response, e.g., a protective or therapeutic immune response to Chlamydia; and particularly, (v) a method for preventing and/or treating a Chlamydia (e.g., *C. trachomatis, C. psittaci, C. pneumoniae, C. pecorum*) infection, which involves administering a prophylactic or therapeutic amount of a vaccine vector of the invention to an individual in need. Additionally, the third aspect of the invention encompasses the use of a vaccine vector of the invention in the preparation of a medicament for preventing and/or treating Chlamydia infection.

A vaccine vector of the invention can express one or several polypeptides or derivatives of the invention, as well as at least one additional Chlamydia antigen, fragment, homolog, mutant, or derivative thereof. In addition, it can express a cytokine, such as interleukin-2 (IL-2) or interleukin-12 (IL-12), that enhances the immune response (adjuvant effect). Thus, a vaccine vector can include an additional DNA sequence encoding, e.g., a chlamydial antigen, or a cytokine, placed under the control of elements required for expression in a mammalian cell.

Alternatively, a composition of the invention can include several vaccine vectors, each of them being capable of expressing a polypeptide or derivative of the invention. A composition can also contain a vaccine vector capable of expressing an additional Chlamydia antigen, or a subunit, fragment, homolog, mutant, or derivative thereof; or a cytokine such as IL-2 or IL-12.

In vaccination methods for treating or preventing infection in a mammal, a vaccine vector of the invention can be administered by any conventional route in use in the vaccine field, particularly, to a mucosal (e.g., ocular, intranasal, oral, gastric, pulmonary, intestinal, rectal, vaginal, or urinary tract) surface or via the parenteral (e.g., subcutaneous, intradermal, intramuscular, intravenous, or intraperitoneal) route. Preferred routes depend upon the choice of the vaccine vector. The administration can be achieved in a single dose or repeated at intervals. The appropriate dosage depends on various parameters understood by skilled artisans such as the vaccine vector itself, the route of administration or the condition of the mammal to be vaccinated (weight, age and the like).

Live vaccine vectors available in the art include viral vectors such as adenoviruses and poxviruses as well as bacterial vectors, e.g., Shigella, Salmonella, *Vibrio cholerae*, Lactobacillus, Bacille bilié de Calmette-Guérin (BCG), and Streptococcus.

An example of an adenovirus vector, as well as a method for constructing an adenovirus vector capable of expressing a DNA molecule of the invention, are described in U.S. Pat. No. 4,920,209. Poxvirus vectors that can be used include, e.g., vaccinia and canary pox virus, described in U.S. Pat. No. 4,722,848 and U.S. Pat. No. 5,364,773, respectively. Also see, e.g., Tartaglia et al., *Virology* 188: 217 (1992) for a description of a vaccinia virus vector; and Taylor et al, *Vaccine* 13: 539 (1995) for a reference of a canary pox.

Poxvirus vectors capable of expressing a polynucleotide of the invention can be obtained by homologous recombination as described in Kieny et al., *Nature* 312: 163 (1984) so that the polynucleotide of the invention is inserted in the viral genome under appropriate conditions for expression in mammalian cells. Generally, the dose of vaccine viral vector, for therapeutic or prophylactic use, can be of from about $1 \times 10^4$ to about $1 \times 10^{11}$, advantageously from about $1 \times 10^7$ to about $1 \times 10^{10}$, preferably of from about $1 \times 10^7$ to about $1 \times 10^9$ plaque-forming units per kilogram. Preferably, viral vectors are administered parenterally; for example, in 3 doses, 4 weeks apart. Those skilled in the art recognize that it is preferable to avoid adding a chemical adjuvant to a composition containing a viral vector of the invention and thereby minimizing the immune response to the viral vector itself.

Non-toxicogenic *Vibrio cholerae* mutant strains that are useful as a live oral vaccine are described in Mekalanos et al., *Nature* 306: 551 (1983) and U.S. Pat. No. 4,882,278 (strain in which a substantial amount of the coding sequence of each of the two ctxA alleles has been deleted so that no functional cholerae toxin is produced); WO 92/11354 (strain in which the irgA locus is inactivated by mutation; this mutation can be combined in a single strain with ctxA mutations); and WO 94/1533 (deletion mutant lacking functional ctxA and attRS1 DNA sequences). These strains can be genetically engineered to express heterologous antigens, as described in WO 94/19482. An effective vaccine dose of a *Vibrio cholerae* strain capable of expressing a polypeptide or polypeptide derivative encoded by a DNA molecule of the invention can contain, e.g., about $1 \times 10^5$ to about $1 \times 10^9$, preferably about $1 \times 10^6$ to about $1 \times 10^8$ viable bacteria in appropriate volume for the selected route of administration. Preferred routes of administration include all mucosal routes; most preferably, these vectors are administered intranasally or orally.

Attenuated *Salmonella typhimurium* strains, genetically engineered for recombinant expression of heterologous antigens or not, and their use as oral vaccines are described in Nakayama et al., *Bio/Technology* 6: 693 (1998) and WO 92/11361. Preferred routes of administration include all mucosal routes; most preferably, these vectors are administered intranasally or orally.

Others bacterial strains useful as vaccine vectors are described in High et al., *EMBO* 11: 1991 (1992) and Sizemore et al., *Science* 270: 299 (1995) (*Shigella flexneri*); Medaglini et al., *Proc. Natl. Acad. Sci. USA* 92: 6868 (1995) (*Streptococcus gordonii*); and Flynn, *Cell. Mol. Biol.* 40 (suppl. I): 31 (1994), WO 88/6626, WO 90/0594, WO 91/13157, WO 92/1796, and WO 92/21376 (Bacille Calmette Guerin).

In bacterial vectors, polynucleotide of the invention can be inserted into the bacterial genome or can remain in a free state, carried on a plasmid.

An adjuvant can also be added to a composition containing a vaccine bacterial vector. A number of adjuvants are known to those skilled in the art. Preferred adjuvants can be selected from the list provided below.

According to a fourth aspect of the invention, there is also provided (i) a composition of matter containing a polynucleotide of the invention, together with a diluent or carrier; (ii) a pharmaceutical composition containing a therapeutically or prophylactically effective amount of a polynucleotide of the invention; (iii) a method for inducing an immune response against Chlamydia, in a mammal, by administering to the mammal, an immunogenically effective amount of a polynucleotide of the invention to elicit an immune response, e.g., a protective immune response to Chlamydia; and particularly, (iv) a method for preventing and/or treating a Chlamydia (e.g., *C. trachomatis, C. psittaci, C. pneumoniae*, or *C. pecorum*) infection, by administering a prophylactic or therapeutic amount of a polynucleotide of the invention to an individual in need. Additionally, the fourth aspect of the invention encompasses the use of a polynucleotide of the invention in the preparation of a medicament for preventing and/or treating Chlamydia infection. The fourth aspect of the invention preferably includes the use of a DNA molecule placed under conditions for expression in a mammalian cell, e.g., in a plasmid that is unable to replicate in mammalian cells and to substantially integrate in a mammalian genome.

Polynucleotides (DNA or RNA) of the invention can also be administered as such to a mammal for vaccine, e.g., therapeutic or prophylactic, purpose. When a DNA molecule of the invention is used, it can be in the form of a plasmid that is unable to replicate in a mammalian cell and unable to integrate in the mammalian genome. Typically, a DNA molecule is placed under the control of a promoter suitable for expression in a mammalian cell. The promoter can function ubiquitously or tissue-specifically. Examples of non-tissue specific promoters include the early Cytomegalovirus (CMV) promoter (described in U.S. Pat. No. 4,168,062) and the Rous Sarcoma Virus promoter (described in Norton & Coffin, *Molec. Cell Biol.* 5: 281 (1985)). The desmin promoter (Li et al., *Gene* 78: 243 (1989); Li & Paulin, *J. Biol. Chem.* 266: 6562 (1991); and Li & Paulin, *J. Biol. Chem.* 268: 10403 (1993)) is tissue-specific and drives expression in muscle cells. More generally, useful vectors are described, i.a., WO 94/21797 and Hartikka et al., *Human Gene Therapy* 7:1205 (1996).

For DNA/RNA vaccination, the polynucleotide of the invention can encode a precursor or a mature form. When it encodes a precursor form, the precursor form can be homologous or heterologous. In the latter case, a eukaryotic leader sequence can be used, such as the leader sequence of the tissue-type plasminogen factor (tPA).

A composition of the invention can contain one or several polynucleotides of the invention. It can also contain at least one additional polynucleotide encoding another Chlamydia antigen such as urease subunit A, B, or both; or a fragment, derivative, mutant, or analog thereof. A polynucleotide encoding a cytokine, such as interleukin-2 (IL-2) or interleukin-12 (IL-12), can also be added to the composition so that the immune response is enhanced. These additional polynucleotides are placed under appropriate control for expression. Advantageously, DNA molecules of the invention and/or additional DNA molecules to be included in the same composition, can be carried in the same plasmid.

Standard techniques of molecular biology for preparing and purifying polynucleotides can be used in the preparation of polynucleotide therapeutics of the invention. For use as a vaccine, a polynucleotide of the invention can be formulated according to various methods.

First, a polynucleotide can be used in a naked form, free of any delivery vehicles, such as anionic liposomes, cationic lipids, microparticles, e.g., gold microparticles, precipitating agents, e.g., calcium phosphate, or any other transfection-facilitating agent. In this case, the polynucleotide can be simply diluted in a physiologically acceptable solution, such as sterile saline or sterile buffered saline, with or without a carrier. When present, the carrier preferably is isotonic, hypotonic, or weakly hypertonic, and has a relatively low ionic strength, such as provided by a sucrose solution, e.g., a solution containing 20% sucrose.

Alternatively, a polynucleotide can be associated with agents that assist in cellular uptake. It can be, i.a., (i) complemented with a chemical agent that modifies the cellular permeability, such as bupivacaine (see, e.g., WO 94/16737), (ii) encapsulated into liposomes, or (iii) associated with cationic lipids or silica, gold, or tungsten microparticles.

Anionic and neutral liposomes are well known in the art (see, e.g., *Liposomes: A Practical Approach*, RPC New Ed, IRL Press (1990), for a detailed description of methods for making liposomes) and are useful for delivering a large range of products, including polynucleotides.

Cationic lipids are also known in the art and are commonly used for gene delivery. Such lipids include Lipofectin™ also known as DOTMA (N-[1-(2,3-dioleyloxy) propyl]-N,N,N-trimethylammonium chloride), DOTAP (1,2-bis(oleyloxy)-3-(trimethylammonio)propane), DDAB (dimethyldioctadecylammonium bromide), DOGS (dioctadecylamidologlycyl spermine) and cholesterol derivatives such as DC-Chol (3beta-(N-(N',N'-dimethyl aminomethane)-carbamoyl)cholesterol). A description of these cationic lipids can be found in EP 187,702, WO 90/11092, U.S. Pat. No. 5,283,185, WO 91/15501, WO 95/26356, and U.S. Pat. No. 5,527,928. Cationic lipids for gene delivery are preferably used in association with a neutral lipid such as DOPE (dioleyl phosphatidylethanolamine), as described in, e.g., WO 90/11092.

Other transfection-facilitating compounds can be added to a formulation containing cationic liposomes. A number of them are described in, e.g., WO 93/18759, WO 93/19768, WO 94/25608, and WO 95/2397. They include, i.a., spermine derivatives useful for facilitating the transport of DNA through the nuclear membrane (see, for example, WO 93/18759) and membrane-permeabilizing compounds such as GALA, Gramicidine S, and cationic bile salts (see, for example, WO 93/19768).

Gold or tungsten microparticles can also be used for gene delivery, as described in WO 91/359, WO 93/17706, and Tang et al. (*Nature* 356: 152 (1992)). In this case, the microparticle-coated polynucleotides can be injected via intradermal or intraepidermal routes using a needleless injection device ("gene gun"), such as those described in U.S. Pat. No. 4,945,050, U.S. Pat. No. 5,015,580, and WO 94/24263.

The amount of DNA to be used in a vaccine recipient depends, e.g., on the strength of the promoter used in the DNA construct, the immunogenicity of the expressed gene product, the condition of the mammal intended for administration (e.g., the weight, age, and general health of the mammal), the mode of administration, and the type of formulation. In general, a therapeutically or prophylactically effective dose from about 1 µg to about 1 mg, preferably, from about 10 µg to about 800 µg and, more preferably, from about 25 µg to about 250 µg, can be administered to human adults. The administration can be achieved in a single dose or repeated at intervals.

The route of administration can be any conventional route used in the vaccine field. As general guidance, a polynucleotide of the invention can be administered via a mucosal surface, e.g., an ocular, intranasal, pulmonary, oral, intestinal, rectal, vaginal, and urinary tract surface; or via a parenteral route, e.g., by an intravenous, subcutaneous, intraperitoneal, intradermal, intraepidermal, or intramuscular route. The choice of the administration route will depend on, e.g., the formulation that is selected. A polynucleotide formulated in association with bupivacaine is advantageously administered into muscles. When a neutral or anionic liposome or a cationic lipid, such as DOTMA or DC-Chol, is used, the formulation can be advantageously injected via intravenous, intranasal (aerosolization), intramuscular, intradermal, and subcutaneous routes. A polynucleotide in a naked form can advantageously be administered via the intramuscular, intradermal, or subcutaneous routes.

Although not absolutely required, such a composition can also contain an adjuvant. If so, a systemic adjuvant that does not require concomitant administration in order to exhibit an adjuvant effect is preferable such as, e.g., QS21, which is described in U.S. Pat. No. 5,057,546.

The sequence information provided in the present application enables the design of specific nucleotide probes and primers that can be useful in diagnosis. Accordingly, in a fifth aspect of the invention, there is provided a nucleotide probe or primer having a sequence found in or derived by degeneracy of the genetic code from a sequence shown in SEQ ID NOS: 1 or 2.

The term "probe" as used in the present application refers to DNA (preferably single stranded) or RNA molecules (or modifications or combinations thereof) that hybridize under the stringent conditions, as defined above, to nucleic acid molecules having sequences homologous to those shown in SEQ ID NOS: 1 and 2, or to a complementary or anti-sense sequence. Generally, probes are significantly shorter than full-length sequences shown in SEQ ID NOS: 1 and 2; for example, they can contain from about 5 to about 100, preferably from about 10 to 25 about 80 nucleotides. In particular, probes have sequences that are at least 75%, preferably at least 85%, more preferably 95% homologous to a portion of a sequence as shown in SEQ ID NOS: 1 and 2 or that are complementary to such sequences. Probes can contain modified bases such as inosine, methyl-5-deoxycytidine, deoxyuridine, dimethylamino-5-deoxyuridine, or diamino-2,6-purine. Sugar or phosphate residues can also be modified or substituted. For example, a deoxyribose residue can be replaced by a polyamide (Nielsen et al., *Science* 254: 1497 (1991)) and phosphate residues can be replaced by ester groups such as diphosphate, alkyl, arylphosphonate and phosphorothioate esters. In addition, the 2'-hydroxyl group on ribonucleotides can be modified by including, e.g., alkyl groups.

Probes of the invention can be used in diagnostic tests, as capture or detection probes. Such capture probes can be conventionally immobilized on a solid support, directly or indirectly, by covalent means or by passive adsorption. A detection probe can be labeled by a detection marker selected from radioactive isotopes; enzymes such as peroxidase, alkaline phosphatase, and enzymes able to hydrolyze a chromogenic, fluorogenic, or luminescent substrate; compounds that are chromogenic, fluorogenic, or luminescent; nucleotide base analogs; and biotin.

Probes of the invention can be used in any conventional hybridization technique, such as dot blot (Maniatis et al., *Molecular Cloning: A Laboratory Manual* (1982) Cold Spring Harbor Laboratory Press, Cold Spring Harbor, N.Y.), Southern blot (Southern, *J. Mol. Biol.* 98: 503 (1975)), northern blot (identical to Southern blot to the exception that RNA is used as a target), or the sandwich technique (Dunn et al., *Cell* 12: 23 (1977)). The latter technique involves the use of a specific capture probe and/or a specific detection probe with nucleotide sequences that at least partially differ from each other.

A primer is usually a probe of about 10 to about 40 nucleotides that is used to initiate enzymatic polymerization of DNA in an amplification process (e.g., PCR), in an elongation process, or in a reverse transcription method. In a diagnostic method involving PCR, primers can be labeled.

Thus, the invention also encompasses (i) a reagent containing a probe of the invention for detecting and/or identifying the presence of Chlamydia in a biological material; (ii) a method for detecting and/or identifying the presence of Chlamydia in a biological material, in which (a) a sample is recovered or derived from the biological material, (b) DNA or RNA is extracted from the material and denatured, and (c) exposed to a probe of the invention, for example, a capture, detection probe or both, under stringent hybridization conditions, such that hybridization is detected; and (iii) a method for detecting and/or identifying the presence of Chlamydia in a biological material, in which (a) a sample is recovered or derived from the biological material, (b) DNA is extracted therefrom, (c) the extracted DNA is primed with at least one, and preferably two, primers of the invention and amplified by polymerase chain reaction, and (d) the amplified DNA fragment is produced.

As previously mentioned, polypeptides that can be produced upon expression of the newly identified open reading frames are useful vaccine agents.

Therefore, a sixth aspect of the invention features a substantially purified polypeptide or polypeptide derivative having an amino acid sequence encoded by a polynucleotide of the invention.

A "substantially purified polypeptide" is defined as a polypeptide that is separated from the environment in which it naturally occurs and/or that is free of the majority of the polypeptides that are present in the environment in which it was synthesized. For example, a substantially purified polypeptide is free from cytoplasmic polypeptides. Those skilled in the art will understand that the polypeptides of the invention can be purified from a natural source, i.e., a Chlamydia strain, or can be produced by recombinant means.

Homologous polypeptides or polypeptide derivatives encoded by polynucleotides of the invention can be screened for specific antigenicity by testing cross-reactivity with an antiserum raised against the polypeptide of reference having an amino acid sequence as shown in SEQ ID NO: 2. Briefly, a monospecific hyperimmune antiserum can be raised against a purified reference polypeptide as such or as a fusion polypeptide, for example, an expression product of MBP, GST, or His-tag systems or a synthetic peptide predicted to be antigenic. The homologous polypeptide or derivative screened for specific antigenicity can be produced as such or as a fusion polypeptide. In this latter case and if the antiserum is also raised against a fusion polypeptide, two different fusion systems are employed. Specific antigenicity can be determined according to a number of methods, including Western blot (Towbin et al., *Proc. Natl. Acad. Sci. USA* 76: 4350 (1979)), dot blot, and ELISA, as described below.

In a Western blot assay, the product to be screened, either as a purified preparation or a total *E. coli* extract, is submitted to SDS-Page electrophoresis as described by Laemmli (*Nature* 227: 680 (1970)). After transfer to a nitrocellulose membrane, the material is further incubated with the monospecific hyperimmune antiserum diluted in the range of dilutions from about 1:5 to about 1:5000, preferably from about 1:100 to about 1:500. Specific antigenicity is shown once a band corresponding to the product exhibits reactivity at any of the dilutions in the above range.

In an ELISA assay, the product to be screened is preferably used as the coating antigen. A purified preparation is preferred, although a whole cell extract can also be used. Briefly, about 100 μl of a preparation at about 10 μg protein/ml are distributed into wells of a 96-well polycarbonate ELISA plate. The plate is incubated for 2 hours at 37° C. then overnight at 4° C.

The plate is washed with phosphate buffer saline (PBS) containing 0.05% Tween 20 (PBS/Tween buffer). The wells are saturated with 250 μl PBS containing 1% bovine serum albumin (BSA) to prevent non-specific antibody binding. After 1 hour incubation at 37° C., the plate is washed with PBS/Tween buffer. The antiserum is serially diluted in PBS/Tween buffer containing 0.5% BSA. 100 μl of dilutions are added per well. The plate is incubated for 90 minutes at 37° C., washed and evaluated according to standard procedures. For example, a goat anti-rabbit peroxidase conjugate is added to the wells when specific antibodies were raised in rabbits. Incubation is carried out for 90 minutes at 37° C. and the plate is washed. The reaction is developed with the appropriate substrate and the reaction is measured by colorimetry (absorbance measured spectrophotometrically). Under the above experimental conditions, a positive reaction is shown by O.D. values greater than a non immune control serum.

In a dot blot assay, a purified product is preferred, although a whole cell extract can also be used. Briefly, a solution of the product at about 100 μg/ml is serially two-fold diluted in 50 mM Tris-HCl (pH 7.5). 100 μl of each dilution are applied to a nitrocellulose membrane 0.45 μm set in a 96-well dot blot apparatus (Biorad). The buffer is removed by applying vacuum to the system. Wells are washed by addition of 50 mM Tris-HCl (pH 7.5) and the membrane is air-dried. The membrane is saturated in blocking buffer (50 mM Tris-HCl (pH 7.5) 0.15 M NaCl, 10 g/L skim milk) and incubated with an antiserum dilution from about 1:50 to about 1:5000, preferably about 1:500. The reaction is revealed according to standard procedures. For example, a goat anti-rabbit peroxidase conjugate is added to the wells when rabbit antibodies are used. Incubation is carried out 90 minutes at 37° C. and the blot is washed. The reaction is developed with the appropriate substrate and stopped. The reaction is measured visually by the appearance of a colored spot, e.g., by colorimetry. Under the above experimental conditions, a positive reaction is shown once a colored spot is associated with a dilution of at least about 1:5, preferably of at least about 1:500.

Therapeutic or prophylactic efficacy of a polypeptide or derivative of the invention can be evaluated as described below.

According to a seventh aspect of the invention, there is provided (i) a composition of matter containing a polypeptide of the invention together with a diluent or carrier; in particular, (ii) a pharmaceutical composition containing a therapeutically or prophylactically effective amount of a polypeptide of the invention; (iii) a method for inducing an immune response against Chlamydia in a mammal, by administering to the mammal an immunogenically effective amount of a polypeptide of the invention to elicit an immune response, e.g., a protective immune response to Chlamydia; and particularly, (iv) a method for preventing and/or treating a Chlamydia (e.g., *C. trachomatis, C. psittaci, C. pneumoniae*, or *C. pecorum*) infection, by administering a prophylactic or therapeutic amount of a polypeptide of the invention to an individual in need. Additionally, the seventh aspect of the invention encompasses the use of a polypeptide of the invention in the preparation of a medicament for preventing and/or treating Chlamydia infection.

The immunogenic compositions of the invention can be administered by any conventional route in use in the vaccine field, in particular to a mucosal (e.g., ocular, intranasal, pulmonary, oral, gastric, intestinal, rectal, vaginal, or urinary tract) surface or via the parenteral (e.g., subcutaneous, intradermal, intramuscular, intravenous, or intraperitoneal) route. The choice of the administration route depends upon a number of parameters, such as the adjuvant associated with the polypeptide. For example, if a mucosal adjuvant is used, the intranasal or oral route will be preferred and if a lipid formulation or an aluminum compound is used, the parenteral route will be preferred. In the latter case, the subcutaneous or intramuscular route is most preferred. The choice can also depend upon the nature of the vaccine agent. For example, a polypeptide of the invention fused to CTB or LTB will be best administered to a mucosal surface.

A composition of the invention can contain one or several polypeptides or derivatives of the invention. It can also contain at least one additional Chlamydia antigen, or a subunit, fragment, homolog, mutant, or derivative thereof.

For use in a composition of the invention, a polypeptide or derivative thereof can be formulated into or with liposomes, preferably neutral or anionic liposomes, microspheres, ISCOMS, or virus-like-particles (VLPs) to facilitate delivery and/or enhance the immune response. These compounds are readily available to one skilled in the art; for example, see *Liposomes: A Practical Approach* (supra).

Adjuvants other than liposomes and the like can also be used and are known in the art. An appropriate selection can conventionally be made by those skilled in the art, for example, from the list provided below.

Administration can be achieved in a single dose or repeated as necessary at intervals as can be determined by one skilled in the art. For example, a priming dose can be followed by three booster doses at weekly or monthly intervals. An appropriate dose depends on various parameters including the recipient (e.g., adult or infant), the particular vaccine antigen, the route and frequency of administration, the presence/absence or type of adjuvant, and the desired effect (e.g., protection and/or treatment), as can be determined by one skilled in the art. In general, a vaccine antigen of the invention can be administered by a mucosal route in an amount from about 10 $\mu$g to about 500 mg, preferably from about 1 mg to about 200 mg. For the parenteral route of administration, the dose usually should not exceed about 1 mg, preferably about 100 $\mu$g.

When used as vaccine agents, polynucleotides and polypeptides of the invention can be used sequentially as part of a multistep immunization process. For example, a mammal can be initially primed with a vaccine vector of the invention such as a pox virus, e.g., via the parenteral route, and then boosted twice with the polypeptide encoded by the vaccine vector, e.g., via the mucosal route. In another example, liposomes associated with a polypeptide or derivative of the invention can also be used for priming, with boosting being carried out mucosally using a soluble polypeptide or derivative of the invention in combination with a mucosal adjuvant (e.g., LT).

A polypeptide derivative of the invention is also useful as a diagnostic reagent for detecting the presence of anti-Chlamydia antibodies, e.g., in a blood sample. Such polypeptides are about 5 to about 80, preferably about 10 to about 50 amino acids in length and can be labeled or unlabeled, depending upon the diagnostic method. Diagnostic methods involving such a reagent are described below.

Upon expression of a DNA molecule of the invention, a polypeptide or polypeptide derivative is produced and can be purified using known laboratory techniques. For example, the polypeptide or polypeptide derivative can be produced as a fusion protein containing a fused tail that facilitates purification. The fusion product can be used to immunize a small mammal, e.g., a mouse or a rabbit, in order to raise antibodies against the polypeptide or polypeptide derivative (monospecific antibodies). The eighth aspect of the invention thus provides a monospecific antibody that binds to a polypeptide or polypeptide derivative of the invention.

By "monospecific antibody" is meant an antibody that is capable of reacting with a unique naturally-occurring Chlamydia polypeptide. An antibody of the invention can be polyclonal or monoclonal. Monospecific antibodies can be recombinant, e.g., chimeric (e.g., constituted by a variable region of murine origin associated with a human constant region), humanized (a human immunoglobulin constant backbone together with hypervariable region of animal, e.g., murine, origin), and/or single chain. Both polyclonal and monospecific antibodies can also be in the form of immunoglobulin fragments, e.g., F(ab)'2 or Fab fragments. The antibodies of the invention can be of any isotype, e.g., IgG or IgA, and polyclonal antibodies can be of a single isotype or can contain a mixture of isotypes.

The antibodies of the invention, which are raised to a polypeptide or polypeptide derivative of the invention, can be produced and identified using standard immunological assays, e.g., Western blot analysis, dot blot assay, or ELISA (see, e.g., Coligan et al., Current Protocols in Immunology (1994) John Wiley & Sons, Inc., New York, N.Y.). The antibodies can be used in diagnostic methods to detect the presence of a Chlamydia antigen in a sample, such as a biological sample. The antibodies can also be used in affinity chromatography methods for purifying a polypeptide or polypeptide derivative of the invention. As is discussed further below, such antibodies can be used in prophylactic and therapeutic passive immunization methods.

Accordingly, a ninth aspect of the invention provides (i) a reagent for detecting the presence of Chlamydia in a biological sample that contains an antibody, polypeptide, or polypeptide derivative of the invention; and (ii) a diagnostic method for detecting the presence of Chlamydia in a biological sample, by contacting the biological sample with an antibody, a polypeptide, or a polypeptide derivative of the invention, such that an immune complex is formed, and by detecting such complex to indicate the presence of Chlamydia in the sample or the organism from which the sample is derived.

Those skilled in the art will understand that the immune complex is formed between a component of the sample and the antibody, polypeptide, or polypeptide derivative, whichever is used, and that any unbound material can be removed prior to detecting the complex. As can be easily understood, a polypeptide reagent is useful for detecting the presence of anti-Chlamydia antibodies in a sample, e.g., a blood sample, while an antibody of the invention can be used for screening a sample, such as a gastric extract or biopsy, for the presence of Chlamydia polypeptides.

For use in diagnostic applications, the reagent (i.e., the antibody, polypeptide, or polypeptide derivative of the invention) can be in a free state or immobilized on a solid support, such as a tube, a bead, or any other conventional support used in the field. Immobilization can be achieved using direct or indirect means. Direct means include passive adsorption (non-covalent binding) or covalent binding between the support and the reagent. By "indirect means" is meant that an anti-reagent compound that interacts with a reagent is first attached to the solid support. For example, if a polypeptide reagent is used, an antibody that binds to it can serve as an anti-reagent, provided that it binds to an epitope that is not involved in the recognition of antibodies in biological samples. Indirect means can also employ a ligand-receptor system, for example, a molecule such as a vitamin can be grafted onto the polypeptide reagent and the corresponding receptor can be immobilized on the solid phase. This is illustrated by the biotin-streptavidin system. Alternatively, indirect means can be used, e.g., by adding to the reagent a peptide tail, chemically or by genetic engineering, and immobilizing the grafted or fused product by passive adsorption or covalent linkage of the peptide tail.

According to a tenth aspect of the invention, there is provided a process for purifying, from a biological sample, a polypeptide or polypeptide derivative of the invention, which involves carrying out antibody-based affinity chromatography with the biological sample, wherein the antibody is a monospecific antibody of the invention.

For use in a purification process of the invention, the antibody can be polyclonal or monospecific, and preferably is of the IgG type. Purified IgGs can be prepared from an antiserum using standard methods (see, e.g., Coligan et al., supra). Conventional chromatography supports, as well as standard methods for grafting antibodies, are disclosed in, e.g., *Antibodies: A Laboratory Manual*, D. Lane, E. Harlow, Eds. (1988).

Briefly, a biological sample, such as an *C. pneumoniae* extract, preferably in a buffer solution, is applied to a chromatography material, preferably equilibrated with the buffer used to dilute the biological sample so that the polypeptide or polypeptide derivative of the invention (i.e., the antigen) is allowed to adsorb onto the material. The chromatography material, such as a gel or a resin coupled to an antibody of the invention, can be in batch form or in a column. The unbound components are washed off and the antigen is then eluted with an appropriate elution buffer, such as a glycine buffer or a buffer containing a chaotropic agent, e.g., guanidine HCl, or high salt concentration (e.g., 3 M $MgCl_2$). Eluted fractions are recovered and the presence of the antigen is detected, e.g., by measuring the absorbance at 280 nm.

An antibody of the invention can be screened for therapeutic efficacy as described as follows. According to an eleventh aspect of the invention, there is provided (i) a composition of matter containing a monospecific antibody of the invention, together with a diluent or carrier; (ii) a pharmaceutical composition containing a therapeutically or prophylactically effective amount of a monospecific antibody of the invention, and (iii) a method for treating or preventing a Chlamydia (e.g., *C. trachomatis, C. psittaci, C. pneumoniae* or *C. pecorum*) infection, by administering a therapeutic or prophylactic amount of a monospecific antibody of the invention to an individual in need. Additionally, the eleventh aspect of the invention encompasses the use of a monospecific antibody of the invention in the preparation of a medicament for treating or preventing Chlamydia infection.

To this end, the monospecific antibody can be polyclonal or monoclonal, preferably of the IgA isotype (predominantly). In passive immunization, the antibody can be administered to a mucosal surface of a mammal, e.g., the gastric mucosa, e.g., orally or intragastrically, advantageously, in the presence of a bicarbonate buffer. Alternatively, systemic administration, not requiring a bicarbonate buffer, can be carried out. A monospecific antibody of the invention can be administered as a single active component or as a mixture with at least one monospecific antibody specific for a different Chlamydia polypeptide. The amount of antibody and the particular regimen used can be readily determined by one skilled in the art. For example, daily administration of about 100 to 1,000 mg of antibodies over one week, or three doses per day of about 100 to 1,000 mg of antibodies over two or three days, can be an effective regimens for most purposes.

Therapeutic or prophylactic efficacy can be evaluated using standard methods in the art, e.g., by measuring induction of a mucosal immune response or induction of protective and/or therapeutic immunity, using, e.g., the *C. pneumoniae* mouse model. Those skilled in the art will recognize that the *C. pneumoniae* strain of the model can be replaced with another Chlamydia strain. For example, the efficacy of DNA molecules and polypeptides from *C. pneumoniae* is preferably evaluated in a mouse model using an *C. pneumoniae* strain. Protection can be determined by comparing the degree of Chlamydia infection to that of a control group. Protection is shown when infection is reduced by comparison to the control group. Such an evaluation can be made for polynucleotides, vaccine vectors, polypeptides and derivatives thereof, as well as antibodies of the invention.

Adjuvants useful in any of the vaccine compositions described above are as follows.

Adjuvants for parenteral administration include aluminum compounds, such as aluminum hydroxide, aluminum phosphate, and aluminum hydroxy phosphate. The antigen can be precipitated with, or adsorbed onto, the aluminum compound according to standard protocols. Other adjuvants, such as RIBI (ImmunoChem, Hamilton, Mont.), can be used in parenteral administration.

Adjuvants for mucosal administration include bacterial toxins, e.g., the cholera toxin (CT), the *E. coli* heat-labile toxin (LT), the *Clostridium difficile* toxin A and the pertussis toxin (PT), or combinations, subunits, toxoids, or mutants thereof. For example, a purified preparation of native cholera toxin subunit B (CTB) can be of use. Fragments, homologs, derivatives, and fusions to any of these toxins are also suitable, provided that they retain adjuvant activity. Preferably, a mutant having reduced toxicity is used. Suitable mutants are described, e.g., in WO 95/17211 (Arg-7-Lys CT mutant), WO 96/6627 (Arg-192-Gly LT mutant), and WO 95/34323 (Arg-9-Lys and Glu-129-Gly PT mutant). Additional LT mutants that can be used in the methods and compositions of the invention include, e.g., Ser-63-Lys, Ala-69-Gly, Glu-110-Asp, and Glu-112-Asp mutants. Other adjuvants, such as a bacterial monophosphoryl lipid A (MPLA) of, e.g., *E. coli, Salmonella minnesota, Salmonella typhimurium,* or *Shigella flexneri*; saponins, or polylactide glycolide (PLGA) microspheres, can also be used in mucosal administration.

Adjuvants useful for both mucosal and parenteral administrations include polyphosphazene (WO 95/2415), DC-chol (3b-(N-(N',N'-dimethyl aminomethane)-carbamoyl)cholesterol; U.S. Pat. No. 5,283,185 and WO 96/14831) and QS-21 (WO 88/9336).

Any pharmaceutical composition of the invention, containing a polynucleotide, a polypeptide, a polypeptide derivative, or an antibody of the invention, can be manufactured in a conventional manner. In particular, it can be formulated with a pharmaceutically acceptable diluent or carrier, e.g., water or a saline solution such as phosphate buffer saline. In general, a diluent or carrier can be selected on the basis of the mode and route of administration, and standard pharmaceutical practice. Suitable pharmaceutical carriers or diluents, as well as pharmaceutical necessities for their use in pharmaceutical formulations, are described in *Remington's Pharmaceutical Sciences*, a standard reference text in this field and in the USP/NF.

The invention also includes methods in which Chlamydia infection, are treated by oral administration of a Chlamydia polypeptide of the invention and a mucosal adjuvant, in combination with an antibiotic, an antacid, sucralfate, or a combination thereof. Examples of such compounds that can be administered with the vaccine antigen and the adjuvant are antibiotics, including, e.g., macrolides, tetracyclines, and derivatives thereof (specific examples of antibiotics that can be used include azithromycin or doxicyclin or immunomodulators such as cytokines or steroids. In addition, compounds containing more than one of the above-listed components coupled together, can be used. The invention also includes compositions for carrying out these methods, i.e., compositions containing a Chlamydia antigen (or antigens) of the invention, an adjuvant, and one or more of the above-listed compounds, in a pharmaceutically acceptable carrier or diluent.

Amounts of the above-listed compounds used in the methods and compositions of the invention can readily be determined by one skilled in the art. In addition, one skilled in the art can readily design treatment/immunization schedules. For example, the non-vaccine components can be administered on days 1–14, and the vaccine antigen+adjuvant can be administered on days 7, 14, 21, and 28.

The above disclosure generally describes the present invention. A more complete understanding can be obtained by reference to the following specific examples. These examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXAMPLE 1

Preparation of Plasmid Vectoe pCAI632 Containing the POMP91B Precursor Gene

This example illustrates the preparation of a plasmid vector pCAI632 containing the POMP91B precursor gene.

The POMP91B precursor gene was amplified from *Chlamydia pneumoniae* genomic DNA by polymerase chain reaction (PCR) using a 5 primer:

(5'ATAAGAAT <u>GCGGCCGC</u>CACCATGAAAACGTCTATTCGTAAGTTC 3') (SEQ ID NO: 3), which contains a NotI restriction site, a ribosome binding site, an initiation codon and a sequence at the 5' end of the POMP91B precursor coding sequence, and a 3' primer:

(5'CGG <u>GGTACC</u>GAAATCGTAATTTGCTTCCTATATC 3') SEQ ID NO: 4). The 3' primer includes the sequence encoding the C-terminal sequence of the POMP91B precursor and a KpnI restriction site. The stop codon was excluded and an additional nucleotide was inserted to obtain an in-frame fusion with the Histidine tag.

After amplification, the PCR fragment was purified using QIAquick™ PCR purification kit (Qiagen) and then digested with NotI and KpnI and cloned into the pCA-Myc-His eukaryotic expression vector describe in Example 2 (FIG. 3) with transcription under control of the human CMV promoter.

EXAMPLE 2

Preparation of the Eukaryotic Expression Vector pCA/Myc-His

This example illustrates the preparation of the eukaryotic expression vector pCA/Myc-His.

Plasmid pcDNA3.1(−)Myc-His C (Invitrogen) was restricted with SpeI and BamHI to remove the CMV promoter and the remaining vector fragment was isolated. The CMV promoter and intron A from plasmid VR-1012 (Vical) was isolated on a SpeI/BamHI fragment. The fragments were ligated together to produce plasmid pCA/Myc-His. The NotI/KpnI restricted PCR fragment containing the POMP91B precursor gene was ligated into the NotI and KpnI restricted plasmid pCA/Myc-His to produce plasmid pCAI632 (FIG. 3).

The resulting plasmid, pCAI632, was transfered by electroporation into *E. coli* XL-1 blue (Stratagene) which was grown in LB broth containing 50 μg/ml of carbenicillin. The plasmid was isolated by Endo Free Plasmid Giga Kit™ (Qiagen) large scale DNA purification system. DNA concentration was determined by absorbance at 260 nm and the plasmid was verified after gel electrophoresis and ethidium bromide staining and comparison to molecular weight standards. The 5' and 3' ends of the gene were verified by sequencing using a LiCor model 4000 L DNA sequencer and IRD-800 labelled primers.

EXAMPLE 3

Protection Against Intranasal *C. pneumoniae*

This example illustrates the immunization of mice to achieve protection against an intranasal challenge of *C. pneumoniae.*

It has been previously demonstrated (Yang et. al., 1993) that mice are susceptible to intranasal infection with different isolates of *C. pneumoniae*. Strain AR-39 (Grayston, 1989) was used in Balb/c mice as a challenge infection model to examine the capacity of chlamydia gene products delivered as naked DNA to elicit a protective response against a sublethal *C. pneumoniae* lung infection. Protective immunity is defined as an accelerated clearance of pulmonary infection.

Groups of 7 to 9 week old male Balb/c mice (8 to 10 per group) were immunized intramuscularly (i.m.) plus intranasally (i.n.) with plasmid DNA containing the coding sequence of *C. pneumoniae* POMP91B precursor as described in Example 1 and 2. Saline or the plasmid vector lacking an inserted chlamydial gene was given to groups of control animals.

For i.m. immunization alternate left and right quadriceps were injected with 100 μg of DNA in 50 μl of PBS on three occasions at 0, 3 and 6 weeks. For i.n. immunization, anaesthetized mice aspirated 50 μl of PBS containing 50 μg DNA on three occasions at 0, 3 and 6 weeks. At week 8, immunized mice were inoculated i.n. with $5\times10^5$ IFU of *C. pneumoniae*, strain AR39 in 100 μl of SPG buffer to test their ability to limit the growth of a sublethal *C. pneumoniae* challenge.

Lungs were taken from mice at days 5 and 9 post-challenge and immediately homogenised in SPG buffer (7.5% sucrose, 5 mM glutamate, 12.5 mM phosphate pH 7.5). The homogenate was stored frozen at −70° C. until assay. Dilutions of the homogenate were assayed for the presence of infectious chlamydia by inoculation onto monolayers of susceptible cells. The inoculum was centrifuged onto the cells at 3000 rpm for 1 hour, then the cells were incubated for three days at 35° C. in the presence of 1 μg/ml cycloheximide. After incubation the monolayers were fixed with formalin and methanol then immunoperoxidase stained for the presence of chlamydial inclusions using convalescent sera from rabbits infected with *C. pneumoniae* and metal-enhanced DAB as a peroxidase substrate.

Figure 4:
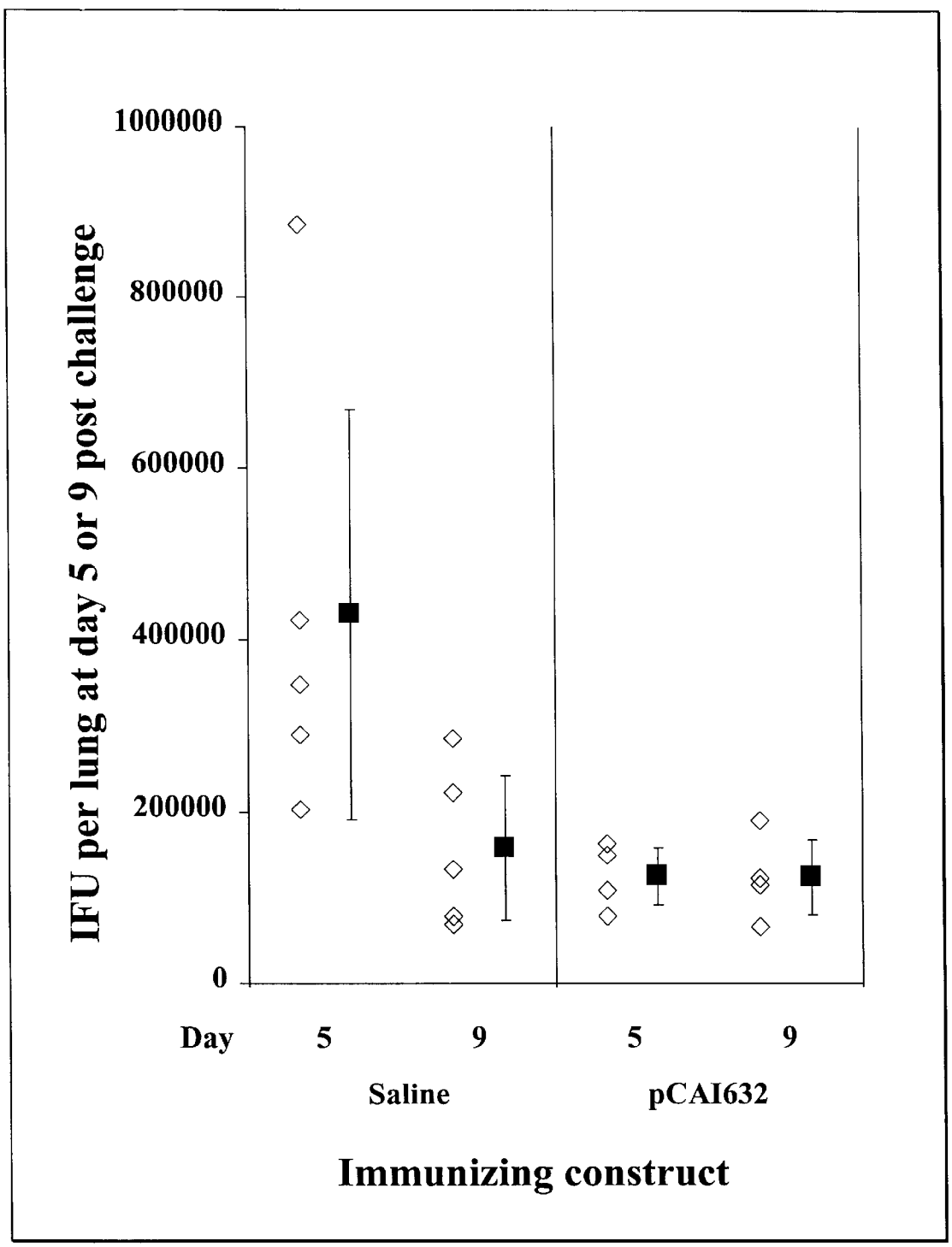
FIG. 4 illustrates protection against *C. pneumoniae* infection by pCAI632 following DNA immunization. Individual data points are shown for each anim uncharged polar side chains, such as asparagine, glutamine, serine, threonine, and tyrosine; (b) amino acids having basic side chains, such as lysine, arginine, and histidine; (c) amino acids having acidic side chains, such as aspartic acid and glutamic acid; and (d) amino acids having nonpolar side chains, such as glycine, alanine, valine, leucine, isoleucine, proline, phenylalanine, methionine, tryptophan, and cysteine.

FIG. 4 and Table 1 show that mice immunized i.n. and i.m. with pCAI632 had chlamdial lung titers less than 161,300 in 4 of 4 cases at day 5 and less than 188,400 in 4 of 4 cases at day 9 whereas the range of values for control mice sham immunized with saline was 202,400–866,800 IFU/lung (mean 429,800) at day 5 and 68,600–284,600 IFU/lung (mean 157,080) at day 9.

TABLE 1

BACTERIAL LOAD (INCLUSION FORMING UNITS PER LUNG) IN THE LUNGS OF BALB/C MICE IMMUNIZED WITH VARIOUS DNA IMMUNIZATION CONSTRUCTS

| | Immunizing Construct | | | |
|---|---|---|---|---|
| Mouse | Saline Day 5 | Saline Day 9 | pCAI632 Day 5 | pCAI632 Day 9 |
| 1 | 348200 | 68600 | 161300 | 66000 |
| 2 | 202400 | 284600 | 108600 | 188400 |
| 3 | 422400 | 132000 | 148400 | 114000 |
| 4 | 289200 | 78400 | 77800 | 121400 |
| 5 | 886800 | 221800 | | |
| MEAN | 429800 | 157080 | 124025 | 122450 |
| SD | 267881.24 | 93672.69 | 38114.947 | 50360.40 |

EQUIVALENTS

From the foregoing detailed description of the specific embodiments of the invention, it should be parent that a unique Chlamydia antigen has been described. Although particular embodiments have been disclosed herein in detail, this has been done by way of example for purposes of illustration only, and is not intended to be limiting with respect to the scope of the appended claims which follow. In particular, it is contemplated by the inventor that various substitutions, alterations, and modifications may be made to the invention without departing from the spirit and scope of the invention as defined by the claims.

What is claimed is:

1. An isolated polypeptide comprising a polypeptide from a strain of Chlamydia selected from the group consisting of:
   (a) a polypeptide comprising the amino acid sequence SEQ ID NO:2; and
   (b) a polypeptide that is at least 90% homologous to SEQ ID NO:2;
   wherein said isolated polypeptide, when administered in an immunogenically-effective amount to a mammal, induces a mucosal immune response by said mammal against *Chlamydia pneumoniae*.

2. The polypeptide of claim 1, wherein said polypeptide has the sequence of SEQ ID NO: 2.

3. A polypeptide comprising the polypeptide of claim 1 linked to a fusion polypeptide.

4. The polypeptide of claim 3, wherein the fusion polypeptide is a signal peptide.

5. The polypeptide of claim 3, wherein the fusion polypeptide comprises a heterologous polypeptide and wherein said heterologous polypeptide is an adjuvant.

* * * * *